(12) United States Patent
Akahori et al.

(10) Patent No.: US 10,753,922 B2
(45) Date of Patent: Aug. 25, 2020

(54) BIOMOLECULE MEASUREMENT APPARATUS

(71) Applicant: HITACHI HIGH-TECHNOLOGIES CORPORATION, Tokyo (JP)

(72) Inventors: Rena Akahori, Tokyo (JP); Kenichi Takeda, Tokyo (JP); Itaru Yanagi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 218 days.

(21) Appl. No.: 15/779,931

(22) PCT Filed: Nov. 29, 2016

(86) PCT No.: PCT/JP2016/085321
§ 371 (c)(1),
(2) Date: May 30, 2018

(87) PCT Pub. No.: WO2017/104398
PCT Pub. Date: Jun. 22, 2017

(65) Prior Publication Data
US 2018/0372712 A1  Dec. 27, 2018

(30) Foreign Application Priority Data

Dec. 17, 2015 (JP) .................................. 2015-246702

(51) Int. Cl.
*G01N 33/487* (2006.01)
*G01N 27/327* (2006.01)
(Continued)

(52) U.S. Cl.
CPC ... *G01N 33/48721* (2013.01); *G01N 27/3278* (2013.01); *G01N 27/4145* (2013.01); *B01L 3/502715* (2013.01)

(58) Field of Classification Search
CPC ......... G01N 33/48721; G01N 27/4145; G01N 27/3278
See application file for complete search history.

(56) References Cited

U.S. PATENT DOCUMENTS

2005/0098539 A1  5/2005  Tsunetomo et al.
2006/0057585 A1  3/2006  McAllister
(Continued)

FOREIGN PATENT DOCUMENTS

JP  2004-510433 A  4/2004
JP  2004-533608 A  11/2004
(Continued)

OTHER PUBLICATIONS

C. Hyun, et al. "Threading Immobilized DNA Molecules through a Solid-State Nanopore at >100 µs per Base Rate", ACS Nano, 7(7): p. 5892-5900, July (Year: 2013).*
(Continued)

*Primary Examiner* — J. Christopher Ball
(74) *Attorney, Agent, or Firm* — Mattingly & Malur, PC

(57) ABSTRACT

A biomolecule measuring device includes a first liquid tank and a second liquid tank which are filled with an electrolytic solution, a nanopore device that supports a thin film having a nanopore and is provided between the first liquid tank and the second liquid tank so as to communicate between the first liquid, tank and the second liquid tank through the nanopores, and an immobilizing member that is disposed in the first liquid tank, has a size larger than that of the thin film, and to which the biomolecules are immobilized, in which at least, one of the nanopore device and the immobilizing member has a groove structure.

16 Claims, 92 Drawing Sheets

(51) Int. Cl.
    *G01N 27/414*     (2006.01)
    *B01L 3/00*     (2006.01)

(56) References Cited

U.S. PATENT DOCUMENTS

| | | |
|---|---|---|
| 2014/0252505 A1 | 9/2014 | Kobayashi et al. |
| 2017/0268054 A1 | 9/2017 | Akahori et al. |

FOREIGN PATENT DOCUMENTS

| | | |
|---|---|---|
| JP | 2014-074599 A | 4/2014 |
| JP | 2014-173935 A | 9/2014 |
| WO | 02/29003 A2 | 4/2002 |
| WO | 02/079519 A1 | 10/2002 |
| WO | 2004/078668 A1 | 9/2004 |
| WO | 2012/138357 A1 | 10/2012 |
| WO | 2016/088486 A1 | 6/2019 |

OTHER PUBLICATIONS

Japanese Office Action received in corresponding Japanese Application No. 2017-555957 dated May 21, 2019.

Yusuke Goto, et al., Deceleration of single-stranded DNA passing through a nanopore using a nanometre-sized bead structure, Scientific Reports, Nov. 12, 2015, vol. 5, pp. 1-7.

International Search Report of PCT/JP2016/085321 dated Jan. 10, 2017.

\* cited by examiner

A=W_t $A_i = Wh_0 + w_1 h_1 n$
$n = W/w_2$
n:pitch number $R_1 = (L - nL_1)/(Wh_0 + w_1 h_1 n)$ FIG. 28
Cross-sectional view
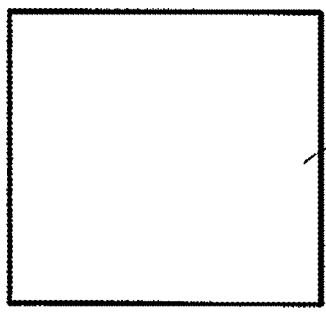
Top view FIG. 29
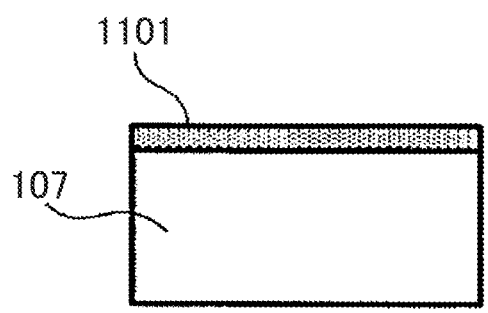
Cross-sectional view
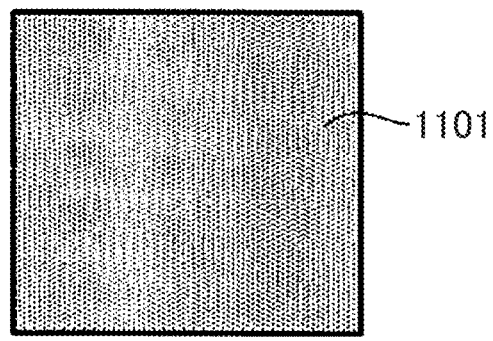
Top view FIG. 30
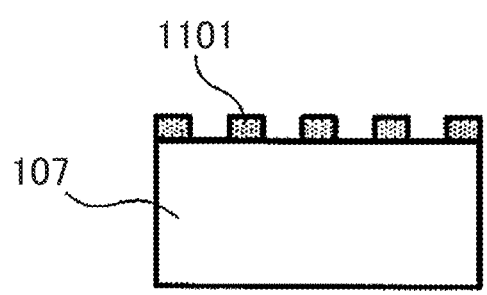
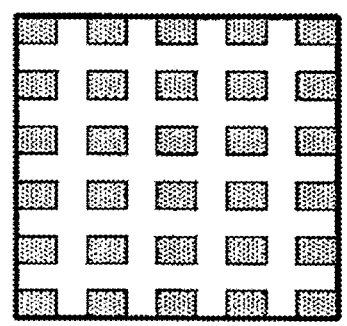
Cross-sectional view  Top view FIG. 31
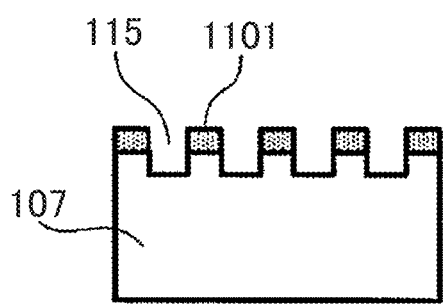
Cross-sectional view
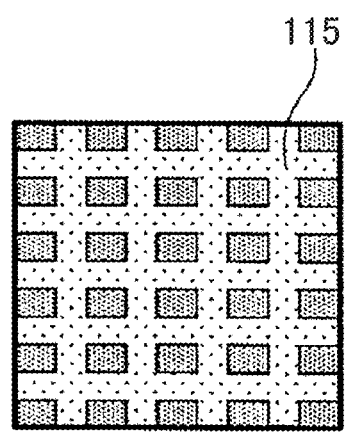
Top view FIG. 32
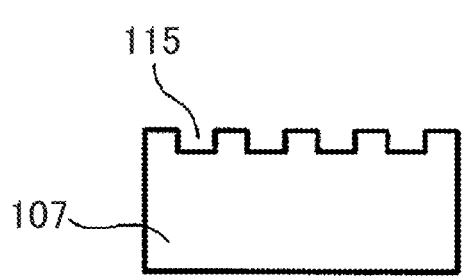
Cross-sectional view
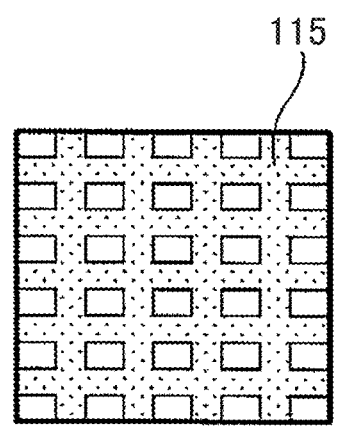
Top view FIG. 33
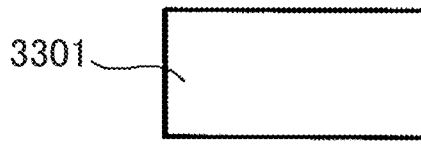
Cross-sectional view
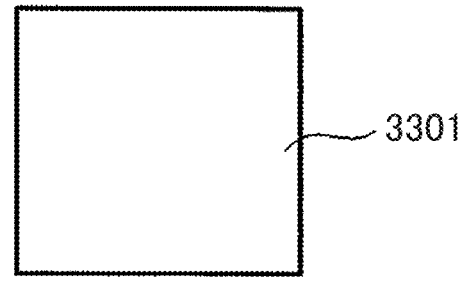
Top view FIG. 34
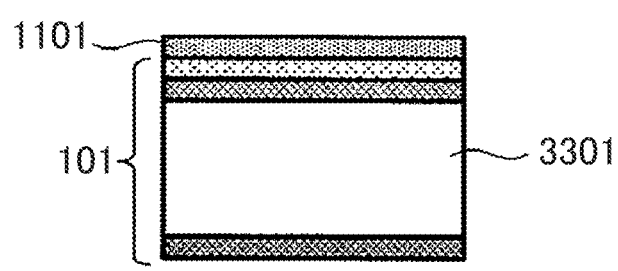
Cross-sectional view
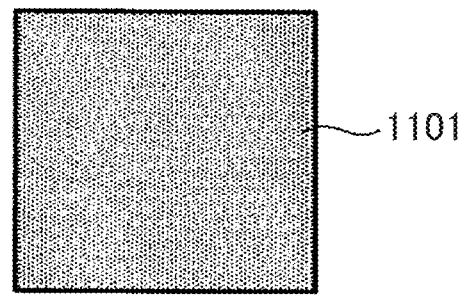
Top view FIG. 35
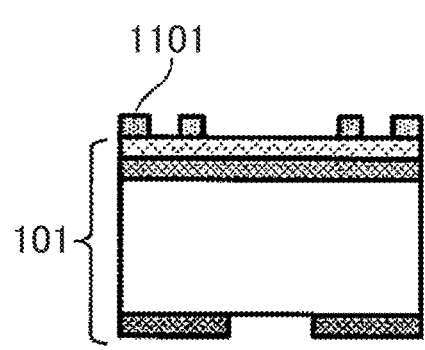
Cross-sectional view
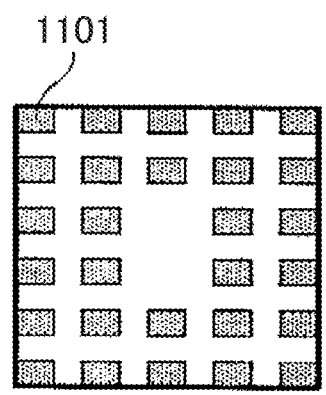
Top view FIG. 36
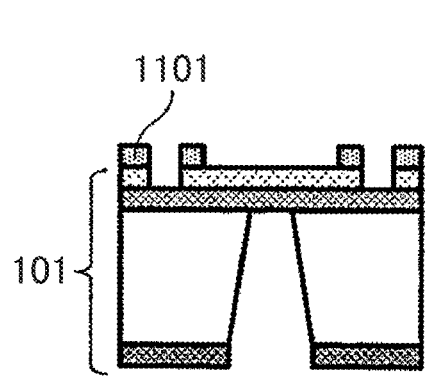
Cross-sectional view
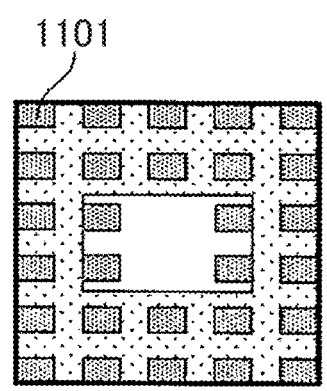
Top view FIG. 37
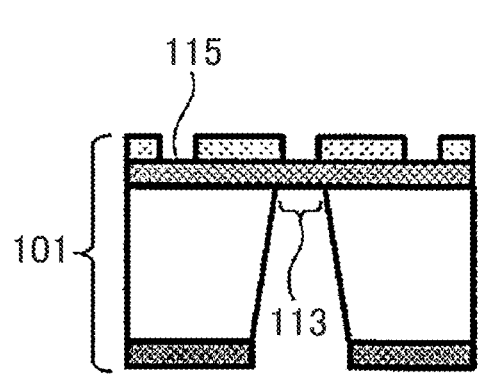
Cross-sectional view
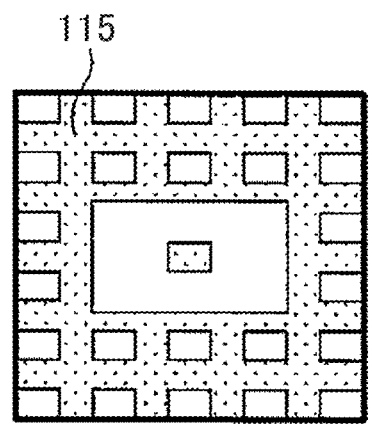
Top view FIG. 38
Cross-sectional view
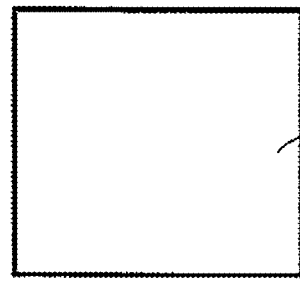
Top view FIG. 39
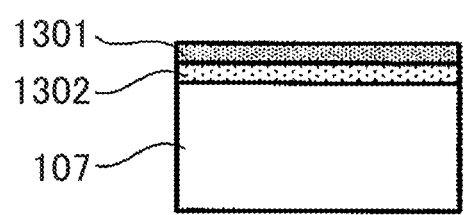
Cross-sectional view
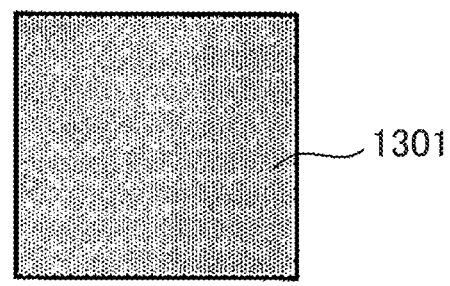
Top view FIG. 40
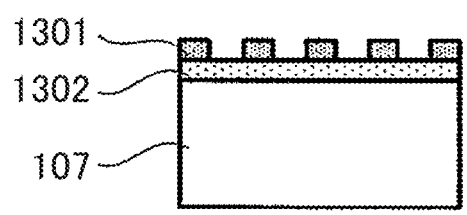
Cross-sectional view
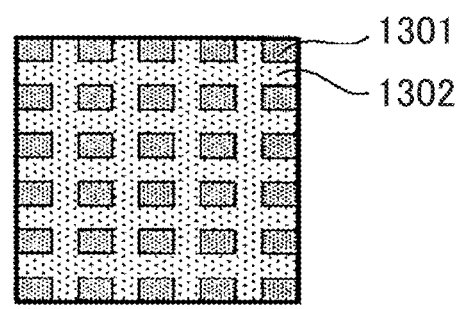
Top view

BIOMOLECULE MEASUREMENT APPARATUS

TECHNICAL FIELD

The present invention relates to a biomolecule measuring device using a nanopore.

BACKGROUND ART

As a next-generation DNA sequencer, a method for electrically directly measuring a DNA base sequence without elongation reaction and fluorescent label has attracted attention. In order to realize the above measuring method, the research and development of a nanopore DNA sequencing method for directly measuring a DNA fragment without the use of reagent to determine the base sequence has been actively advanced. The above method is based on a principle that when a DNA chain passes through a nanopore, a difference of the individual base types contained in the DNA chain is directly measured by a blockage current amount to sequentially identify the base types. Since amplification of a template DNA by enzyme is not carried out and no labeling substances such as fluorescent substances are used, the above method is expected to lead to a high throughput, a low running cost, and a long base length decoding.

One of the challenges of the nanopore method is transport control of the DNA that passes through the nanopore. In order to measure a difference between the individual base types contained in the DNA chain according to the blockade current amount, it is conceivable that a nanopore passage speed of the DNA is set to 100 μs or more per base according to a current noise at the time of measurement and a time constant of the fluctuation of DNA molecules. When sequencing DNA with the use of the nanopore, a potential gradient is formed with the use of electrodes located above and below the nanopore, and the DNA with a negative charge is allowed to pass through the nanopore. However, the nanopore passage speed of the DNA is usually as fast as 1 μs or less per base, which makes it difficult to sufficiently measure the blockade current derived from each base.

As one of the transport control methods, the DNA terminal to be read is immobilized at a leading end of an immobilized probe and minute displacement of the immobilized probe is controlled by an external drive mechanism (motor and piezo element), to thereby control the movement of the DNA passing through the nanopore.

CITATION LIST

Patent Literature

Patent Literature 1: US 2006/0057585 A1

SUMMARY OF INVENTION

Technical Problem

A signal measured by the biomolecule measuring device using a nanopore device is a rectangular staircase signal showing levels different depending on the type of monomer molecule configuring the biomolecule. A signal response speed of the biomolecule measuring device is defined by a solution resistance ($R_L$) of an electrolyte solution filled in the vicinity of the nanopore device, a capacity ($C_s$) of the nanopore device, and a passage resistance ($R_g$) defined by the size of a narrow region caused by the approach of the nanopore device and a fixed probe.

In the biomolecule measuring device, when the biomolecule is analyzed, the nanopore device and the fixed probe are made to approach each other. A distance between the nanopore device and the fixed probe decreases with the approach, resulting in an increase in passage resistance. This means a decrease in a signal time constant, resulting in blunting of an acquired signal waveform and a reduction in SN.

Accordingly, the present invention provides a technique for reducing a passage resistance of a solution and preventing a decrease in time constant.

Solution to Problem

In order to solve the above problem, the present invention proposes a method of forming a groove structure in at least one of an immobilizing member (fixed probe) and a nanopore device in a biomolecule measuring device to reduce an increase in passage resistance.

For example, in order to solve the above problem, the configuration defined in the claims is adopted. The present invention includes a plurality of means for solving the problems described above. For example, there is provided a biomolecule measuring device including: a first liquid tank filled with an electrolyte solution; a second liquid tank filled with the electrolytic solution; a nanopore device that supports a thin film having a nanopore and is provided between the first liquid tank and the second liquid tank to communicate the first liquid tank with the second liquid tank through the nanopores; an immobilizing member that is disposed in the first liquid tank, has a size larger than that of the thin film and to which biomolecules are immobilized; a driving mechanism that drives the immobilizing member in a direction closer to or away from the thin film; a first electrode that is provided in the first liquid tank; a second electrode that is provided in the second liquid tank; a stop mechanism that prevents a contact between the immobilizing member and the thin film; a power supply that applies a voltage between the first electrode and the second electrode; and a measurement unit that measures an ionic current flowing between the first electrode and the second electrode, in which at least one of the nanopore device and the immobilizing member has a groove structure in a region where the nanopore device and the immobilizing member are opposed to each other, and the measurement unit acquires sequence information on the biomolecules by an ionic current measured when the biomolecules immobilized on the immobilizing member pass through the nanopores.

According to another example, there is provided a biomolecule measuring device including: a first liquid tank filled with an electrolyte solution; a second liquid tank filled with the electrolytic solution; a nanopore device that supports a thin film having a nanopore and is provided between the first liquid tank and the second liquid tank to communicate the first liquid tank with the second liquid tank through the nanopores; a first electrode that is provided in the first liquid tank; a second electrode that is provided in the second liquid tank; a power supply that applies a voltage between the first electrode and the second electrode; and a measurement unit that measures an ionic current flowing between the first electrode and the second electrode, in which the first liquid tank has a micro flow path in a region in the vicinity of the nanopores, the nanopore device has a groove structure, and the measurement unit acquires sequence information on the biomolecules by an ionic current measured when the biomolecules pass through the nanopores.

According to another example, there is provided an immobilizing member for immobilizing the biomolecules in a biomolecule measuring device in which a groove structure is formed on a surface of the immobilizing member.

According to another example, there is provided a nanopore device for a biomolecule measuring device, including: a thin film having a nanopore; and a space defining member that is provided outside the thin film and defines a space around the nanopore, in which the space defining member has a groove structure.

Advantageous Effects of Invention

According to the present invention, the passage resistance of the solution can be reduced and a reduction of the time constant can be prevented. Additional characteristics relating to the present invention will become apparent from the description of the present specification and the attached drawings. In addition, the problems, configurations and advantages other than those described above will be clarified by the description of the following example.

BRIEF DESCRIPTION OF DRAWINGS

FIG. 28 is a diagram illustrating an example of a method of forming the groove structure in the immobilizing member.

FIG. 29 is a diagram illustrating an example of the method of forming the groove structure in the immobilizing member.

FIG. 30 is a diagram illustrating an example of the method of forming the groove structure in the immobilizing member.

FIG. 31 is a diagram illustrating an example of the method of forming the groove structure in the immobilizing member.

FIG. 32 is a diagram illustrating an example of the method of forming the groove structure in the immobilizing member.

FIG. 33 is a diagram illustrating an example of a method of forming the groove structure in the nanopore device.

FIG. 34 is a diagram illustrating an example of the method of forming the groove structure in the nanopore device.

FIG. 35 is a diagram illustrating an example of the method of forming the groove structure in the nanopore device.

FIG. 36 is a diagram illustrating an example of the method of forming the groove structure in the nanopore device.

FIG. 37 is a diagram illustrating an example of the method of forming the groove structure in the nanopore device.

FIG. 38 is a diagram illustrating an example of a method of preparing a concave portion and a convex portion of the groove structure made of different materials.

FIG. 39 is a diagram illustrating an example of the method of preparing the concave portion and the convex portion of the groove structure made of different materials.

FIG. 40 is a diagram illustrating an example of the method of preparing the concave portion and the convex portion of the groove structure made of different materials.

DESCRIPTION OF EMBODIMENTS

Figure 1:
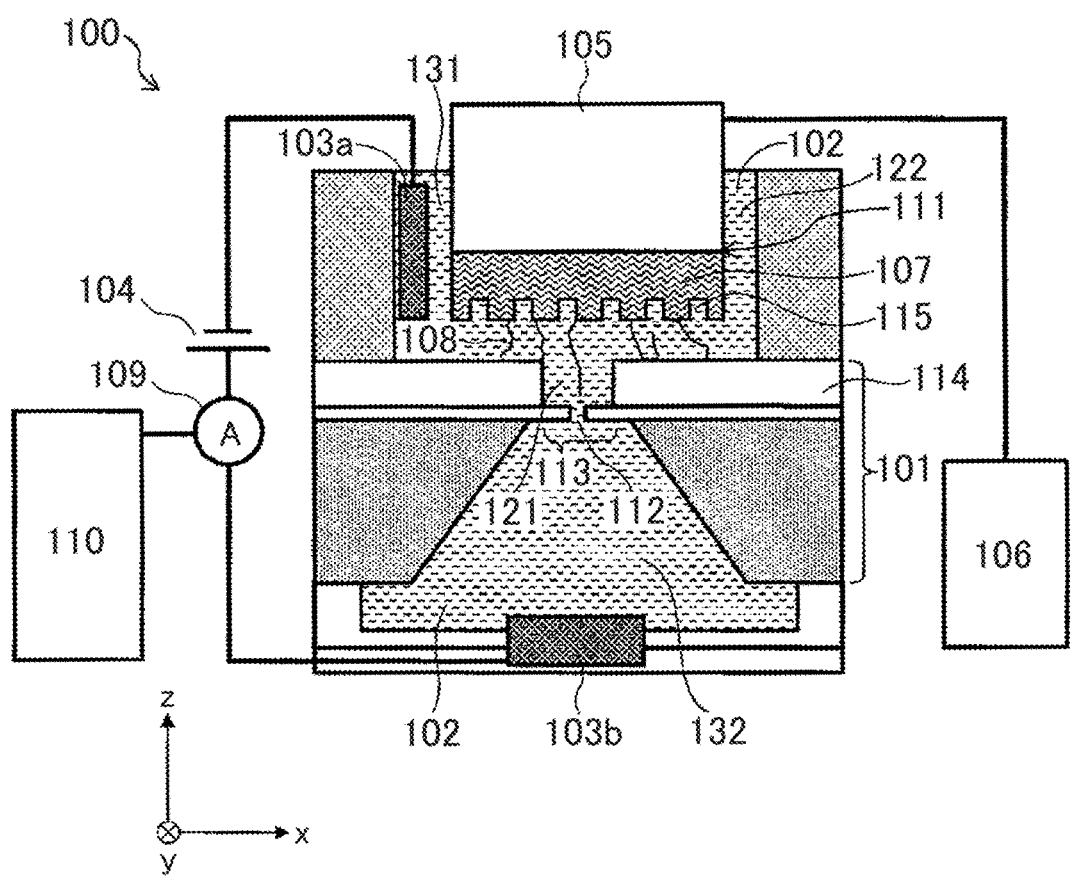
FIG. 1 is a schematic cross-sectional view illustrating a configuration example of a biomolecule measuring device.

Examples of the present invention will now be described with reference to the accompanying drawings. The accompanying drawings show specific examples in accordance with the principles of the present invention, but those drawings are for understanding of the present invention, and should not be used to interpret the present invention in a limited way. The same reference numerals may be given to common configurations in the respective figure.

Hereinafter, embodiments of the present invention will be described with reference to the drawings. A nanopore described in the respective examples is a nano-sized hole penetrating through front and back surfaces provided in a thin film. The thin film is made of, for example, SiN, $SiO_2$, Graphene, Graphite, Si, or the like, but can also be made of an organic substance, a polymeric material, and so on. A nanopore thin film having the nanopore is formed in a part of a nanopore device, and has a structure in which an edge of the nanopore thin film is supported by the nanopore device without provision of support films on upper and lower portions of the nanopore thin film so that the thin film floats in the air. Biomolecules referred to in the present specification include nucleic acids, proteins, amino acids, long chain polymers, and the like.

Example 1

A biomolecule measuring device having a transport control mechanism according to the present invention and an example of sequence reading of the biomolecules using the biomolecule measuring device will be described. FIG. 1 is a schematic cross-sectional view illustrating a configuration example of the biomolecule measuring device.

A biomolecule measuring device 100 according to the present example has two upper and lower liquid tanks 131 and 132 separated by a nanopore device (also referred to as a nanopore substrate) 101. Each of the liquid tanks 131 and 132 is filled with an electrolyte solution 102. The electrolyte solution includes KCl, NaCl, LiCl, CsCl, $MgCl_2$, or the like. In addition, Urea of 4M or more, DMSO, DMF, and NaOH can be mixed in the solution for the purpose of a reduction in a self complementary chain formation of the biomolecules. Also, in order to stabilize the biomolecules, a buffer agent, can be mixed in the solution. The buffer agent includes Tris, EDTA, PBS and the like.

A thin film 113 is formed on the nanopore device 101, and a nanopore 112 is formed at any position in the thin film 113. The two upper and lower liquid tanks 131 and 132 communicate with each other through the nanopore 112 of the thin film 113 supported by the nanopore device 101. Ag/AgCl electrodes 103a and 103b are placed in the two liquid tanks 131 and 132 so as to come into contact with the electrolyte solution 102, and a power supply 104 and an ammeter 109 are connected between the electrodes 103a and 103b. The ammeter 109 is connected to an ADC (not shown) and a PC 110. The PC 110 can record an acquired current value. On the other hand, a driving mechanism 105 is installed in the upper liquid tank 131 and is connected to a driving mechanism control unit 106. A biomolecule immobilizing member (hereinafter simply referred to as an immobilizing member) 107 is coupled to the driving mechanism 105 by a connection member 111. The immobilizing member 107 is larger in size than the thin film 113 in a plan view. Biomolecules 108 are immobilized on a flat lower surface of the immobilizing member 107.

When the immobilizing member 107 comes into contact with the thin film 113 in which the nanopore 112 is provided, the thin film 113 may be destroyed. For that reason, a stop mechanism is provided to prevent a contact between the immobilizing member 107 and the thin film 113 when the immobilizing member 107 driven by the driving mechanism 105 descends toward the nanopore device 101. The stop mechanism according to the present example is configured by a space providing member 114 that surrounds a periphery of the nanopore device 101 outside the thin film 113 like a bank and provides a space between the immobilizing member 107 and the thin film 113. The thin film 113 having the nanopore 112 is placed in a circular space provided at the center of the space providing member 114. A dimension of the thin film 113 in the plan view is smaller than the dimension of the immobilizing member 107. Therefore, the immobilizing member 107 moving toward the nanopore device 101 collides with the space providing member 114 and stops before coming into contact with the thin film 113. As a result, the thin film 113 is not destroyed by the contact of the immobilizing member 107 with the thin film 113.

Since the dimension of the thin film 113 are required to provide an area making it difficult that two or more holes are provided at the time of providing the hole by a thin film strength and voltage application, it is preferable that a length of one side (a side length if the thin film 113 is rectangular, and a diameter if the thin film 113 is circular) may be about 100 to 500 nm. In order to attain DNA single base resolution, the thickness capable of providing the nanopore 112 having an effective film thickness equivalent to one base is suitably about 1 nm. The thickness of the space providing member 114 is suitably about 200 to 500 nm in consideration of maintaining strength of the thin film 113 and considering a fluctuation of an immobilized height of the biomolecules on the surface of the immobilizing member 107. In the present example, the dimension of the thin film 113 is 500 nm in diameter and the film thickness of the space providing member 114 is 250 nm.

In a blockage current measurement method, base species configuring the DNA are identified according to a resistance change when the DNA passes through the nanopore 112. It is assumed that a signal change obtained at that time is rectangular.

Figure 2:
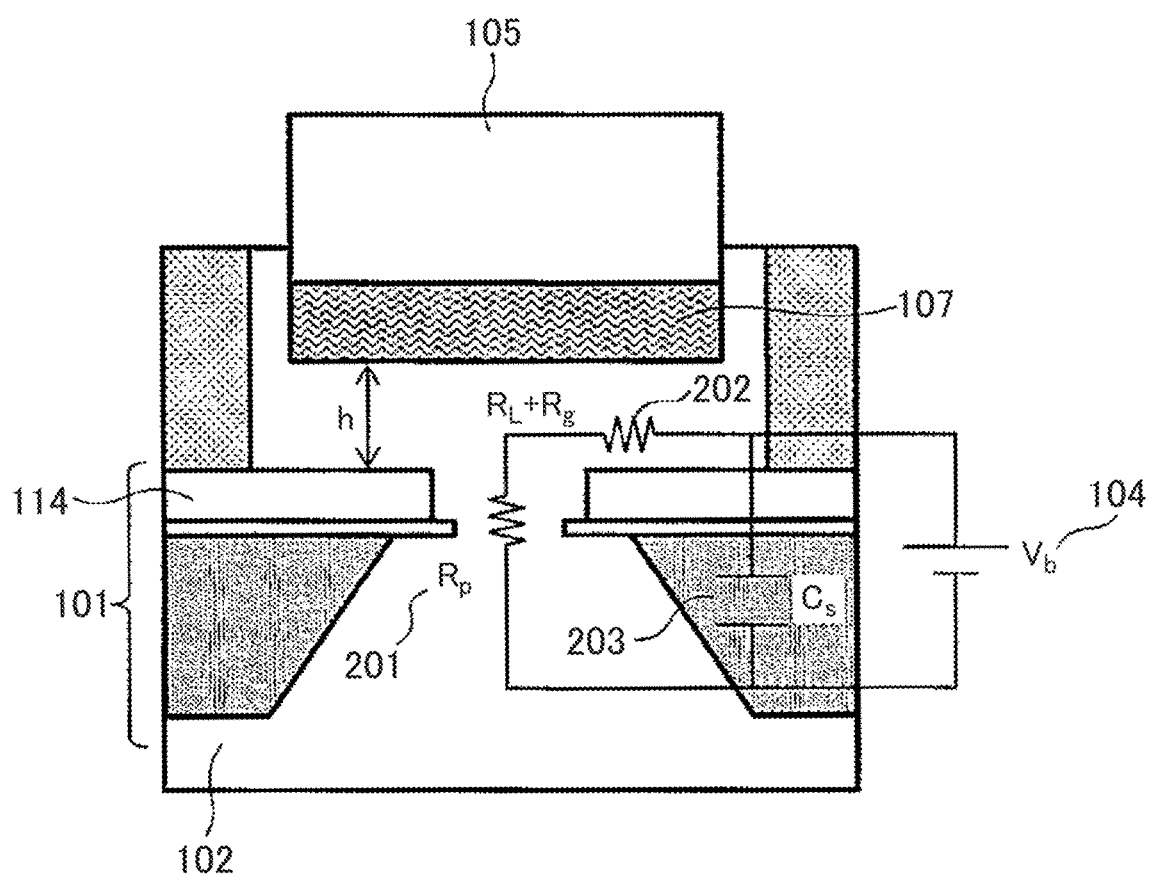
FIG. 2 is an illustrative diagram of an equivalent circuit of a nanopore device and a peripheral mechanism.

FIG. 2 shows an equivalent circuit of the nanopore device and a surrounding environment of the nanopore device. In FIG. 2, reference numeral 201 is a pore resistance $R_p$, 202 is a combined resistance $(R_L+R_g)$ of a solution resistance and a passage resistance, and 203 is a nanopore device capacity $C_s$.

A time constant of a signal in a system shown in the figure is expressed as follows.

$$\tau=(R_L+R_g)C_s$$

In the above expression, $R_g=L/\sigma Wh$ is satisfied.

Figure 3:
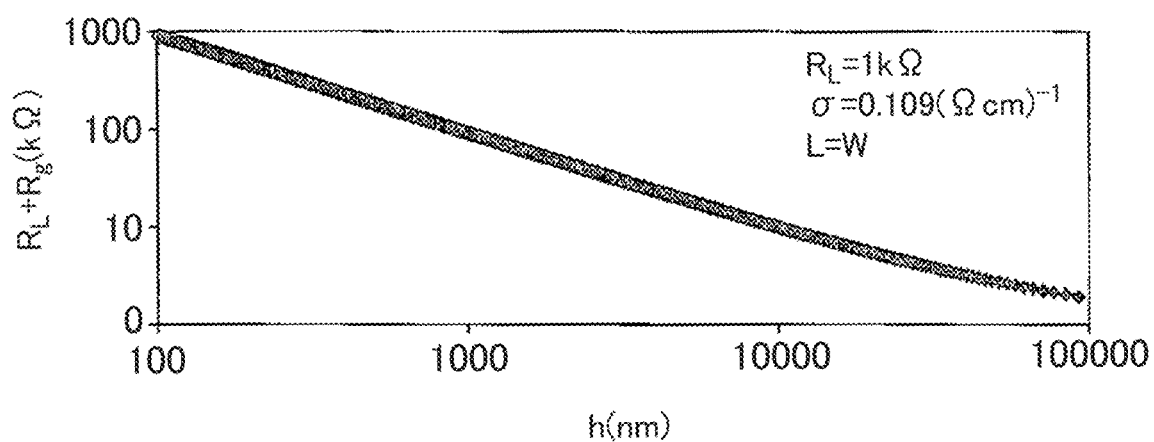
FIG. 3 is a graph showing a relationship between a distance between an immobilizing member and the nanopore device and a relationship between a solution resistance and a passage resistance.
Figure 4:
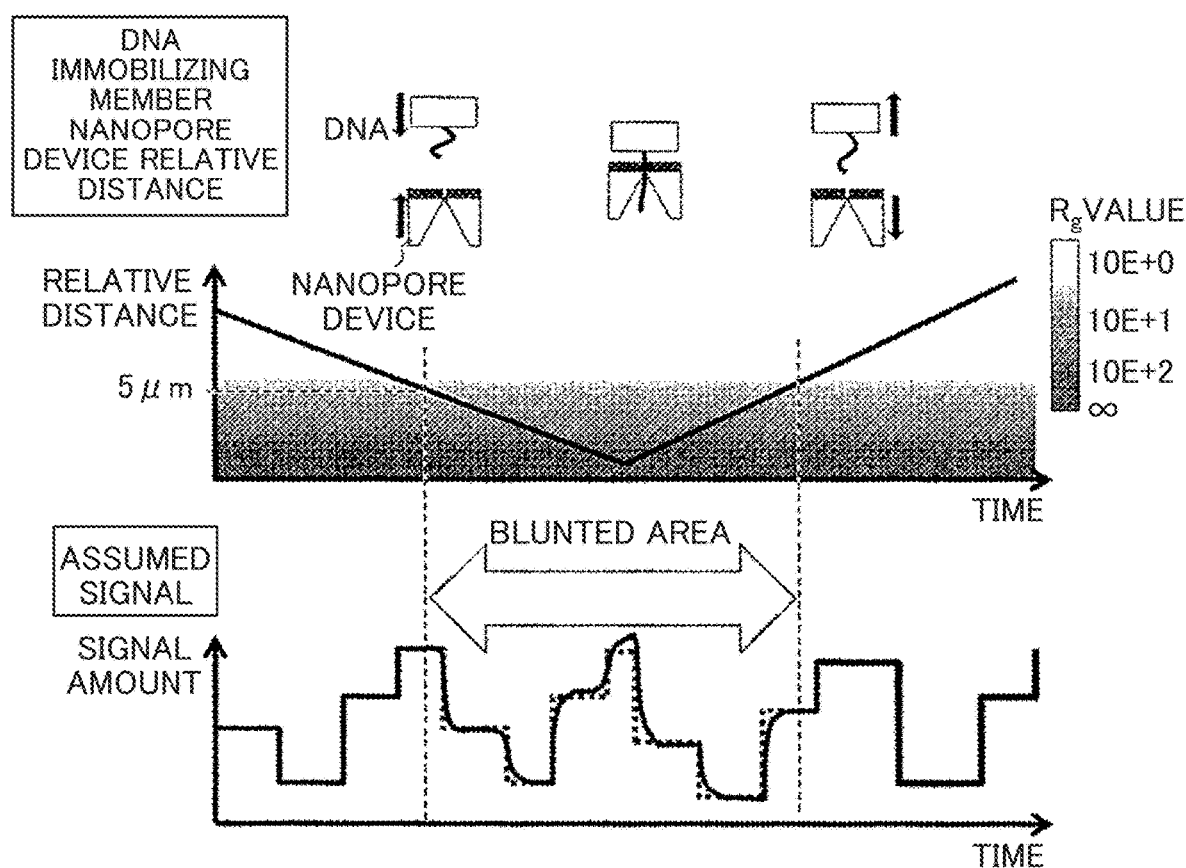
FIG. 4 shows a signal schematic diagram when the immobilizing member is brought close to the nanopore device and thereafter the immobilizing member is separated from the nanopore device.

When the immobilizing member 107 comes closer to the nanopore device 101, since a value of h decreases, the solution resistance rises. FIG. 3 shows a relationship between h and a resistance $(R_L+R_g)$ when L=W is met for simplification. It can be understood that when a distance between the immobilizing member 107 and the nanopore device 101 reaches 300 nm, a total solution resistance rises from 2 digits to 3 digits. For that reason, as shown in FIG.

4, when the immobilizing member 107 and the nanopore device 101 come closest to each other, the signal is blunted.

A time constant of the signal is required to be 10 μs or less from a relationship between a nanopore passage speed of the DNA and a response speed of a detector. In other words, it is required that when a substrate capacitance Cs is 600 μF, $R_g$ is 100 kΩ.

Hereinafter, a configuration for reducing an increase in the resistance described above will be described. In order to reduce the increase in resistance, at least one of the nanopore device 101 and the immobilizing member 107 has a groove structure in a range where the nanopore device 101 and the immobilizing member 107 are opposed to each other.

In this example, the groove structure is required to come into contact with the electrolyte solution 102, and is formed in a region where the nanopore device 101 and the immobilizing member 107 are opposed to each other in the electrolyte solution. A groove may be formed in a concavo-convex structure, or may be formed with a hole structure penetrating through the immobilizing member 107.

Figure 5:
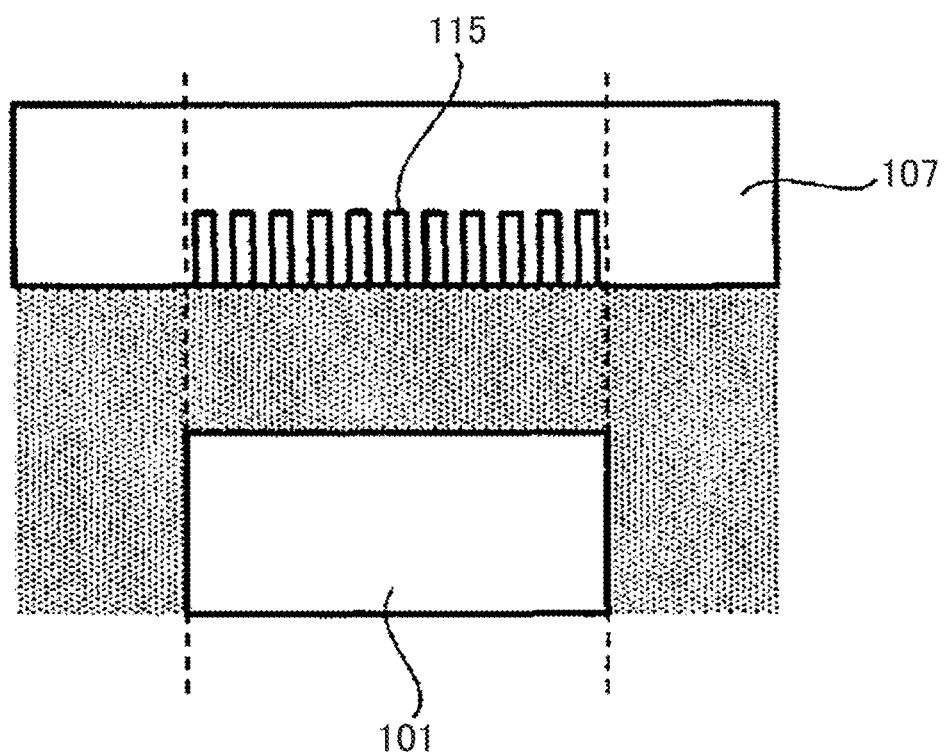
FIG. 5 is a diagram illustrating a range in which a groove is provided.
Figure 6:
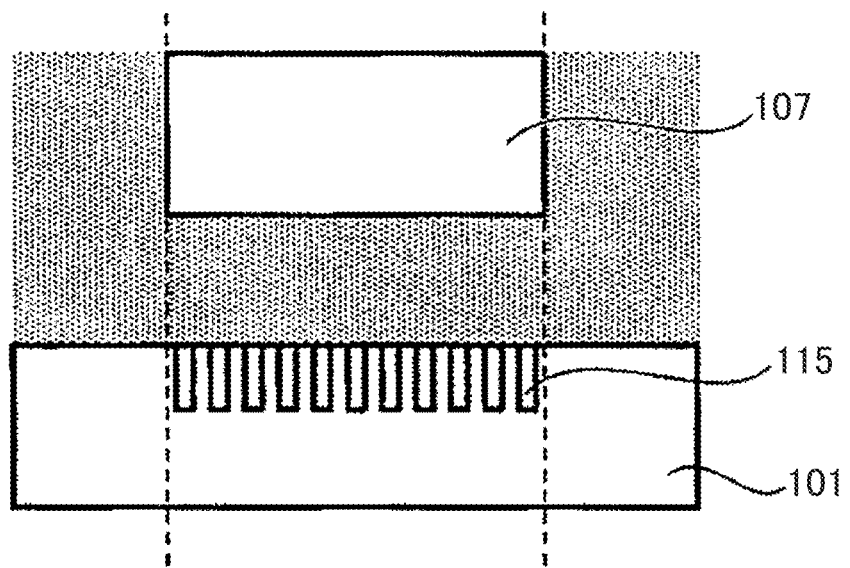
FIG. 6 is a diagram illustrating a range in which the groove is provided.

FIGS. 5 and 6 are diagrams illustrating the range in which the grooves are provided in more detail. The multiple grooves 115 are provided in a range where the nanopore device 101 and the immobilizing member 107 are opposed to each other (a range indicated by dotted lines in FIGS. 5 and 6). FIG. 5 shows an example in which the multiple grooves 115 are provided only in the immobilizing member 107. When the grooves 115 are provided only in the immobilizing member 107, a manufacturing method can be simplified, and the cost can be reduced as compared with a case where the grooves 115 are provided in the nanopore device 101. FIG. 6 shows an example in which the multiple grooves 115 are provided only in the nanopore device 101.

When the nanopore device 101 completely comes into contact with the immobilizing member 107, a surrounding space (for example, a space 121 in FIG. 1) of the nanopore 112 and a space (for example, a space 122 on a surface side of the immobilizing member 107 side in FIG. 1) in a region where the nanopore device 101 and the immobilizing member 107 are not opposed to each other are required to come into electric contact with each other. As long as the above requirements are satisfied, the groove structure need not be formed continuously. This configuration will be described with reference to the following examples.

Figure 7:
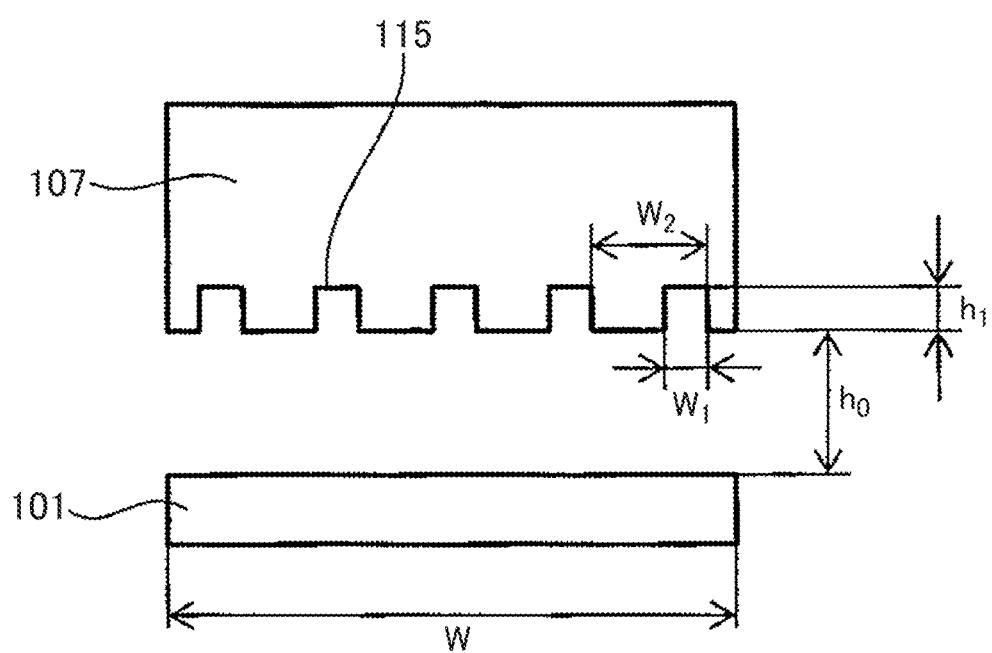
FIG. 7 is a diagram illustrating an example of a configuration in which a driving mechanism stops the immobilizing member at a position slightly above the nanopore device.
Figure 8:
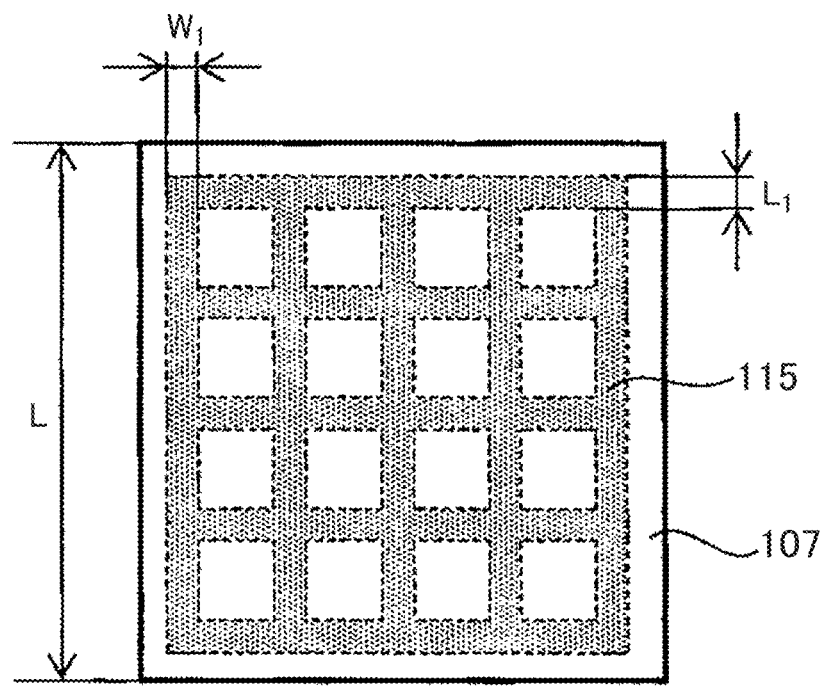
FIG. 8 is a plan view of an immobilizing member in the case of a configuration of FIG. 7.

FIG. 7 shows an example of a configuration in which the immobilizing member 107 is stopped at a position slightly above the nanopore device 101 when the immobilizing member 107 descends toward the nanopore device 101. FIG. 8 is a plan view of the immobilizing member 107 in the case of the configuration in FIG. 7. As shown in FIG. 7, the driving mechanism 105 controls the immobilizing member 107 so as to stop at the position slightly above the nanopore device 101 (a relative distance between the immobilizing member 107 and the nanopore device 101 is not 0). In the configuration described above, the grooves 115 are not required to extend so as to reach an edge of the immobilizing member 107 (FIG. 8). In other words, the grooves 115 are not required to be continuously provided over an entire area in which the device 101 and the immobilizing member 107 are opposed to each other. In that case, a region in which the grooves 115 are partially provided may be present in the range where the nanopore device 101 and the immobilizing member 107 are opposed to each other.

Figure 9:
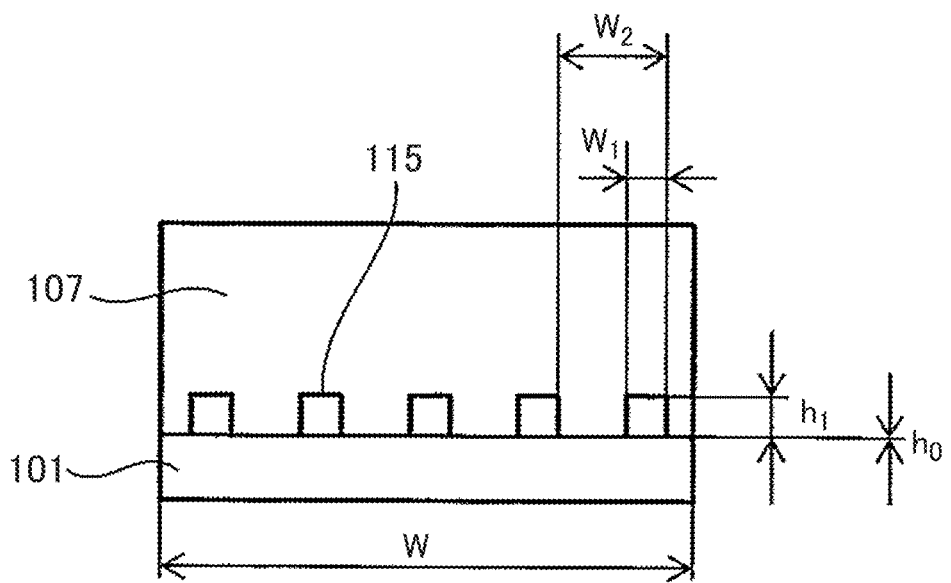
FIG. 9 is a diagram showing an example of a configuration in which the driving mechanism, brings the immobilizing member into contact with the nanopore device.
Figure 10:
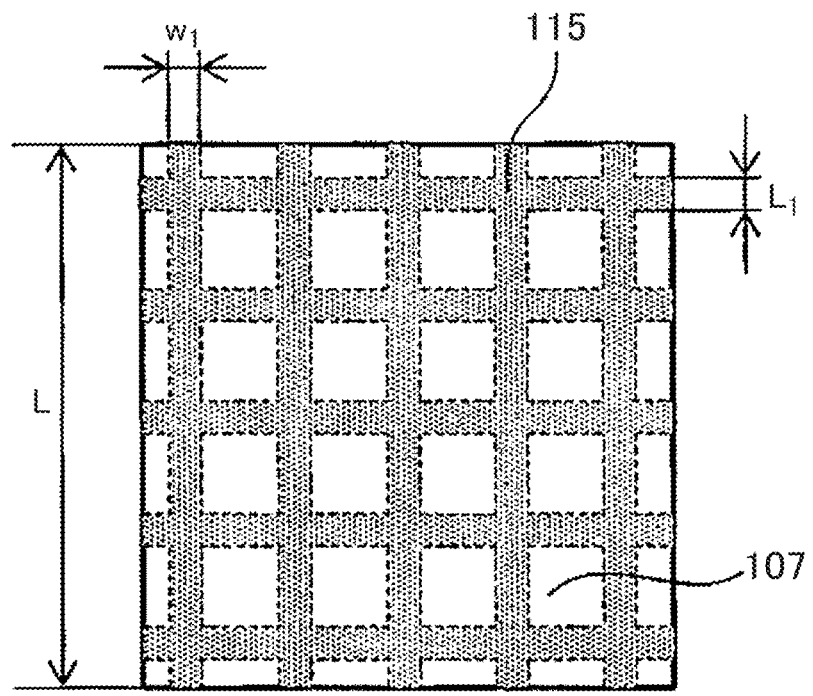
FIG. 10 is a plan view of the immobilizing member in the case of the configuration of FIG. 9.

FIG. 9 shows an example of a configuration in which the immobilizing member 107 comes into contact with the nanopore device 101 when the immobilizing member 107 descends toward the nanopore device 101. FIG. 10 is a plan view of the immobilizing member 107 in the case of the configuration of FIG. 9. As shown in FIG. 9, when the driving mechanism 105 lowers the immobilizing member 107 toward the nanopore device 101, the immobilizing member 107 completely comes into contact with the nanopore device 101 (a relative distance between the immobilizing member 107 and the nanopore device 101 is 0). In such a configuration, in order to satisfy the above requirement, the grooves 115 are required to extend so as to reach an edge of the immobilizing member 107 (that is, an end of the range in which the nanopore device 101 and the immobilizing member 107 are opposed to each other) (FIG. 10). In other words, the grooves 115 are provided continuously over the entire area in which the nanopore device 101 and the immobilizing member 107 are opposed to each other.

Figure 11:
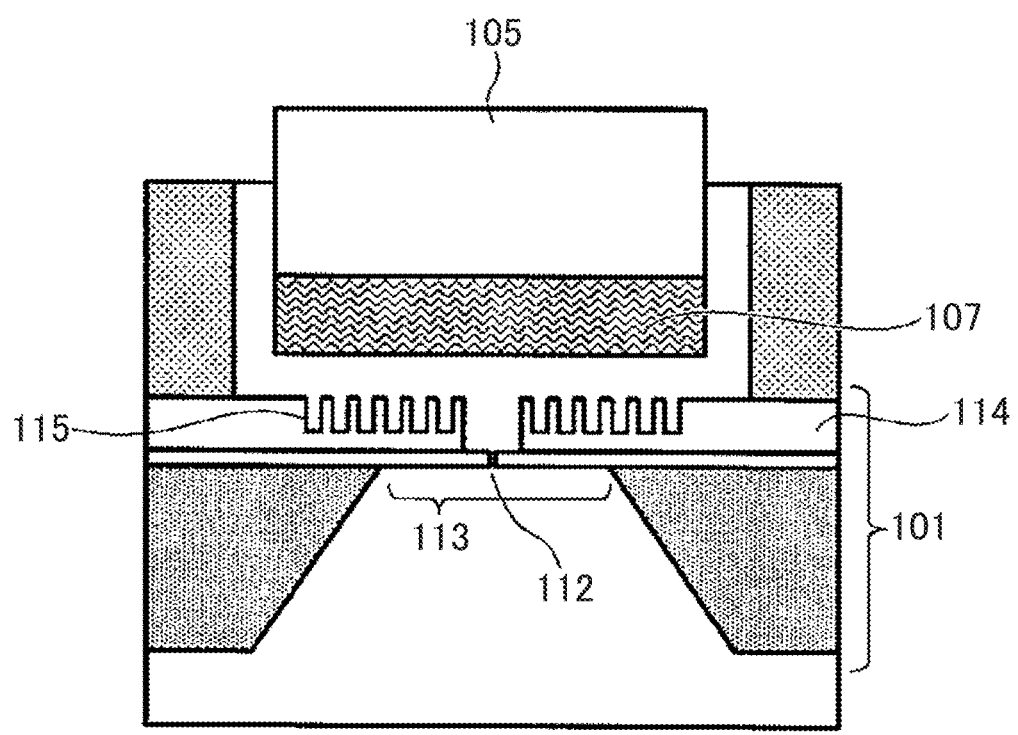
FIG. 11 is an example of a groove structure.
Figure 12:
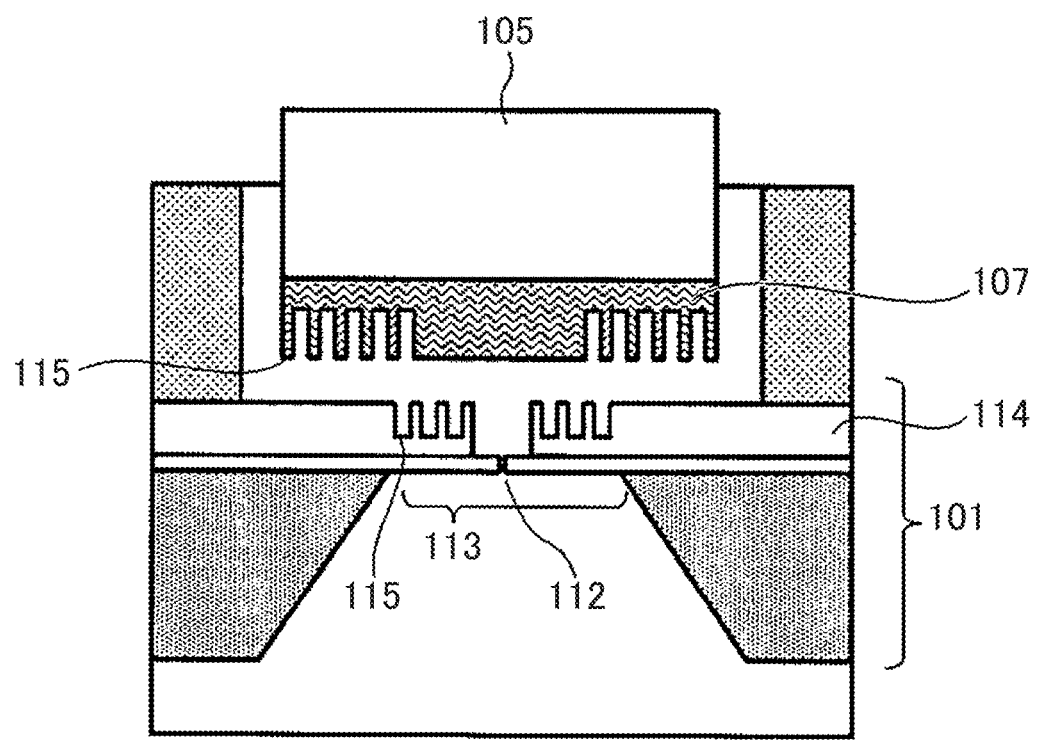
FIG. 12 is an example of a groove structure.
Figure 13:
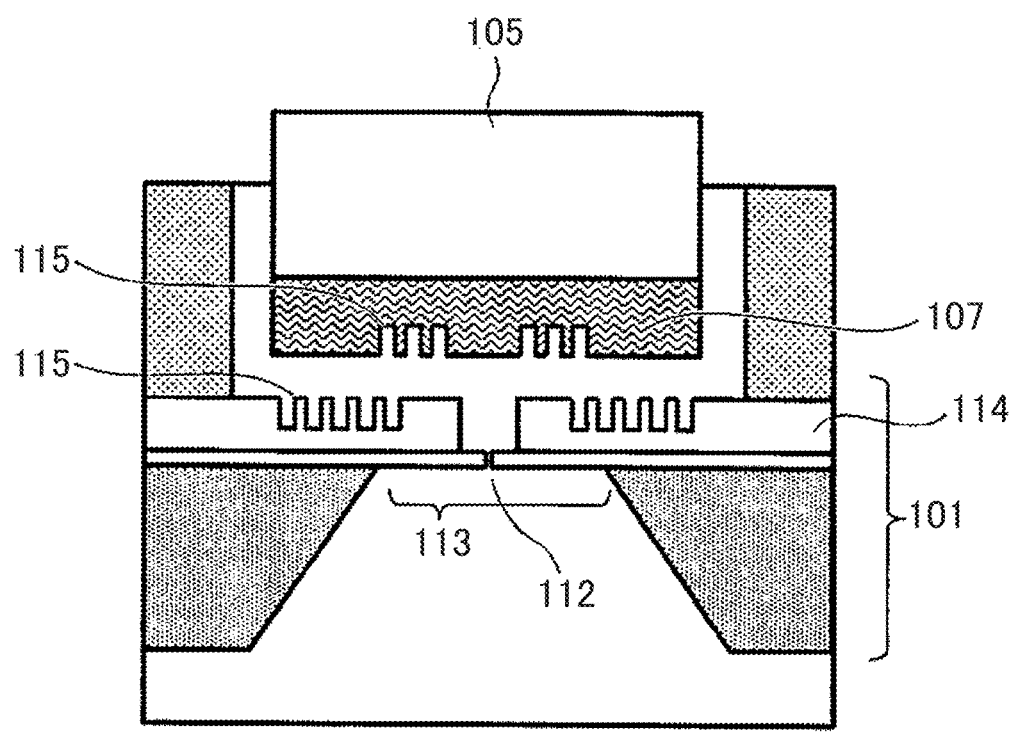
FIG. 13 is an example of a groove structure.

FIGS. 11, 12, and 13 show examples of the groove structure. The groove structure may be continuously formed in the range in which the nanopore device 101 and the immobilizing member 107 are opposed, to each other. In the example of FIG. 11, the multiple grooves 115 are provided only in the space providing member 114 of the nanopore device 101.

It should be noted that the groove structure may be formed in both of the nanopore device 101 and the immobilizing member 107. In the example of FIG. 12, an outer peripheral portion of the immobilizing member 107 has the multiple grooves 115, and a peripheral portion of the nanopore 112 in the space providing member 114 of the nanopore device 101 has the multiple grooves 115. In this way, the multiple grooves 115 may be continuously provided between the upper immobilizing member 107 and the lower nanopore device 101 in the range where the nanopore device 101 and the immobilizing member 107 are opposed to each other.

In the example of FIG. 13, the immobilizing member 107 has the multiple grooves 115 in a region around the nanopore 112, and the nanopore device 101 has the multiple grooves 115 outside that region.

Figure 14:
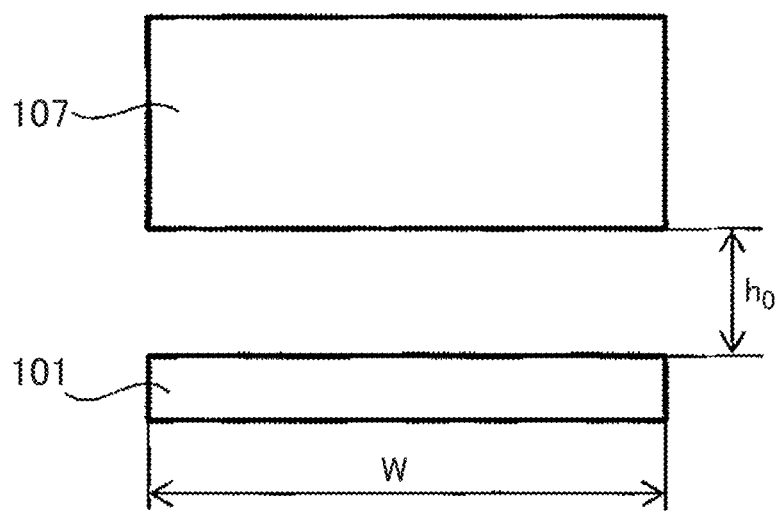
FIG. 14 is a diagram illustrating a passage resistance R in a conventional configuration in which no groove structure is formed.
Figure 15:
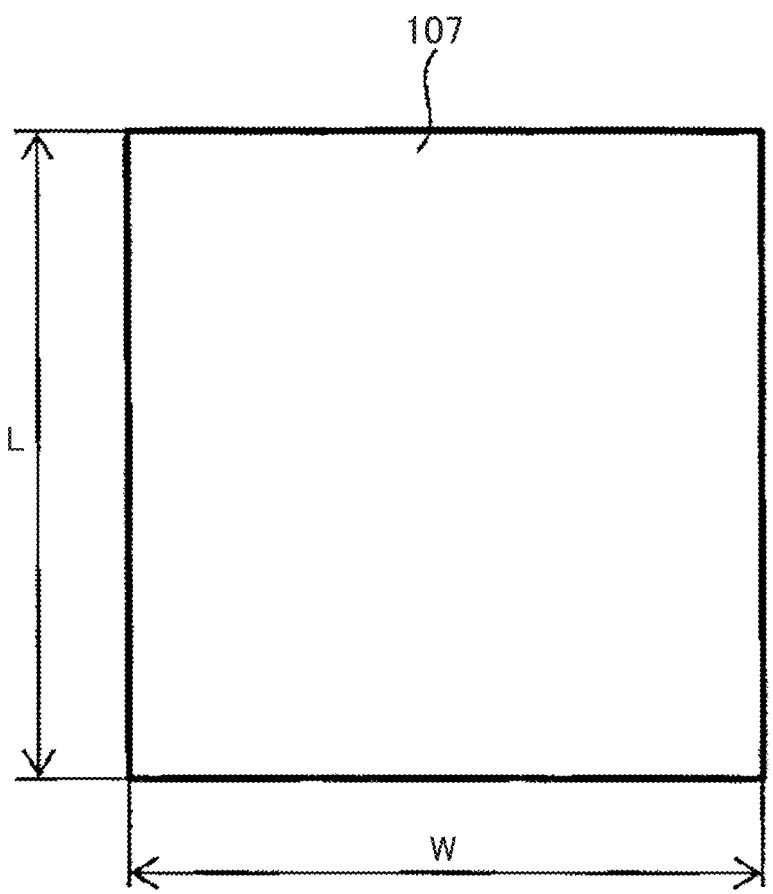
FIG. 15 is a diagram illustrating a passage resistance R in a conventional configuration in which no groove structure is formed.
Figure 16:
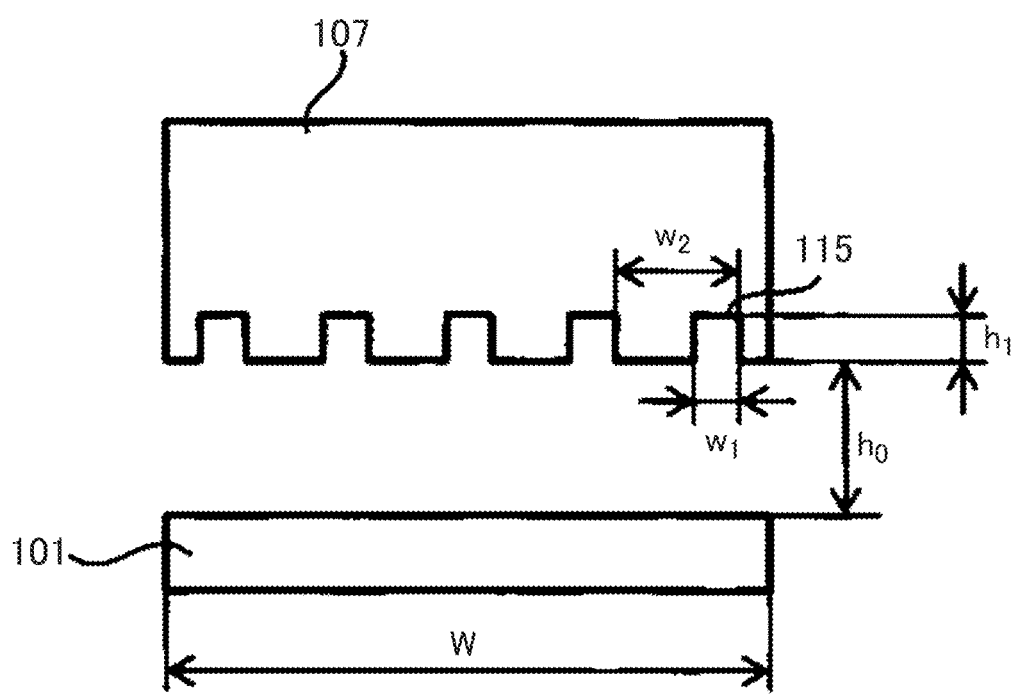
FIG. 16 is a diagram illustrating the passage resistance in a configuration having the groove structure.
Figure 17:
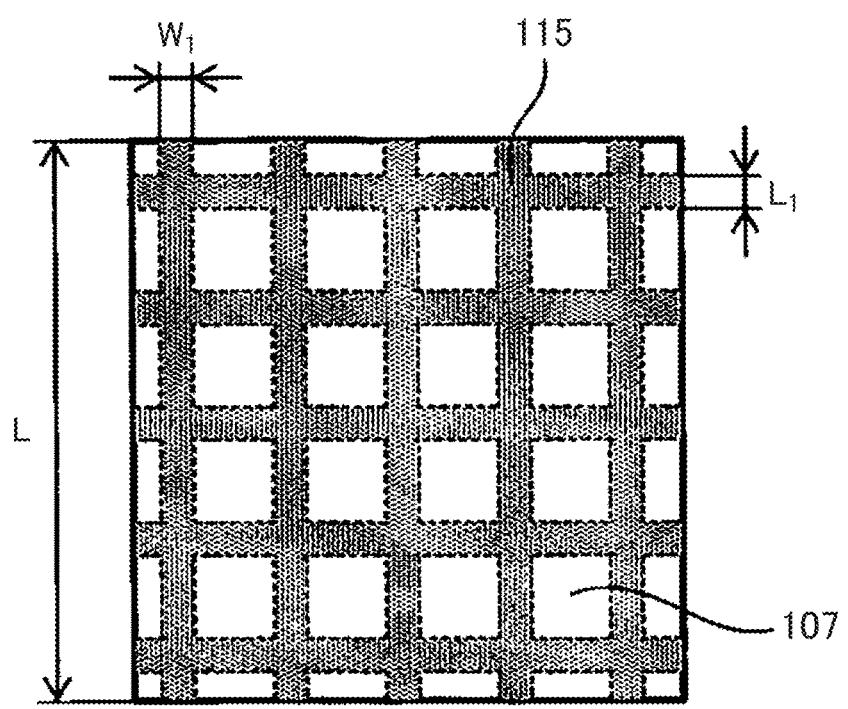
FIG. 17 is a diagram illustrating the passage resistance in a configuration having the groove structure.

A dimension of the grooves 115 will be described. FIGS. 14 and 15 are diagrams illustrating the passage resistance R in a conventional configuration in which no groove structure is formed. On the other hand, FIGS. 16 and 17 are diagrams illustrating a passage resistance $R_1$ in a configuration having the groove structure according to the present example.

When the respective dimensions of the groove structure are defined by FIGS. 16 and 17, $R_1$ is expressed as follows.

$$R_1 = (L - nL_1)/(Wh_0 + w_1 h_1 n)$$

Figure 18:
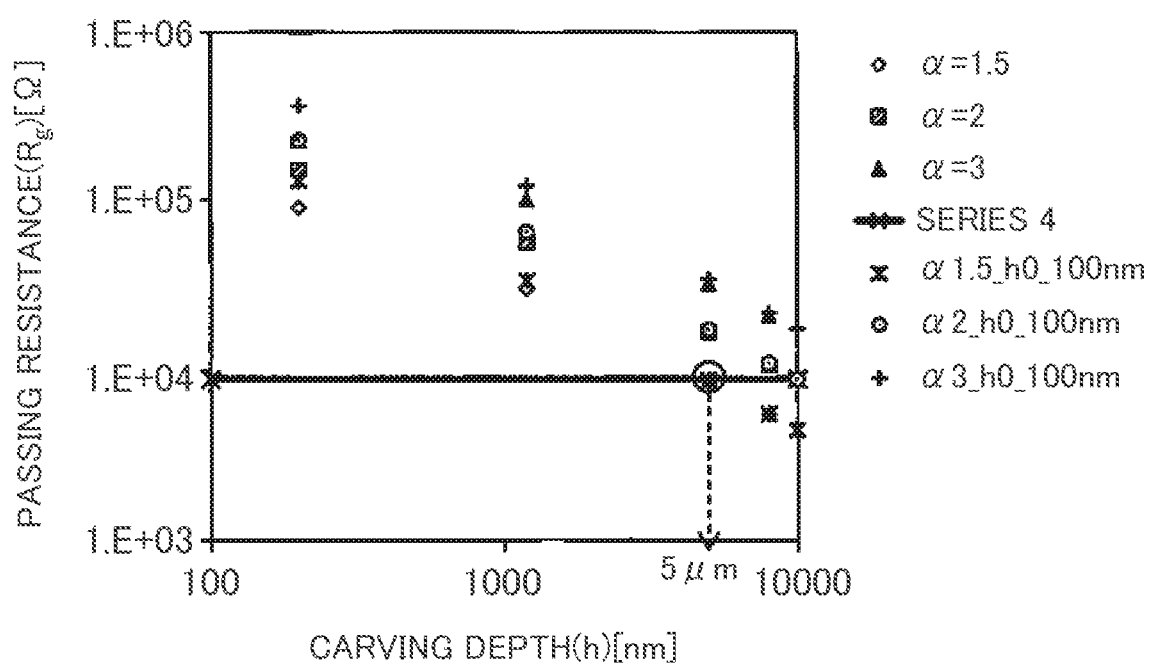
FIG. 18 is a graph showing a relationship between a groove depth and a solution resistance when a relationship between a groove width and a groove pitch is changed.

FIG. 18 is a graph, showing a relationship between a groove depth and the solution resistance when a relationship between a groove width and a groove pitch is changed. In this example, α is a ratio of $w_1$ and $w_2$, and $w_1 = \alpha \times w_2$ is met. As shown in the graph, the solution resistance is measured when h0=0 for three α values (α=1.5, 2, and 3). Also, in the graph, the notation "h0_100 nm" is h0=100 nm. In this example, the solution resistance when h0=100 nm is met is measured for three α values. In addition, "series 4" is a target value of solution resistance.

For example, in the configuration of $w_1$–$1.5 \times w_2$, a target value can be achieved when an engraving depth of the grooves 115 is about 5 μm. For example, it is preferable that the engraving depth of the grooves 115 is 5 μm or more.

A total volume of a gap between the nanopore device 101 and the immobilizing member 107 caused by provision of the grooves 115 when the immobilizing member 107 is brought closest to the nanopore device 101 can have only to sufficiently contribute to a reduction in the solution resistance. Therefore, if the total volume of the gap can sufficiently contribute to the reduction in the solution resistance, the pitch (corresponding to $w_2$ described above) and the width (corresponding to $w_1$ described above) of the grooves 115 do not need to be uniform over the entire portion where the grooves 115 are provided.

Figure 21:
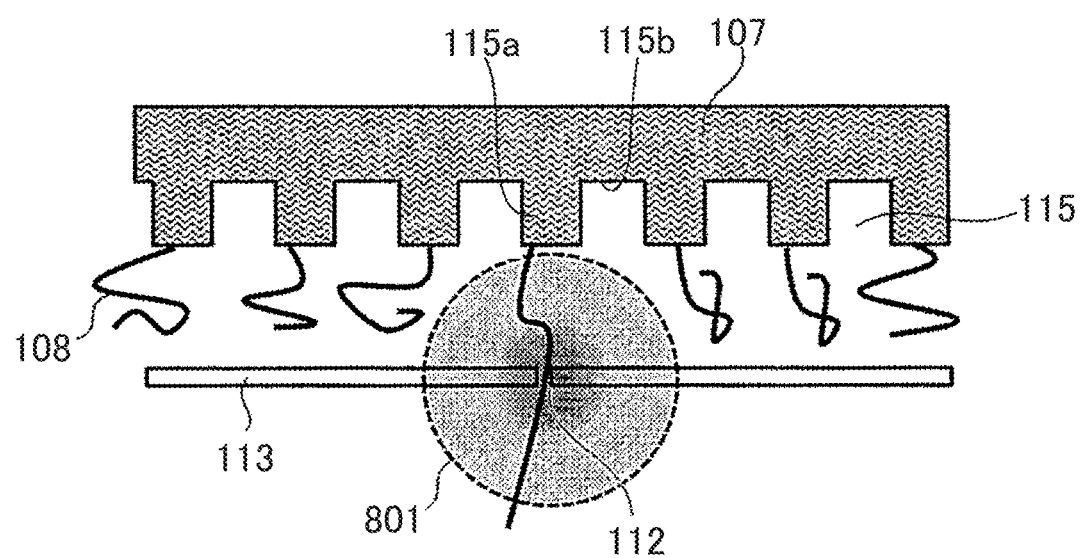
FIG. 21 is a diagram illustrating a configuration of the groove when there is no positioning mechanism between the groove and the nanopore device.

Next, a method of immobilizing the biomolecules 108 (for example, DNA) will be described. FIG. 21 is an enlarged view of the vicinity of the nanopore in the case where the immobilizing member has the grooves. Convex portions 115a and concave portions 115b are formed in a portion where the grooves 115 are provided. Since the DNA is immobilized on the convex portions 115a, a width of the convex portions 115a is required to have a size equal to or larger than the DNA immobilizing pitch. It is conceivable that the DNA immobilizing pitch is a 100 nm interval from the viewpoint of a nature of the DNA. Therefore, for example, it is desirable that the width of the convex portions of the portion where the grooves 115 is set to 100 nm or more.

Figure 22:
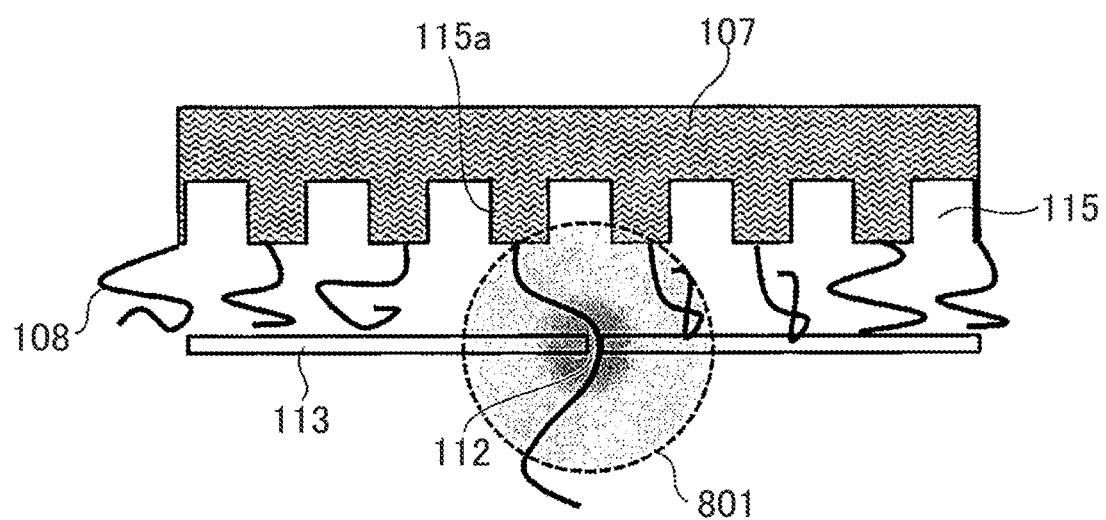
FIG. 22 is a diagram illustrating a configuration of the groove when there is no positioning mechanism between the groove and the nanopore device.

In this example, it is assumed that there is no positioning mechanism between the grooves 115 and the nanopore device 101. As shown in FIG. 21, the DNA on the immobilizing member 107 is required to be attracted by a potential gradient 801 generated in the vicinity of the nanopore 112 irrespective of a positional relationship between the nanopore 112 and the convex portions 115a of the grooves 115. It is therefore necessary that the pitch of the grooves 115 (corresponding to $w_2$ described above) is 300 nm or less, FIGS. 21 and 22 are examples in which the pitch of the grooves 115 is 300 nm or less. In FIG. 21, since one convex portion 115a of the grooves 115 is placed directly above the nanopore 112, the DNA is attracted by the potential gradient 801. Also, even in the case where the convex portion 115a of the grooves 115 is not placed directly above the nanopore 112 as shown in FIG. 22, since the pitch of the grooves 115 is 300 nm or less, the DNA can be attracted by the potential gradient 801.

Figure 23:
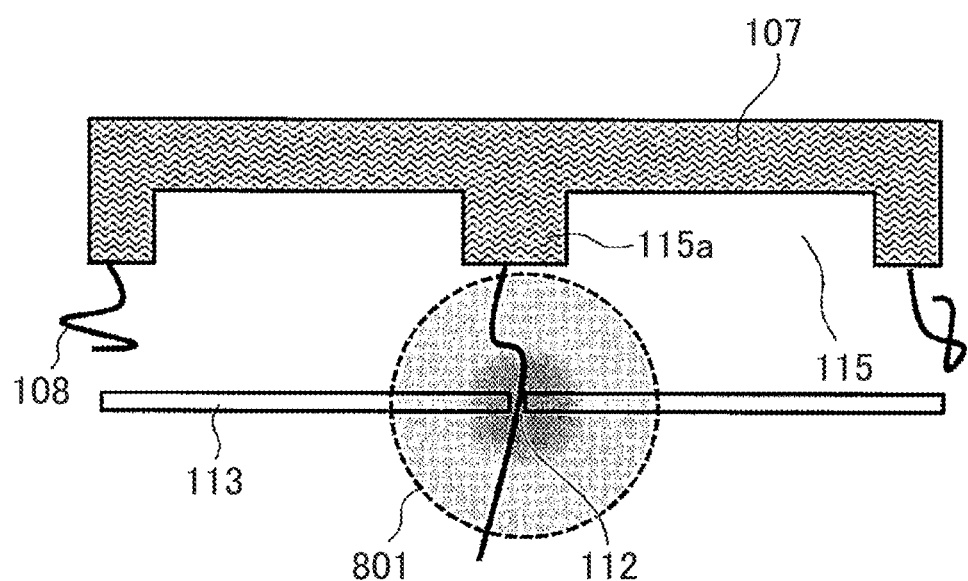
FIG. 23 is a diagram illustrating a configuration of the groove when there is a positioning mechanism between the groove and the nanopore device.
Figure 24:
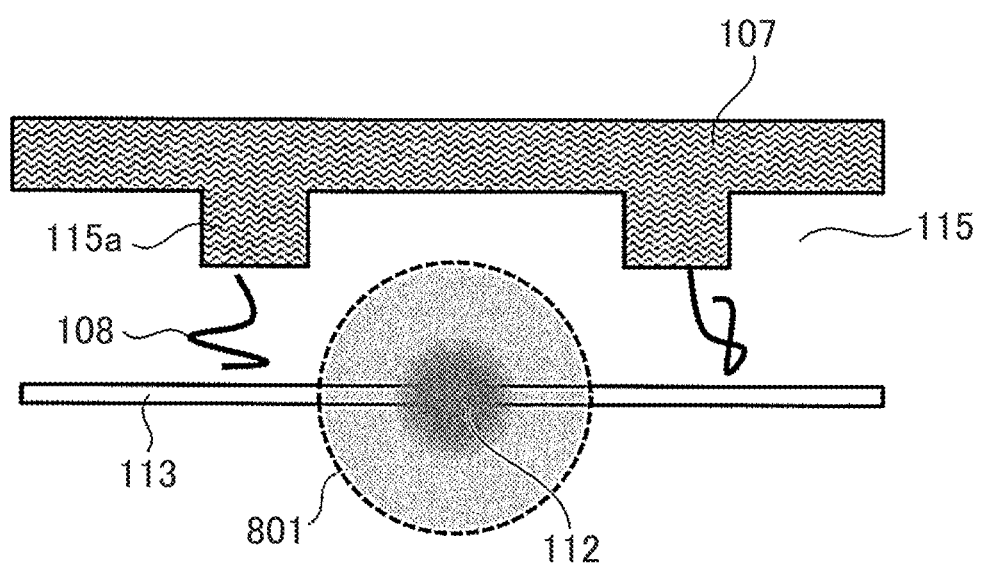
FIG. 24 is a view for explaining a configuration of the groove when there is the positioning mechanism between the groove and the nanopore device.

Next, it is assumed that there is a positioning mechanism between the grooves 115 and the nanopore device 101. In that, case, even when the pitch of the grooves 115 (corresponding to $w_2$ described above) is 300 nm or more, the introduction of the DNA into the nanopore 112 can be achieved. FIGS. 23 and 24 show examples in which the pitch of the grooves 115 is larger than 300 nm. As shown in FIG. 24, when any convex portion 115a of the groove 115 is not placed directly above the nanopore 112, no DNA cannot be attracted by the potential gradient 801. When there is the positioning mechanism, as shown in FIG. 23, the immobilizing member 107 is moved in a direction parallel to a surface of the thin film 113 whereby any convex portion 115a of the grooves 115 can be placed directly above the nanopore 112. Incidentally, the positioning mechanism between the grooves 115 and the nanopore device 101 will be described, in an example to be described below.

Figure 80:
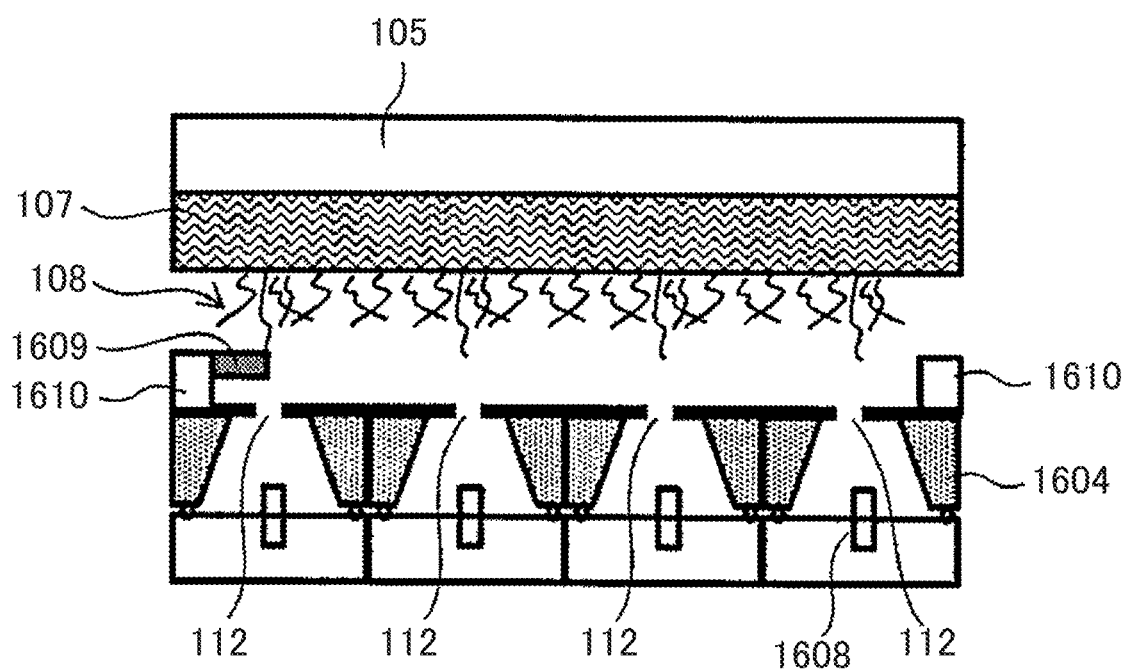
FIG. 80 is a schematic cross-sectional view illustrating a first example of a biomolecule measuring device having parallelized nanopore devices.

Although the space defining member 114 can be formed in an arbitrary shape, if the convex portions are formed on the nanopore device 101 without the configuration shown in FIG. 1, there is a limitation described above (for example, a case of the space defining member in FIG. 80, or the like). In the case where the width of the grooves 115 (corresponding to $w_1$ described, above) is formed, with a dimension exceeding the width of the space defining member, when the immobilizing member 107 is brought into complete contact with the nanopore device 101, a high resistance area can be produced. Therefore, there is a need to avoid the complete contact between the immobilizing member 107 and the nanopore device 101 or to limit the width of the grooves 115 to be equal to or less than the width of the space defining member.

Figure 25:
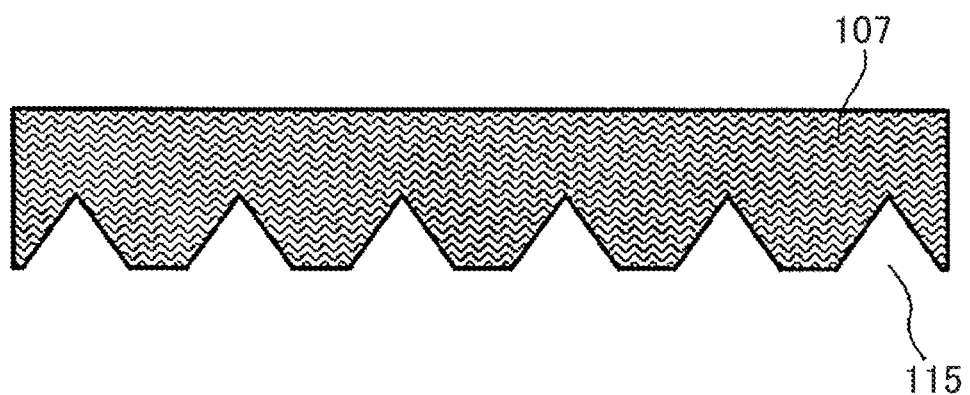
FIG. 25 is a diagram illustrating an example of an immobilizing member having a groove structure.
Figure 26:
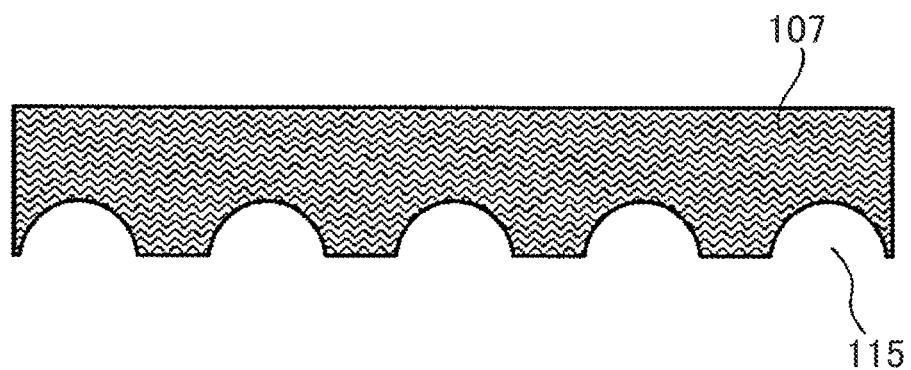
FIG. 26 is a diagram illustrating an example of the immobilizing member having the groove structure.
Figure 27:
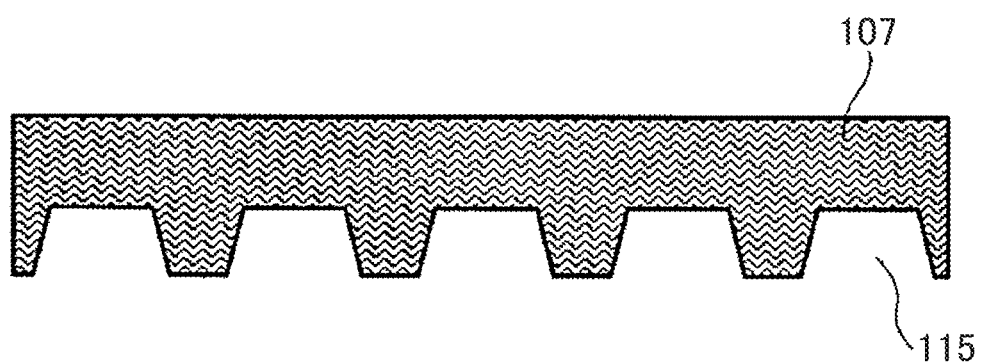
FIG. 27 is a diagram illustrating an example of the immobilizing member having the groove structure.

FIGS. 25 to 27 show examples of the immobilizing member having the groove structure. A cross section of the groove structure may be a triangle, a semicircle, or a trapezoid as well as the rectangle shown in FIG. 1.

Next, a method of forming the groove structure in the immobilizing member 107 will be described with reference to FIGS. 28 to 32. First, a silicon substrate 107 to be an immobilizing member is prepared (FIG. 28). Then, a resist 1101 is coated on the silicon substrate 107 (FIG. 29). Next, the resist 1101 is patterned with a target dimension (FIG. 30). Then, the silicon substrate 107 is scraped by dry etching to provide the grooves 115 (FIG. 31). The resist 1101 on the silicon substrate 107 is removed (FIG. 32). Alternatively, the silicon substrate 107 may be processed by a dicing blade without using a resist or the like to provide the grooves 115. In this example, the concave portions and the convex portions of the groove structure are made of the same material.

Next, a method of providing the groove structure in the nanopore device will be described with reference to FIGS. 33 to 37. It is preferable that a process of providing the grooves 115 is incorporated in a process of manufacturing the nanopore device 101. A silicon substrate 3301 that serves as a substrate of the nanopore device 1010 is prepared (FIG. 33). A nitride film, an oxide film, and a nitride film are formed over the silicon substrate 3301, a nitride film is formed over a back surface of the silicon substrate 3301, and the resist 1101 is coated on an uppermost surface of the silicon substrate 3301 on the back surface of which the nitride film has been formed (FIG. 34).

Then, the resist 1101 is patterned with a target dimension (FIG. 35). First, patterning for thin film opening and patterning for silicon etching are performed. Since the positions of the thin film 113 and the nanopore 112 are specified, by the pattern, patterning for the groove structure is performed on the resist 1101 with the above pattern as a marker. In another example, in order to create the groove structure, scraping with a dicing blade may be performed. A front surface and a back surface of the resist 1101 are etched according to a created pattern (FIG. 36). The resist 1101 can be finally removed and the grooves 115 can be provided in the nanopore device 101 (FIG. 37).

Then, a method of preparing the concave portions and the convex portions of the groove structure with different materials will be described with reference to FIGS. 38 to 40. The concave portions and the convex portions of the groove structure are prepared with different materials, thereby being capable of dividing the immobilizing member 107 into a region in which the biomolecules 108 are immobilized and a region in which the biomolecules 108 are not immobilized.

The present example is basically the same as the method described in FIGS. 28 to 32 except that two films are formed before processing for grooves is performed. First, a silicon substrate 107 that serves as the immobilizing member is prepared (FIG. 38). Then, a first film 1302, which is not likely to be bound to the biomolecules 108, is formed on the silicon substrate 107, and thereafter a second film 1301, which is likely to be bound to the biomolecules 108 (FIG. 39). Then, the second film 1301 is etched (FIG. 40). It should be noted that at the time of etching, a gas species is selected so that an etch stop occurs in the first film 1302.

In the above example, a polySi film may be used as the first film. In addition, gold, nickel, titanium, or the like may be used as the second film. In that case, a configuration in which APTES is formed on a Si film, but is not bound to a metal portion can be applied.

The biomolecules 108 (for example, DNA) can be bound to the entire surface of the immobilizing member 107 described above, but the material of the groove structure can be selected as described above. A fact that the material of the groove structure is selected, and the DNA can be immobilized only to the convex portions of the grooves 115 (that is, the second film 1301 described above) is effective not only to increase the reliability of the signal but also to read the DNA for a longer time.

As described with reference to FIGS. 38 to 40, a material to which the target biomolecules 108 cannot be immobilized is formed as a first layer on the silicon substrate, and a material to which the biomolecules 108 can be immobilized is formed as a second layer on the first layer. Thereafter, the grooves 115 are provided in the second layer. In this situation, etching is performed with the use of gases having different etch rates between the second layer and the first layer. As another example, a third film may be formed between the first layer and the second layer, and the third film may be used as a role of an etching stop. Finally, the third film is removed with an etchant, thereby being capable of producing the same structure.

For patterning the Si layer, not a dry etching but a silicon nitride layer may be further formed on the Si layer and thereafter the silicon nitride layer may be patterned to form an etching mask for the Si layer. Also, a wet etching with KOH is performed. In this case, a cross section of the grooves is trapezoidal or triangular.

The biomolecules 108 on the immobilizing member 107 may be bound on the immobilizing member 107 through different biomolecules (for example, APTES, thiol, PNA having an arbitrary arrangement, or the like) previously immobilized on the immobilizing member 107. In this example, when multiple types of biomolecules are prepared on the immobilizing member 107, the groove structure can be used as a unit for determining an immobilized position address.

Figure 41:
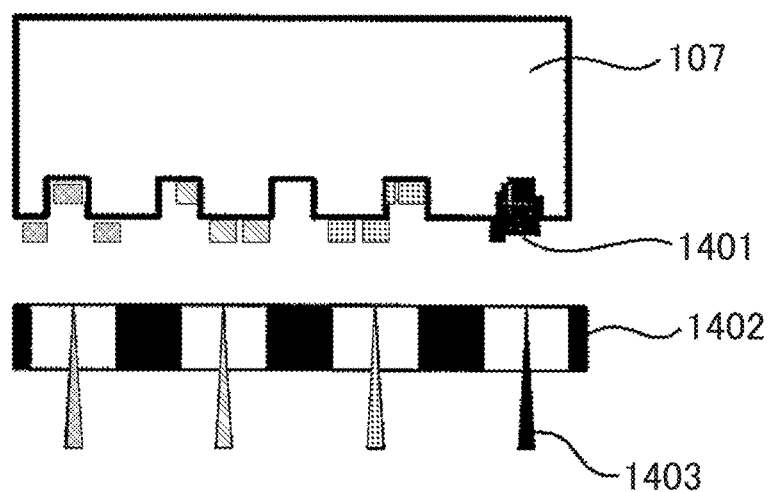
FIG. 41 is a diagram illustrating an example of a method of immobilizing multiple types of biomolecules on the immobilizing member.

FIGS. 41 to 44 show examples of a method of immobilizing the multiple types of biomolecules on the immobilizing member. First, a selection marker is fixed to the immobilizing member 107. At this time, a marker stock solution 1403 is coated on the immobilizing member 107 having the grooves 115 with the use of a mask 1402 by an ink jet system (FIG. 41). As a result, the selection marker 1401 is fixed to the immobilizing member 107. As the marker stock solution 1403, a different kind of stock solution is selected for each address (a region of the immobilizing member 107) according to the biomolecules to be immobilized.

Figure 42:
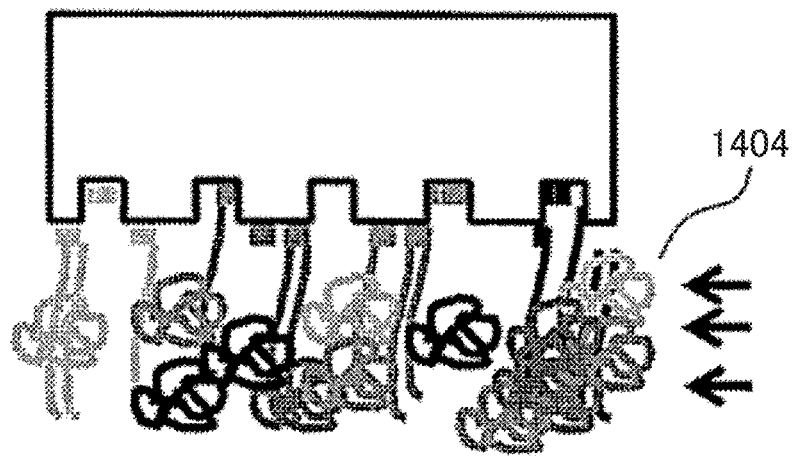
FIG. 42 is a diagram illustrating an example of the method of immobilizing the multiple types of biomolecules on the immobilizing member.
Figure 43:
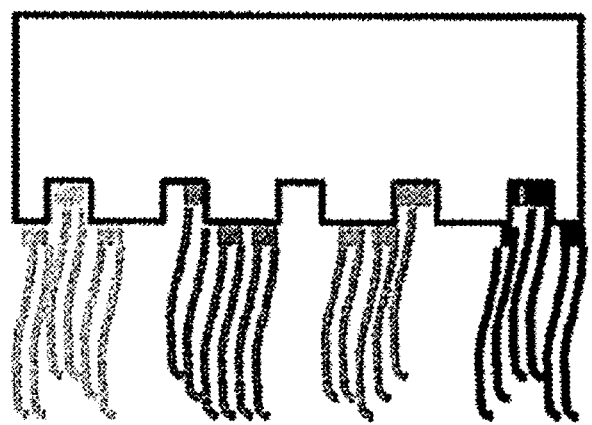
FIG. 43 is a diagram illustrating an example of the method of immobilizing the multiple types of biomolecules on the immobilizing member.
Figure 44:
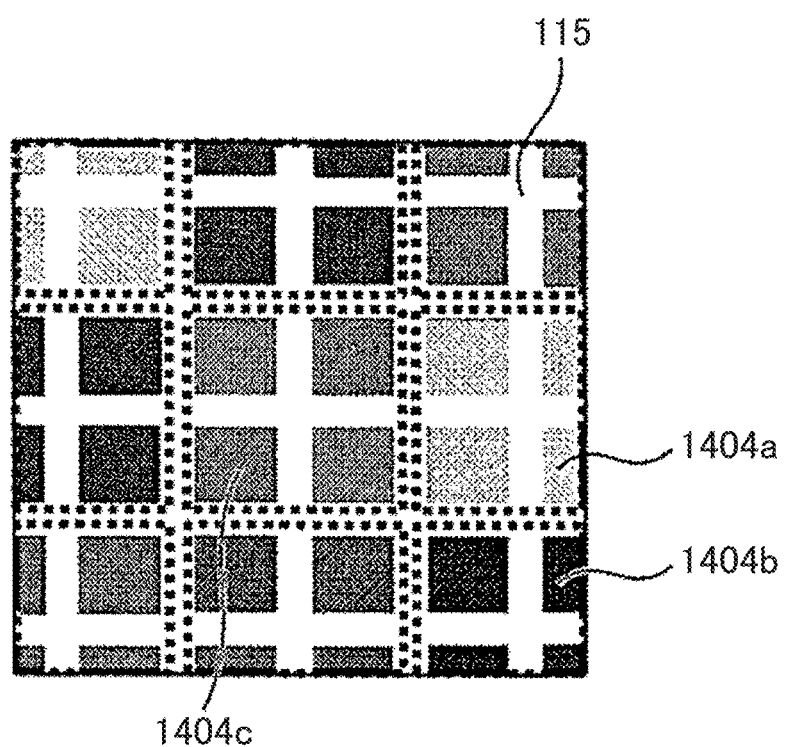
FIG. 44 is a diagram illustrating an example of the method of immobilizing the multiple types of biomolecules on the immobilizing member.

Then, a biomolecule mixture solution 1404 containing the multiple types of biomolecules flows through the immobilizing member 107 (FIG. 42). At this time, the biomolecules are bound to the selection marker 1401 by electrostatic interaction. Since the selection marker 1401 and the biomolecules (DNA) are strongly bound to each other only when arbitrary sequences match each, other, the DNA can be bound in association with each selection marker 1401 (FIG. 43). FIG. 44 is a plan view of the immobilizing member on which the above process has been executed. As shown in FIG. 44, multiple different biomolecules 1404a, 1404b, and 1404c can be bound to each, other for each address of the immobilizing member 107 as shown in FIG. 44.

A method of creating the nanopore device and a method of forming the nanopore have been known and are disclosed, for example, in Itaru Yanagi et al., Sci, Rep. 4, 5000 (2014).

In the present example, a thin film having the nanopore was prepared in the following procedure. First, $Si_3N_4$, $SiO_2$, and $Si_3N_4$ films were formed at the respective thicknesses of 12 nm, 250 nm, and 100 nm on a surface of an 8-inch Si wafer having a thickness of 725 μm, and a film $Si_3N_4$ of 112 nm was formed at a thickness of 112 nm on a back surface of the Si wafer. Then, reactive ion etching was performed on $Si_3N_4$ at the uppermost portion of the surface in a 500 nm square and $Si_3N_4$ at the back surface in a 1038 μm square. Further, the Si substrate exposed by etching on the back surface was etched with TMAH (Tetramethylamraonium hydroxide). During the Si etching, in order to prevent the surface side $SiO_2$ etching, a surface of the wafer was covered with a protective film. After removal of the protective film, the $SiO_2$ layer exposed in a 500 nm square was removed with a BHF solution (HF/NH$_4$F-1/60, 8 min). As a result, the nanopore device in which the thin film $Si_3N_4$ having a thickness of 12 nm is exposed is obtained. At this stage, no nanopore is provided in the thin film.

The formation of the nanopore in the thin film exposed to the nanopore device was carried out by the following procedure by a pulse voltage. Before the nanopore device prepared as described above was set in the biomolecule measuring device, the $Si_3N_4$ thin film was made hydrophilic under the conditions of 10 W, 20 sccm, 20 Pa, and 45 sec by $Ar/O_2$ plasma. Then, the nanopore device was set in the biomolecule measuring device configured to separate into two upper and lower tanks across the nanopore device, the nanopore device was filled with a solution of 1 M KCl, 1 mM Tris-10 mM EDTA, and PH 7.5, and Ag and AgCl electrodes were introduced into each tank.

Voltage application to form the nanopore and measurement of an ion current flowing through the nanopore after formation of the nanopore are performed between the Ag and AgCl electrodes. The lower tank was called "cis tank", the upper tank, was called "trans tank", a voltage $V_{cis}$ on the cis tank side was set to 0 V, and a voltage $V_{trans}$ on the side of the trans tank electrode was selected. The selected voltage was applied by a pulse generator. A current value after each pulse application was read with a current amplifier. The process of voltage application and ion current reading for formation of the nanopore was controlled by a program. As the pulse voltage application condition, a current value condition (threshold current) obtained according to a pore diameter provided in the thin film before applying the pulse voltage was selected to sequentially increase a pore diameter and to obtain a target pore diameter. The pore diameter was estimated according to the ion current value. Table 1 shows a criterion of condition selection. In this example, an n-th pulse voltage application time is determined as follows, $$t_n = 10^{-3+(1/6)(n-1)} - 10^{-3+(1/6)(n-2)} \text{ for } n>2$$

TABLE 1

| Voltage application conditions | | | |
|---|---|---|---|
| Pore diameter before pulse voltage application | Non-opening to 0.7 nmφ | to 1.4 nmφ | to 1.5 nmφ |
| Applied voltage ($V_{cis}$) [V] | 10 | 5 | 3 |
| Initial application time [s] | 0.001 | 0.01 | 0.001 |
| Threshold current | 0.1 nA/0.4 V | 0.6 nA/0.1 V | 0.75 nA/0.1 V |

The formation of the nanopore can also be performed by electron beam irradiation by TEM besides the application of a pulse voltage (A. J, Storm et al., Nat. Mat. 2 (2003)).

Returning to FIG. 1, when a voltage is applied from the power supply 104 to the upper and lower two liquid tanks 131 and 132 through the Ag and AgCl electrodes 103a and 103b, an electric field is generated in the vicinity of the nanopore 112, and the biomolecules 108 negatively charged in the solution pass through the inside of the nanopore 112. On the other hand, since the ends of the biomolecules 108 are immobilized on the immobilizing member 107, the immobilizing member 107 and the driving mechanism 105 are pulled toward the lower tank through the biomolecules 108 due to the electric field.

In this case, for example, in order to accurately read the DNA base sequence, when an output fluctuation of the driving mechanism 5 and vibration derived from disturbance occur, a displacement of the biomolecules 108 is required not to change by a length corresponding to one base, that is, 0.34 nm or more.

Next, the conditions for satisfying the above requirement will be studied. When E is defined, as the Young's modulus, E is expressed, as follows.

$$E = \frac{F * L}{S * \Delta L} \quad \text{[Ex. 1]}$$

In this example, F is a force applied to the system, S is an area of the material, L is a length of the material, and ΔL is the amount of displacement when subjected to the applied force. It is known that a force exerted on the DNA when 1 mV is applied up and down through the nanopore is 0.24 pN (Ulrich F. Keyser et al., Nat. Phys. 2, 473-477 (2006)). Since the fluctuation of the applied voltage during analysis can occur on the order of 0.1 mV, the biomolecules 108 are required not to be displaced by 0.34 nm or more at that time. Therefore, the Young's modulus of the immobilizing member 107, the driving mechanism 105 and the connection member 111 is required to have 0.07 (L/S) [μN/mm²] or more.

It is also important, that the measurement system is thermally stable. The space is known to have the fluctuation of 0.1 degrees even in the absence of a heat source. Therefore, a temperature change in the distance between the nanopore device 101 and the immobilizing member 107, which is calculated based on the entire material used in the system is required to be 0.34 nm or less per 0.1° C.

For that reason, a screw or the like manufactured with the use of stainless steel, invar, or the like may be used as the connection member 111. As another example, the immobilizing member 107 may be fixed to the driving mechanism 105 by vacuum suction or press bonding. The driving mechanism 105 is made of a piezoelectric material typified by a piezoelectric element and can be driven at 0.1 nm/s or more. Examples of the piezoelectric material include barium titanate (BaTiO₃), zirconium titanate Lead (PZT), zinc oxide (ZnO), and the like.

The ends of the biomolecules 108 and the surface of the immobilizing member 107 can be bound to each other by covalent bonds, ionic bonds, electrostatic interactions, magnetic forces, or the like. For example, when the DNA is immobilized, by the covalent bonding, the DNA terminally modified DNA can be immobilized through APTES and glutaraldehyde, Si and SiO which are scaffolds of APTES are leveraged for the immobilizing member 107 to utilize the above bonding. As another covalent bonding method, a gold thiol bond can be used. A 5' end of the DNA is modified with thiol and a surface of the immobilizing member 107 is gold deposited. In addition, as the metal species to be deposited on the immobilizing member 107, Ag, Pt, and Ti to which thiol can be bound, can be used.

The method utilizing ionic bonding is a method of immobilizing the negatively charged biomolecules on the surface of the positively charged immobilizing member 107 by subjecting the immobilizing member 107 to positive charging in the solution by surface modification. Polyaniline or polylysine is used as the cationic polymer. In the case of leveraging the electrostatic interaction, the amino terminally modified DNA can be immobilized directly on the surface of the APTES-modified immobilizing member 107. Also, a nitrocellulose membrane, a polyvinylidene fluoride membrane, a nylon membrane, and a polystyrene substrate are widely used as the substrate surface of the immobilizing member 107. In particular, the nitrocellulose membrane is utilized in the microarray technology. At the time of leveraging a magnetic force, for example, DNA is immobilized in advance on the surface of the magnetic beads by utilizing the bonding as described above. Further, with the use of a magnet material for the immobilizing member 107, the magnetic beads to which the DNA is immobilized interact with the immobilizing member 107 to realize the attraction of the DNA immobilization magnetic beads by the magnetic force. The magnetic material includes iron, silicon steel, amorphous magnetic alloy, nanocrystalline magnetic alloy and the like.

Similarly in the case of measuring proteins or amino acids as the biomolecules, specific binding sites can be modified and bound to the immobilizing member 107 in the same manner. As a result, the binding site in the protein can be identified and sequence information on amino acids can be obtained.

Figure 19:
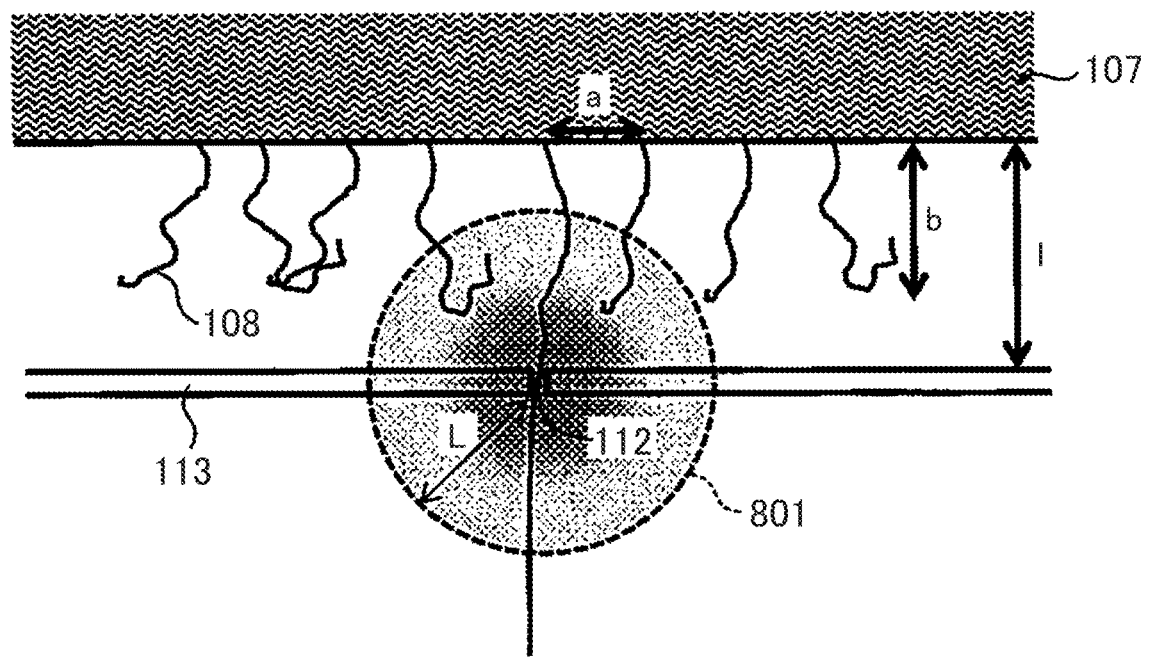
FIG. 19 is a schematic diagram illustrating an example of an electric field generated around the nanopore and introduction of the biomolecule into the nanopore.

The immobilized density of the biomolecules 108 on the immobilizing member 107 is determined, according to a spreading amount of the electric field generated around the nanopore 112. FIG. 19 is a schematic diagram illustrating an example of the electric field generated around the nanopore and the introduction of the biomolecules in the nanopore. As shown in FIG. 19, the potential gradient 801 spreading around the nanopore 112 has the following relationship among a distance L from the nanopore 112, a nanopore diameter d, a thickness t of the thin film, and an applied voltage ΔV.

$$E(r) = \frac{d^2}{8t} \times \left(\frac{1}{L}\right) \times \Delta V \quad \text{[Ex. 2]}$$

For example, when a voltage of 100 mV is applied across the nanopore with a diameter of 1.4 nm provided in the thin film with a film thickness of 2.5 nm, an electric field of 0.1 [V/μm] propagates in a region within 100 nm from the nanopore 112.

In this example, a range in which the biomolecules are confined in the electric field and introduced into the nanopore can be obtained according to an electric mobility μ of the biomolecules and a diffusion coefficient D. When the range is defined as $L_{diff}$, the range is expressed by the following expression.

$$L_{diff} = \frac{d^2 \Delta V}{8t} \times \left(\frac{\mu}{D}\right) \quad \text{[Ex. 3]}$$

A distance at which the immobilizing member 107 comes closest to the thin film 113 is defined as 1. Also, when an effective length of the biomolecules in the solution is defined as b, the biomolecule immobilizing pitch a is expressed based on the above as follows.

$$a > \sqrt{L_{\text{diff}}^2 - (l-b)^2} \qquad \text{[Ex. 4]}$$

Figure 20:
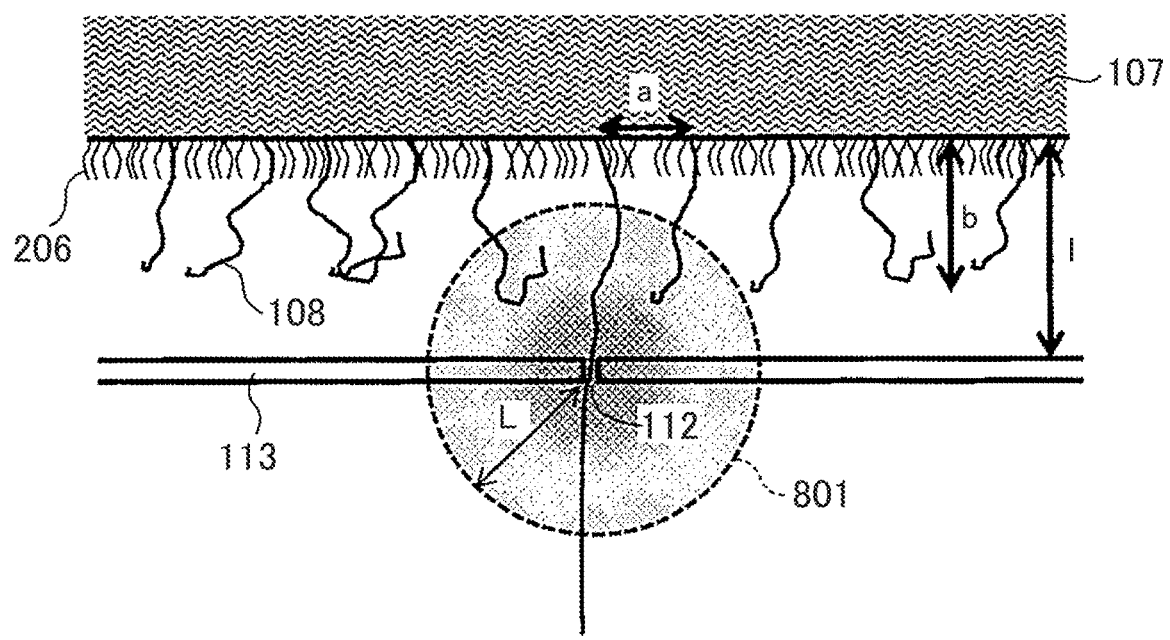
FIG. 20 is a schematic diagram illustrating an example of the electric field generated around the nanopore and introduction of the biomolecule into the nanopore.

In order to realize the above configuration, for example, when DNA is modified on the immobilizing member 107, a DNA solution in which terminally modified short-chain length polymer 206 is mixed is used in addition to the target DNA. FIG. 20 is a schematic diagram illustrating an example of the electric field generated around the nanopore and the introduction of the biomolecules in the nanopore. As shown in FIG. 20, the DNA immobilizing member in which the biomolecules (DNA) 108 are mixed and immobilized with terminally modified short chain length polymer 206, and a target DNA immobilizing density is effectively low can be prepared. For example, it can be confirmed that the phenomenon that multiple DNAs enter one pore can be excluded with the use of the nanopores having a pore diameter of 2.5 to 3 nm when the immobilizing member is prepared with the use of a DNA solution containing 75% of 20 mer poly (dA). In other words, the DNA can be immobilized at about 100 nm pitch. A length of the short chain polymer to be mixed is not necessarily about 2 nm.

According to the above example, in the biomolecule measuring device 100 in which the biomolecule immobilizing region (planar size of the immobilizing member 107) is equal to or larger than a planar size of the thin film 113 having the nanopores 112, the groove structure is formed in at least one of the immobilizing member 107 and the nanopore device 101. As a result, an increase in the passage resistance can be reduced. Because the solution passage resistance is reduced even when the nanopore device 101 and the immobilizing member 107 come into complete contact with each other, the grooves 115 may be continuously provided over a range in which the nanopore device 101 and the immobilizing member 107 are opposed to each other.

One example of the biomolecule measuring device 100 includes the first liquid tank 131 that is filled with the electrolyte solution 102, the second liquid tank 132 that is filled with the electrolyte solution 102, and the nanopore device 101 that supports the thin film 113 having the nanopore 112, and is placed between the first liquid tank 131 and the second liquid tank 132 so as to communication the first liquid tank 131 and the second liquid tank 132 with each other through the nanopore 112. The immobilizing member 107 to which the biomolecules 108 are immobilized is placed in the first tank 131. The biomolecule immobilizing region (a size of a plane opposed to the nanopore device 101) of the immobilizing member 107 is larger than the planar size of the thin film 113. The biomolecule measuring device 100 includes the driving mechanism 105 that drives the immobilizing member 107 so as to be closer to or away from the thin film 113, and the driving mechanism control unit 106 that controls the driving mechanism 105.

The first electrode 103a is disposed in the first liquid tank 131 and the second electrode 103b is disposed in the second liquid tank 132. In order to prevent the contact between the immobilizing member 107 and the thin film 113, the nanopore device 101 is provided as the stop mechanism with the space defining member 114 that surrounds the outer periphery of the thin film 113 like a bank and defines the space between the immobilizing member 107 and the thin film 113. The power supply 104 for applying a voltage is provided between the first electrode 103a and the second electrode 103b. In addition, a measurement unit (the ammeter 109 and the PC 110) that measures an ion current flowing between the first electrode 103a and the second electrode 103b is provided between the first electrode 103a and the second electrode 103b. The measurement unit acquires the sequence information on the biomolecules 108 based on the ion current measured when the biomolecules 108 whose one end is immobilized on the immobilizing member 107 pass through the nanopore 112. At this time, with the structure of the grooves 115 described above, the rise in the passage resistance can be reduced and the decrease in the time constant can be reduced. As a result, the blunting of the acquired signal waveform is eliminated and the SN is improved.

With the above configuration, a high-speed response can be performed to a signal change reflecting the structure of the biomolecules, and high-precision reading is realized. In addition, in the above example, the introduction of the biomolecules 108 into the nanopore 112 can be realized without confirmation of the position of the nanopore 112 in the thin film 113, and the acquisition of the stable blockage signal can be realized.

Example 2

Figure 45:
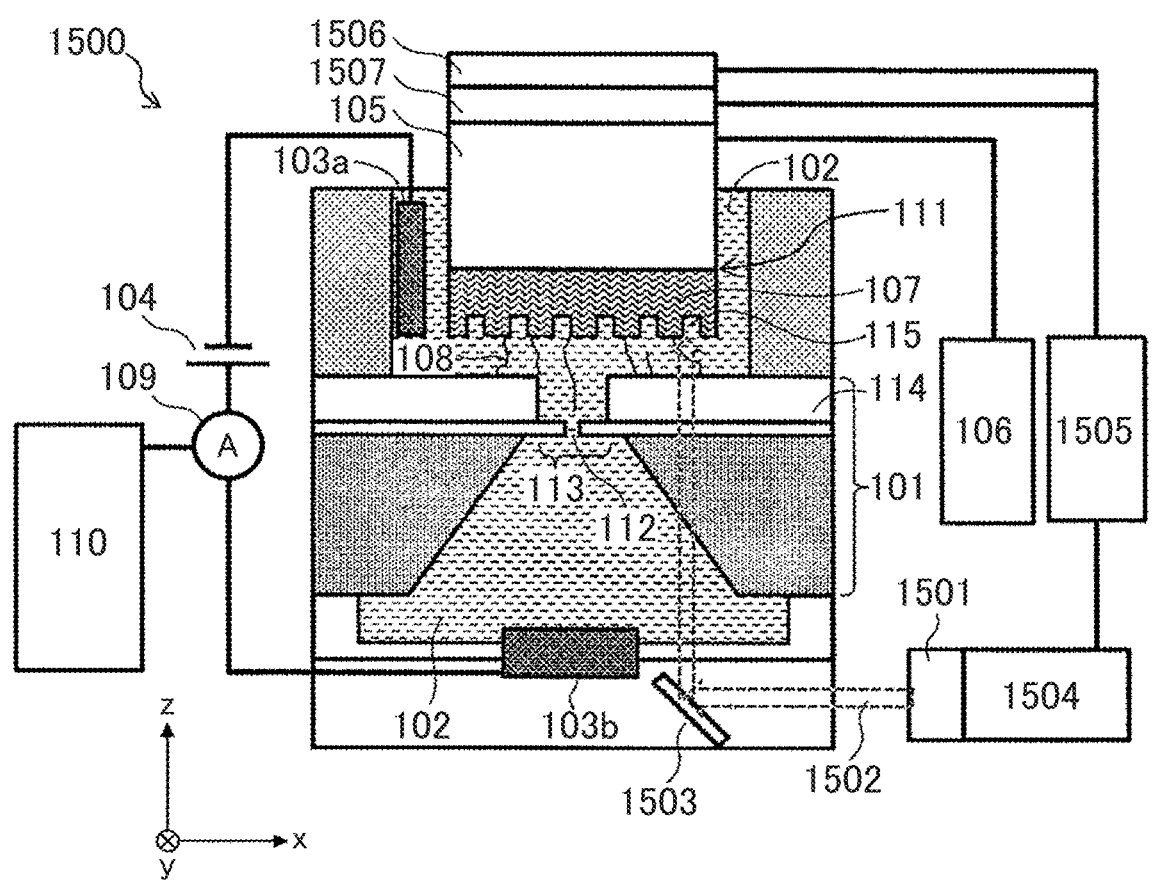
FIG. 45 is a diagram illustrating a first example of a mechanism for adjusting a positional relationship between the nanopore device and the immobilizing member.

Next, the positioning mechanism using the groove structure will be described. FIG. 45 shows a first example of a mechanism for adjusting a positional relationship between the nanopore device and the immobilizing member. In FIG. 45, the same components as those described above are denoted by the same reference numerals, and a description of the same components will be omitted.

As described above, in the case where a pitch of grooves 115 is wide, when multiple kinds of biomolecules 108 are immobilized on an immobilizing member 107, if grooves 115 are provided in both of the immobilizing member 107 and a nanopore device 101, a positional relationship between the nanopore device 101 and the immobilizing member 107 needs to be adjusted.

A biomolecule measuring device 1500 includes, in addition to the components shown in FIG. 1, a laser irradiation unit 1501, a mirror 1503, a mechanism (relative position monitor) 1504 that feeds back data acquired by irradiation of a laser 1502, a rotation mechanism 1506 for the immobilizing member 107, an adjustment mechanism 1507 for the immobilizing member 107 in an xy direction, and a control unit 1505 that controls the rotation mechanism 1506 and the adjustment mechanism 1507.

The control unit 1505 can control the rotation mechanism 1506 and the adjustment mechanism 1507 with the use of the data from the relative position monitor 1504 to control the rotation and the movement in the xy direction of the immobilizing member 107. As an example, the control unit 1505 may adjust the rotation and the xy direction of the immobilizing member 107 so that the groove structure imaged by the laser irradiation matches a pattern formed on the nanopore device 101.

The immobilizing member 107 or the nanopore device 101 which is provided with the grooves 115 can also function as a positioning mechanism. As an example of a configuration for realizing the positioning mechanism, a measurement unit (control unit 1505) for imaging the groove structure by laser irradiation may be provided. The rotation and the xy direction of the immobilizing member 107 may be adjusted by the rotation mechanism 1506 and the adjustment mechanism 1507 according to the result of the measurement unit. As a result, a relative distance between the groove structure and the nanopore device can be adjusted.

Figure 46:
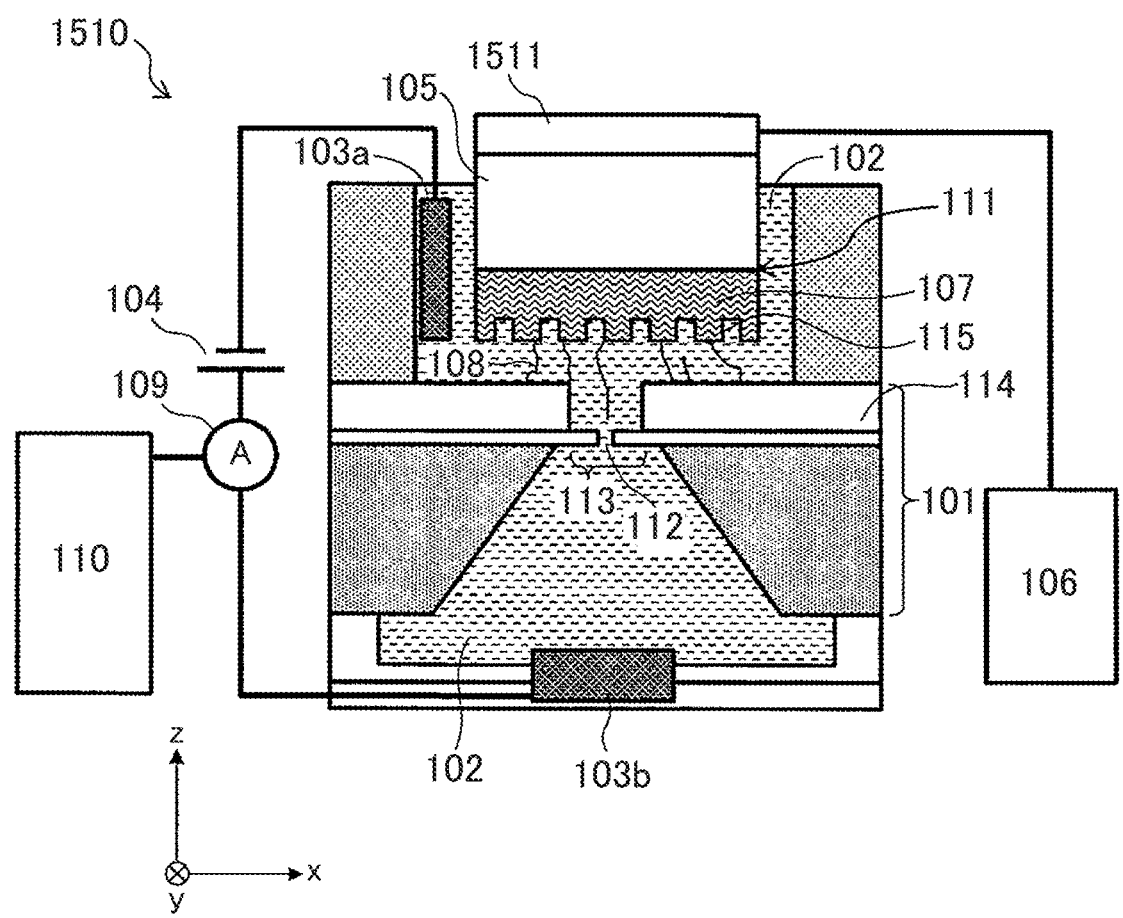
FIG. 46 is a diagram illustrating a second example of the mechanism for adjusting the positional relationship between the nanopore device and the immobilizing member.

FIG. 46 shows a second example of a mechanism for adjusting a positional relationship between the nanopore device and the immobilizing member. A solution resistance per se around the nanopore device may be used as the positioning mechanism. The biomolecule measuring device 1510 includes, in addition to the components shown in FIG. 1, a rotation mechanism 1511 of the immobilizing member 107. In this example, the driving mechanism control unit 106 receives the measured solution resistance as an input. The driving mechanism control unit 106 controls the rotation mechanism 1511 to rotate the immobilizing member 107 while monitoring the solution resistance.

When a position between the nanopore device 101 and the immobilizing member 107 is displaced, the solution resistance becomes high. The driving mechanism control unit 106 rotates an axis of the immobilizing member 107 while monitoring the solution resistance, to thereby move a position of the grooves 115 of the immobilizing member 107 to a desired position. As a result, the solution resistance is lowered. In the configuration of FIG. 46, since the laser source or the like is not necessary, the device configuration can be simplified.

Example 3

An increase in solution resistance is not limited to a problem of a transport control system using the immobilizing member 107. Also, in a configuration of a nano flow path where a structure around a nanopore 112 is narrowed to a region of the micro order, the increase in the solution resistance is a potential problem. In the following, a configuration example of a biomolecule measuring device without the use of an immobilizing member will be described.

Figure 47:
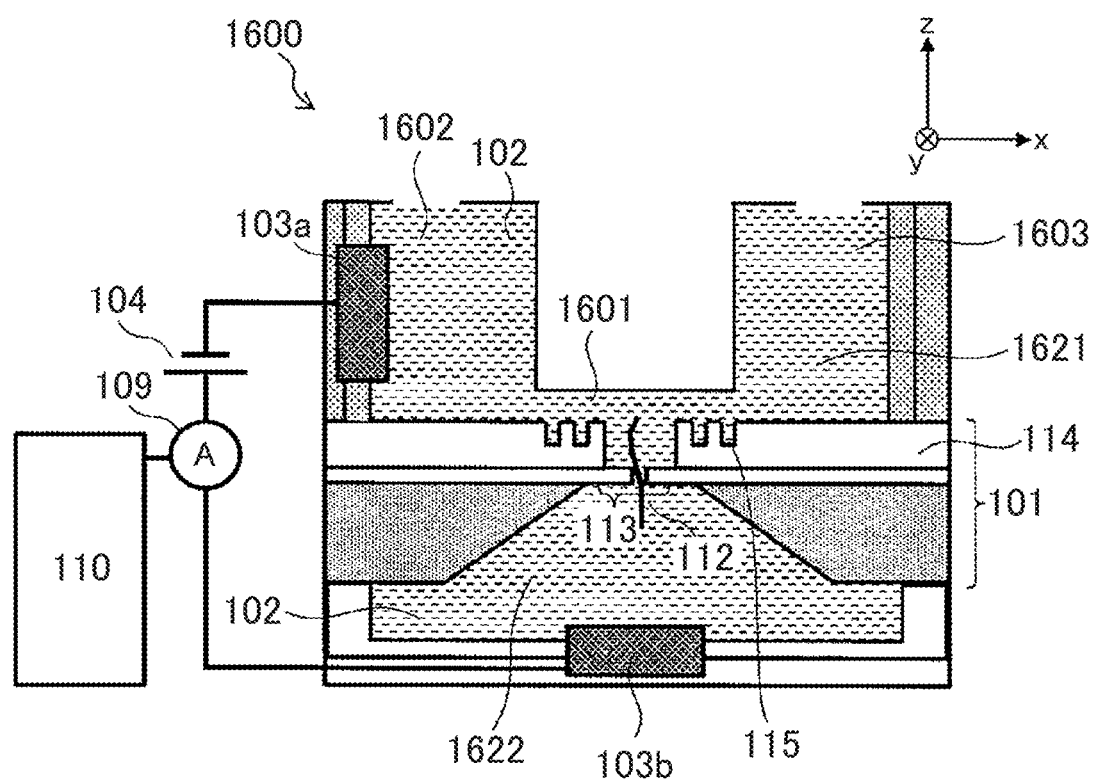
FIG. 47 is a schematic cross-sectional view illustrating a configuration example of a biomolecule measuring device without the use of the immobilizing member.
Figure 48:
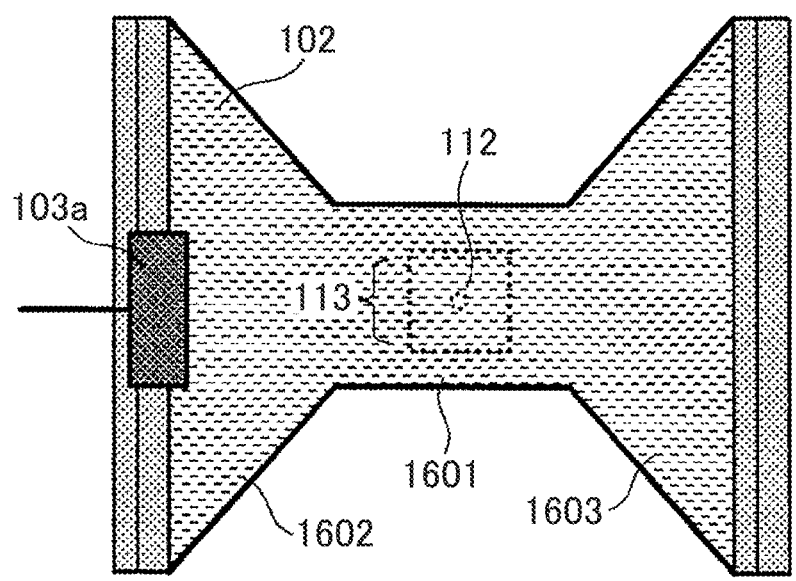
FIG. 48 is a top view of the biomolecule measuring device without the use of the immobilizing member.

FIG. 47 is a schematic cross-sectional view illustrating a configuration example of a biomolecule measuring device without the use of an immobilizing member. FIG. 48 is a top view of the biomolecule measuring device in FIG. 47.

A biomolecule measuring device 1600 includes a first liquid tank 1621 that is filled with an electrolyte solution 102 and a second liquid tank 1622 that is filled with an electrolyte solution 102. The first liquid tank 1621 includes a flow path (fine flow path) 1601 of a nano size or micro size. In the present example, the flow path 1601 is a micro flow path.

The biomolecule measuring device 1600 includes a nanopore device 101 as in the examples described above. The nanopore device 101 includes a thin film 113 with a nanopore 112 and a space defining member 114 with grooves 115. The nanopore device 101 is placed between a first liquid tank 1621 and a second liquid tank 1622 so as to communicate the first liquid tank 1621 and the second liquid, tank 1622 with each other through the nanopore 112.

A first electrode 103a is placed in the first liquid tank 1621 and a second electrode 103b is placed in the second liquid tank 1622. A power supply 104 and an ammeter 109 are connected, between the first and second electrodes 103a and 103b. The ammeter 109 is connected to an ADC (not shown) and a PC 110, and the PC 110 can record an acquired current value. Therefore, sequence information on the biomolecule can be acquired from an ionic current measured when the molecule passes through the nanopore 112 with the use of the ammeter 109.

In the present example, the first liquid tank 1621 has an inlet 1602 and an outlet 1603. As shown in FIG. 48, a region that is provided in the vicinity of the nanopore 112 between the inlet 1602 and the outlet 1603 defines a micro flow path 1601.

In such a configuration, as the microchannel 1601 is narrower, more of the efficiency of biomolecule introduction into the nanopore 112, blockage of the flow path, introduction order of biomolecules, and so on can be controlled. On the other hand, when analysis is performed with the use of an ion current, a time constant of a circuit is lowered according to a length and a cross-sectional area of the micro flow path 1601.

In the nanopore device 101 provided between the first liquid tank 1621 and the second liquid tank 1622, the space defining member 114 that comes into contact with the first liquid tank 1621 has the grooves 115. In the present example, the grooves 115 are provided in a region the vicinity of the nanopore 112 in the first liquid tank 1621, within a range of the region (that is, the flow path 1601) in which the flow path is narrowed, and formed in the space defining member 114 (FIG. 47). With the provision of the groove structure, a signal time constant can be prevented from decreasing.

As described above, the solution resistance may also increase in the biomolecule measuring device 1600 using the nanopore 112 existing in the narrow flow path without the use of the fixed substrate. Therefore, similarly, in the biomolecule measuring device 1600 without the use of the fixed substrate, it is effective to form a groove structure (or concave portions) in the nanopore device 101.

Example 4

Figure 49:
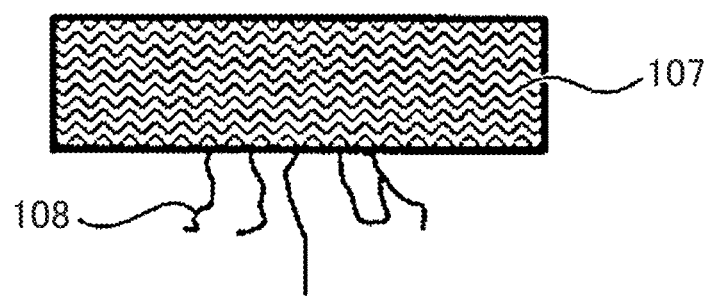
FIG. 49 is a schematic diagram, illustrating a first example of a procedure of binding the biomolecules to the immobilizing member and a procedure of installing the immobilizing member in the biomolecule measuring device.
Figure 50:
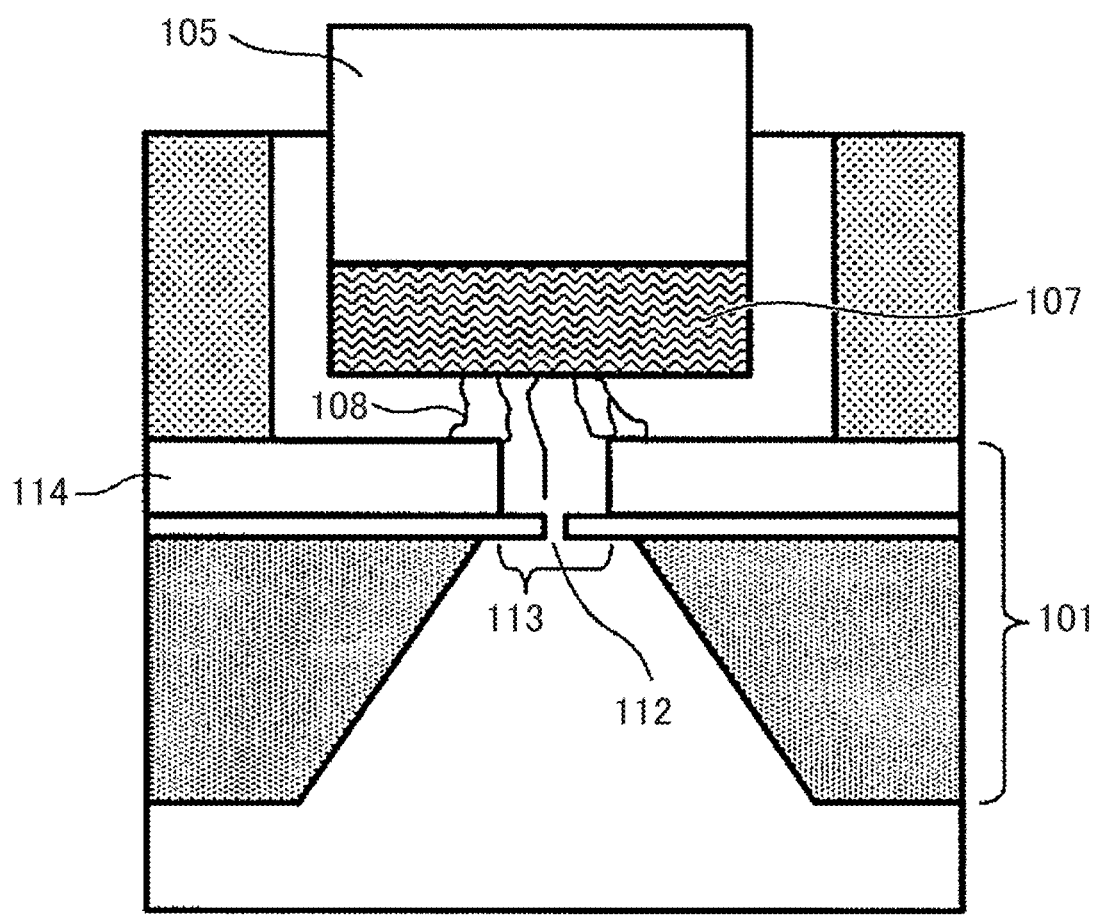
FIG. 50 is a schematic diagram illustrating the first example of the procedure of binding the biomolecules to the immobilizing member and the procedure of installing the immobilizing member in the biomolecule measuring device.
Figure 51:
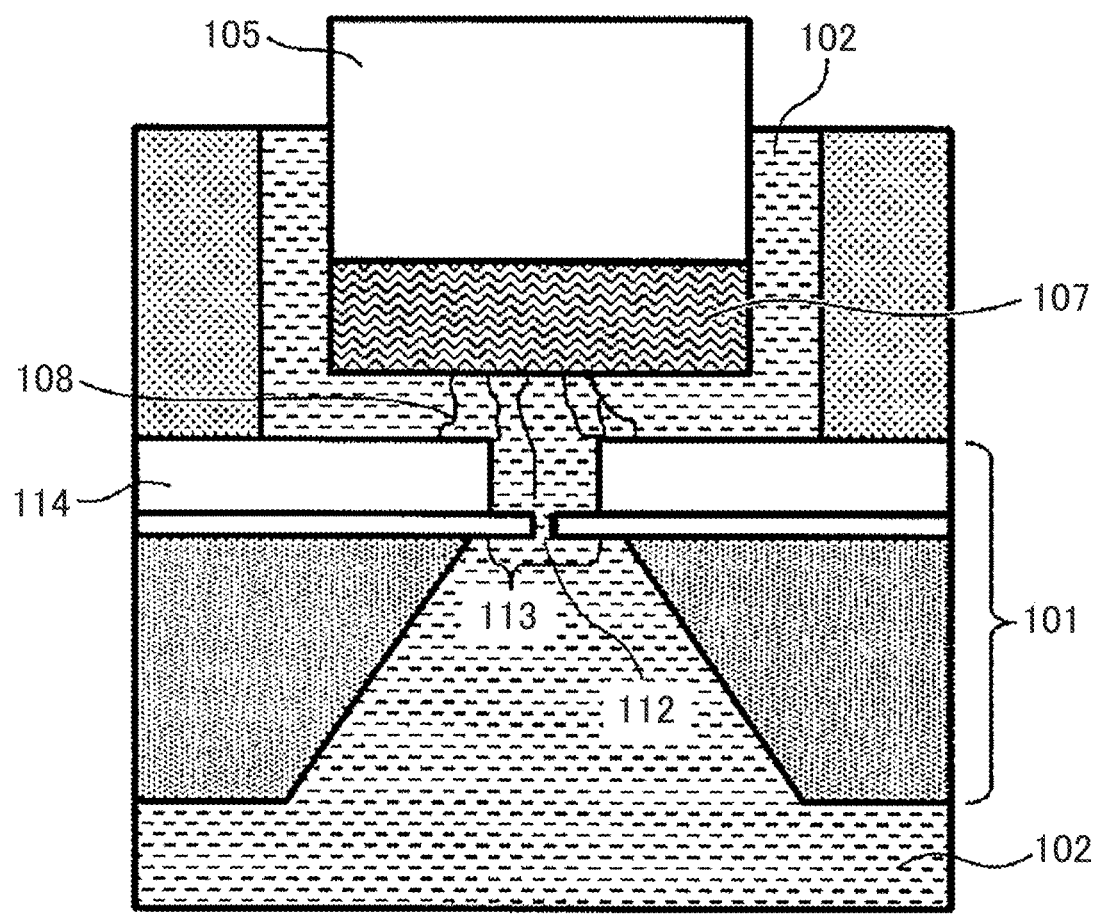
FIG. 51 is a schematic diagram illustrating the first example of the procedure of binding the biomolecules to the immobilizing member and the procedure of installing the immobilizing member in the biomolecule measuring device.

FIGS. 49 to 51 are schematic diagrams illustrating a first example of a procedure of binding biomolecules to an immobilizing member and a procedure of installing the immobilizing member to a biomolecule measuring device. For the sake of simplifying the description, electrodes and grooves 115 are omitted from illustration. A preparatory step before measurement includes three steps. In a first step shown in FIG. 49, biomolecules 108 are immobilized on an immobilizing member 107. In a second step shown in FIG. 50, the immobilizing member 107 and a driving mechanism 105 are connected to each other and inserted into an upper tank of the biomolecule measuring device. In a third step shown in FIG. 51, an electrolytic solution 102 is introduced into upper and lower spaces of a nanopore device 101.

Figure 52:
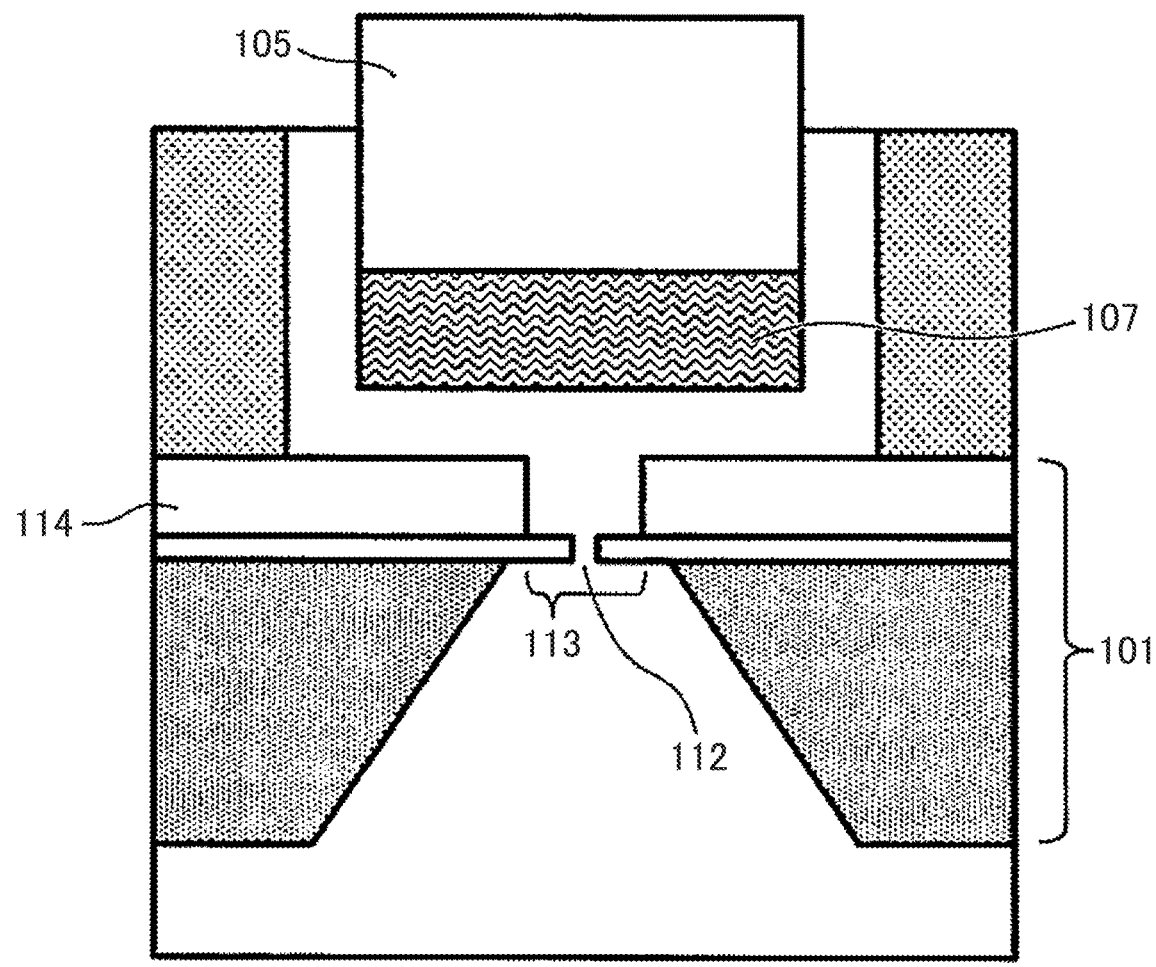
FIG. 52 is a schematic view illustrating a second example of the procedure of binding the biomolecules to the immobilizing member.
Figure 53:
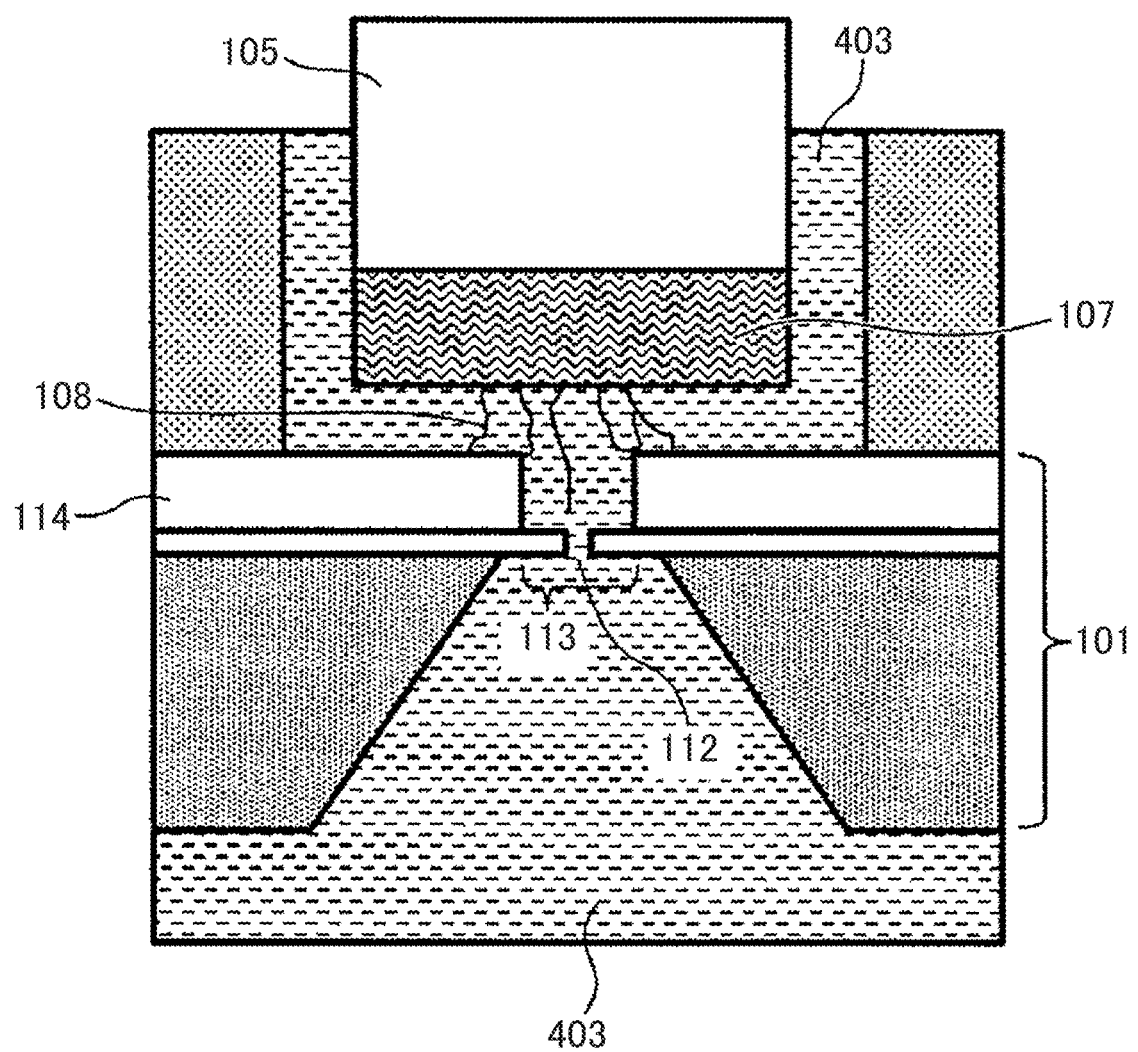
FIG. 53 is a schematic view illustrating the second example of the procedure of binding the biomolecules to the immobilizing member.

FIGS. 52 and 53 are schematic diagrams illustrating a second example of a procedure of binding the biomolecules to the immobilizing member. For simplification of description, illustration of electrodes and the grooves 115 is omitted. A preparatory step before measurement includes two steps. In a first step shown in FIG. 52, the immobilizing member 107 is connected to the driving mechanism 105 and inserted into an upper bath of the biomolecule measuring device. In a second step shown in FIG. 53, a biomolecule mixed electrolyte solution 403 in which the biomolecules 108 capable of being bound to the immobilizing member 107 are dissolved is poured into the upper tank and the lower tank of the biomolecule measuring device.

In this example, in order to minimize nonspecific adsorption as much as possible and to increase a density at which target binding is carried out on a surface of the immobilizing member, a binding material for binding the biomolecules to the surface of the immobilizing member needs to be modified on the surface of the immobilizing member 107 in advance. The binding material refers to APTES and glutaraldehyde when the biomolecules are immobilized, for example, leveraging covalent bonding through APTES glutaraldehyde. When the biomolecules are immobilized leveraging ion binding, it refers to the organic material on the substrate surface, the binding material refers to an organic material of a substrate surface.

In the case where the biomolecules are along-chain DNAs, more particularly, in a sequence in which multiple guanines are consecutively arranged, strong folding of DNAs causes a problem. When the DNA is folded, a phenomenon that clogging occurs in the vicinity of the nanopore and biomolecules do not pass through the nanopore may occur. For that reason, it is preferable to perform a process of heating the immobilizing member that immobilizes the DNAs in water at high temperature, more particularly, 60° C. to 98° C. for 10 to 120 minutes, and then quenching the immobilizing member down to 4° C. Thereafter, the biomolecules are measured in a KCl solution at 4° C. or room temperature.

Figure 54:
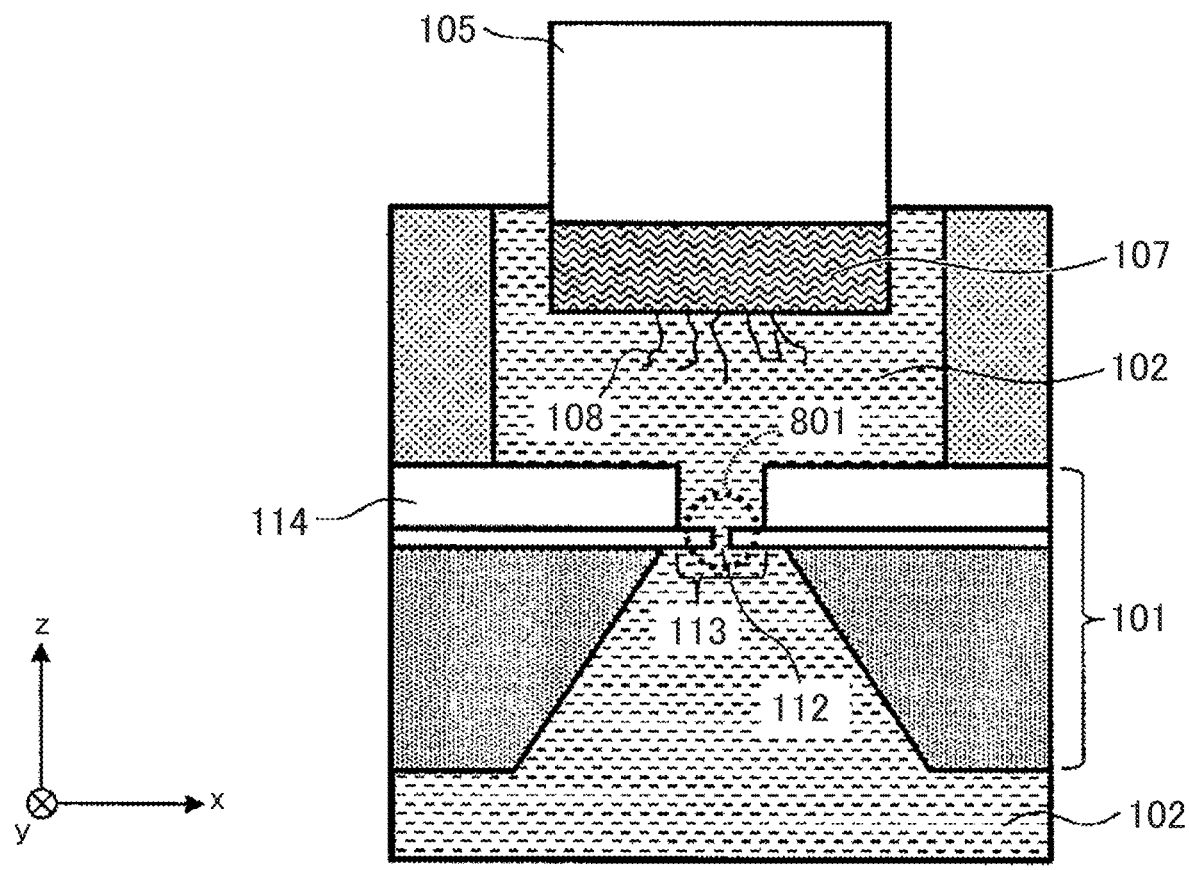
FIG. 54 is a schematic diagram illustrating a driving procedure of the immobilizing member.

FIGS. 54 to 57 are schematic diagrams illustrating a procedure of driving the immobilizing member. The illustration of the electrode and the grooves 115 is omitted for the sake of simplifying the description. The driving method of the immobilizing member 107 includes three steps. FIG. 54 shows a state in which the immobilizing member 107 having the biomolecules 108 to be measured immobilized on a lower surface of the immobilizing member 107 is inserted into the upper liquid tank of the biomolecule measuring device, and an electrolyte solution is introduced into the upper and lower liquid tanks to prepare for measurement.

Figure 55:
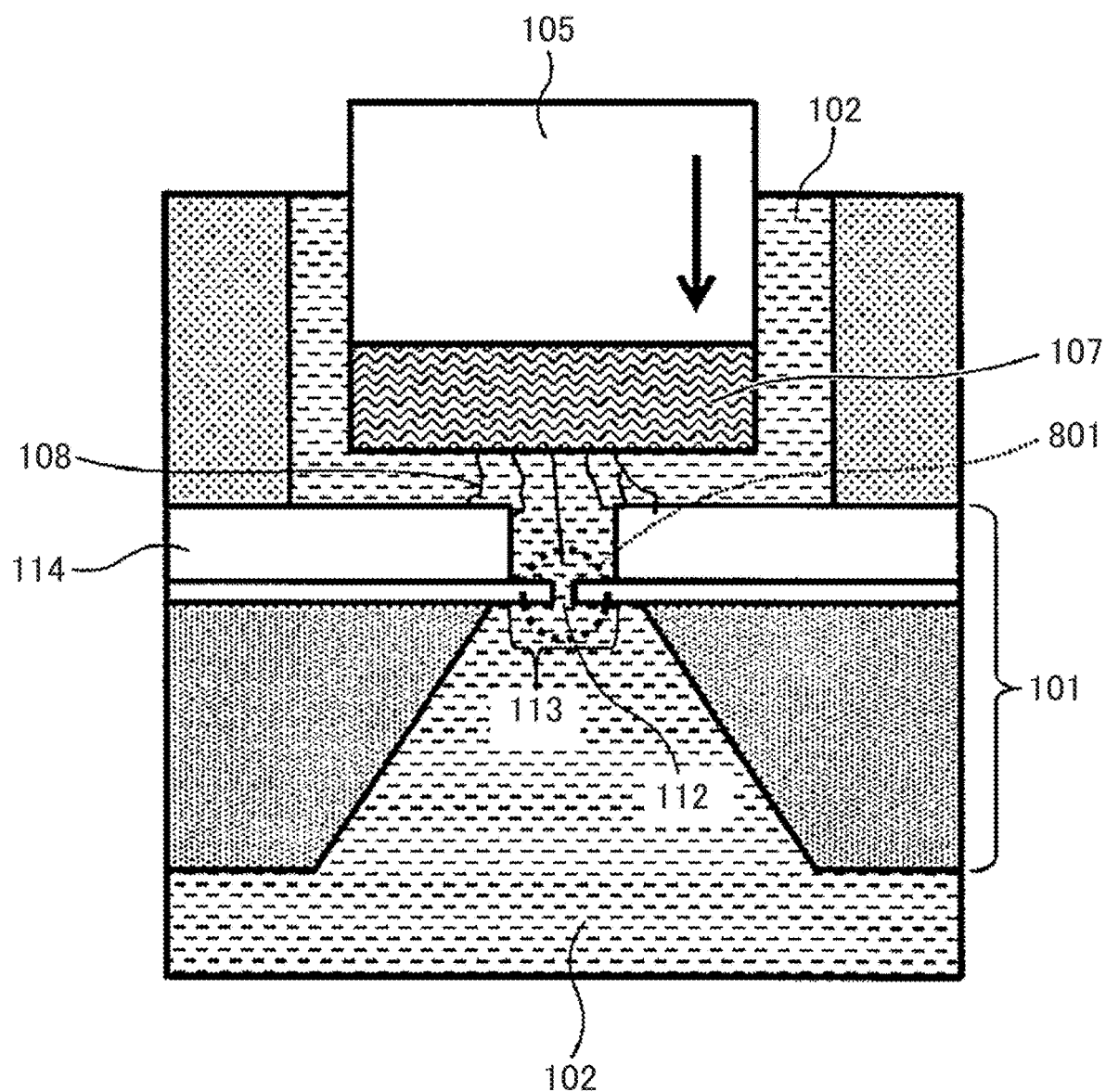
FIG. 55 is a schematic diagram illustrating the driving procedure of the immobilizing member.

In a first step of driving the immobilizing member shown in FIG. 55, the driving mechanism control unit 106 controls the driving of the driving mechanism 105 to drive the immobilizing member 107 downward in a z axis, and to insert the biomolecules 108 immobilized to the immobilizing member 107 in a potential gradient 801 generated in the vicinity of the nanopore 112 of the thin film 113. At this time, if the biomolecule 108 is negatively charged, or if the biomolecule 108 is modified with negative charge, upon receiving a force from the electric field, the biomolecule 108 tries to pass through the nanopore 112 from an unfixed free end of the biomolecule 108 and to move into the lower liquid tank. The biomolecule 108 passes through the nanopore 112 and is stretched between a portion of the biomolecule 108 located within the potential gradient 801 and an end of the biomolecule 108 immobilized on the immobilizing member 107. The introduction of the biomolecule into the nanopore 112 can be monitored from the ionic current.

Figure 56:
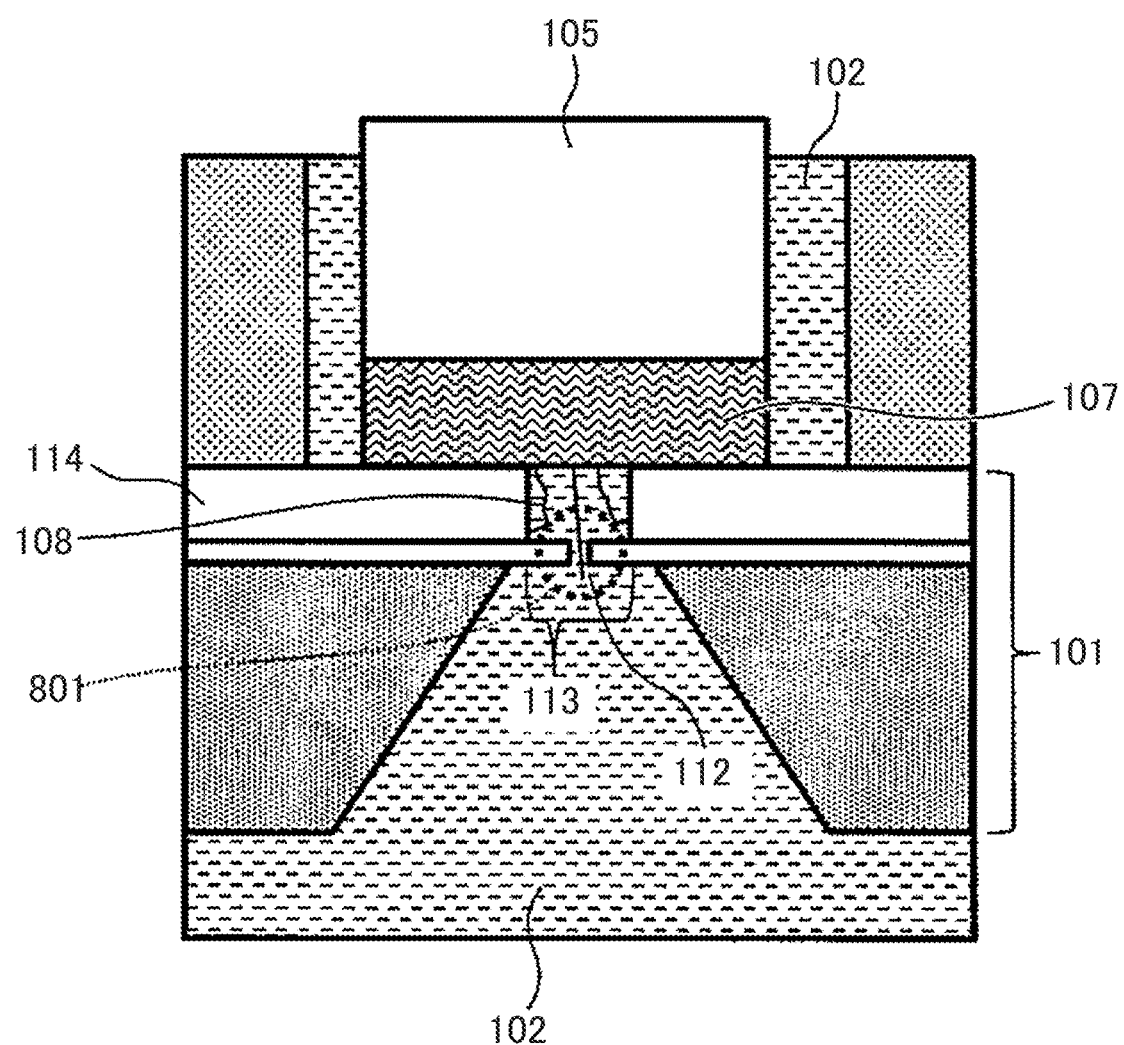
FIG. 56 is a schematic diagram illustrating the driving procedure of the immobilizing member.

In a second step shown in FIG. 56, the driving mechanism 105 further drives the immobilizing member 107 downward, in a z-axis direction to come into contact with the space defining member 114 formed on the nanopore device 101, and stops the movement of the immobilizing member 107. The existence of the space defining member 114 above the thin film 113 makes it possible to avoid a contact between the immobilizing member 107 and the thin film 113 and to prevent the thin film 113 from being destroyed. When the biomolecule 108 does not enter the inside of the nanopore 112 of the thin film 113 at the time of completing the second step, the drive of the drive mechanism 105 is stopped for a certain period of time, thereby being capable of increasing the introduction probability.

Figure 57:
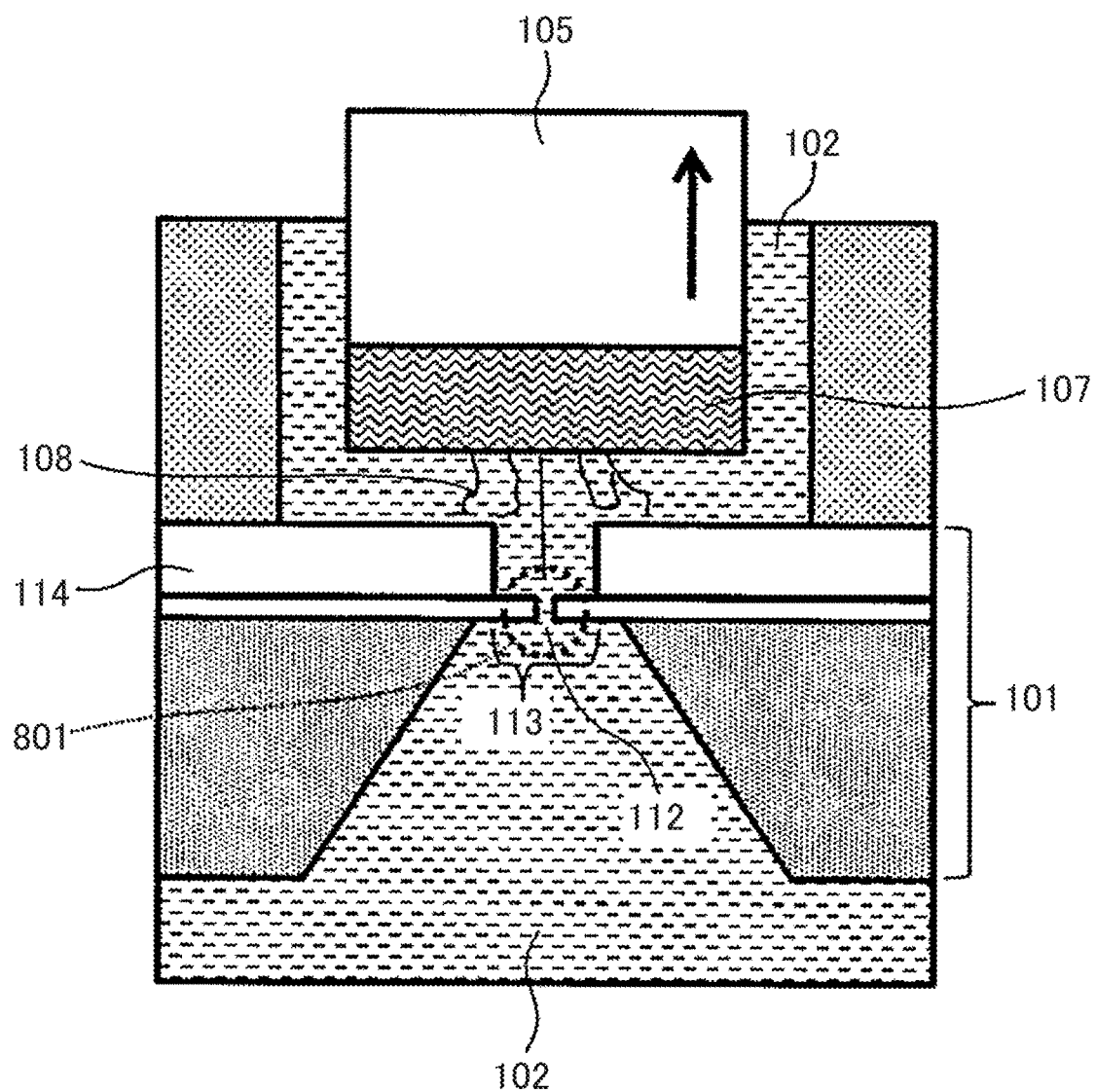
FIG. 57 is a schematic diagram illustrating the driving procedure of the immobilizing member.

In a third step shown in FIG. 57, the driving mechanism control unit 106 drives the driving mechanism 105 in a direction away from the nanopore device 101. At this time, the biomolecule 108 is pulled by the immobilizing member 107 and moves upward within the nanopore 112 while being stretched by an electric field, and during this time, the sequence of the biomolecules is read based on the amount of change in the ion current. A signal value read by the ammeter 109 is amplified as necessary, and recorded in the PC 110.

Figure 58:
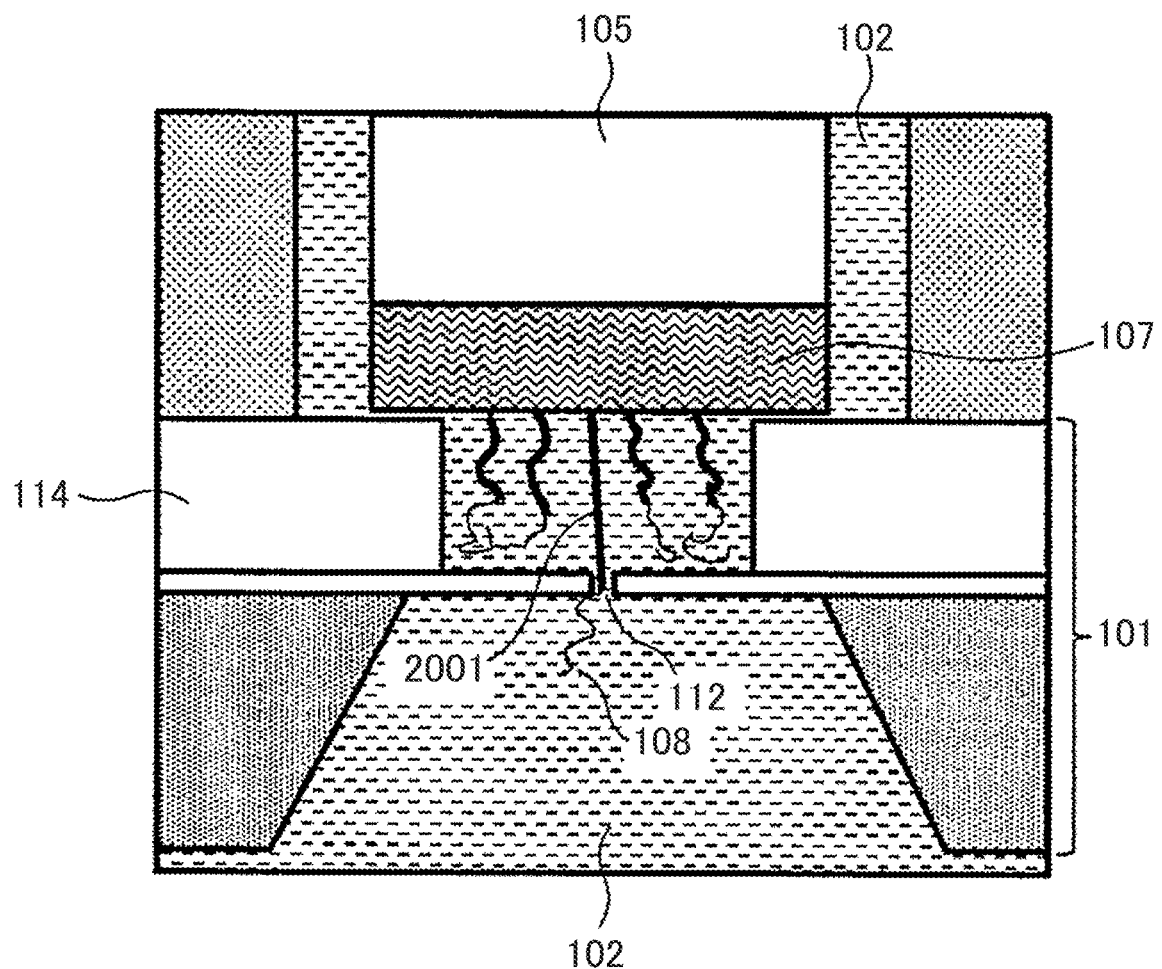
FIG. 58 is a schematic diagram illustrating an example of binding through a linker.

A point of time when the immobilizing member 107 comes into contact with the space defining member 114 in the second step is an analysis starting point of a biomolecule characteristic analysis performed in the third step. Therefore, a region corresponding to a height of the space defining member 114 from an immobilized point in a whole length of the biomolecule cannot be analyzed without passing through the nanopore 112. In this example, as shown in FIG. 58, when the biomolecules 108 are immobilized to the immobilizing member 107, the biomolecules 108 are immobilized on the immobilizing member 107 through a linker 2001 having a height corresponding to the space defining member 114, all of the sequences in the biomolecules 108 can be read.

Figure 59:
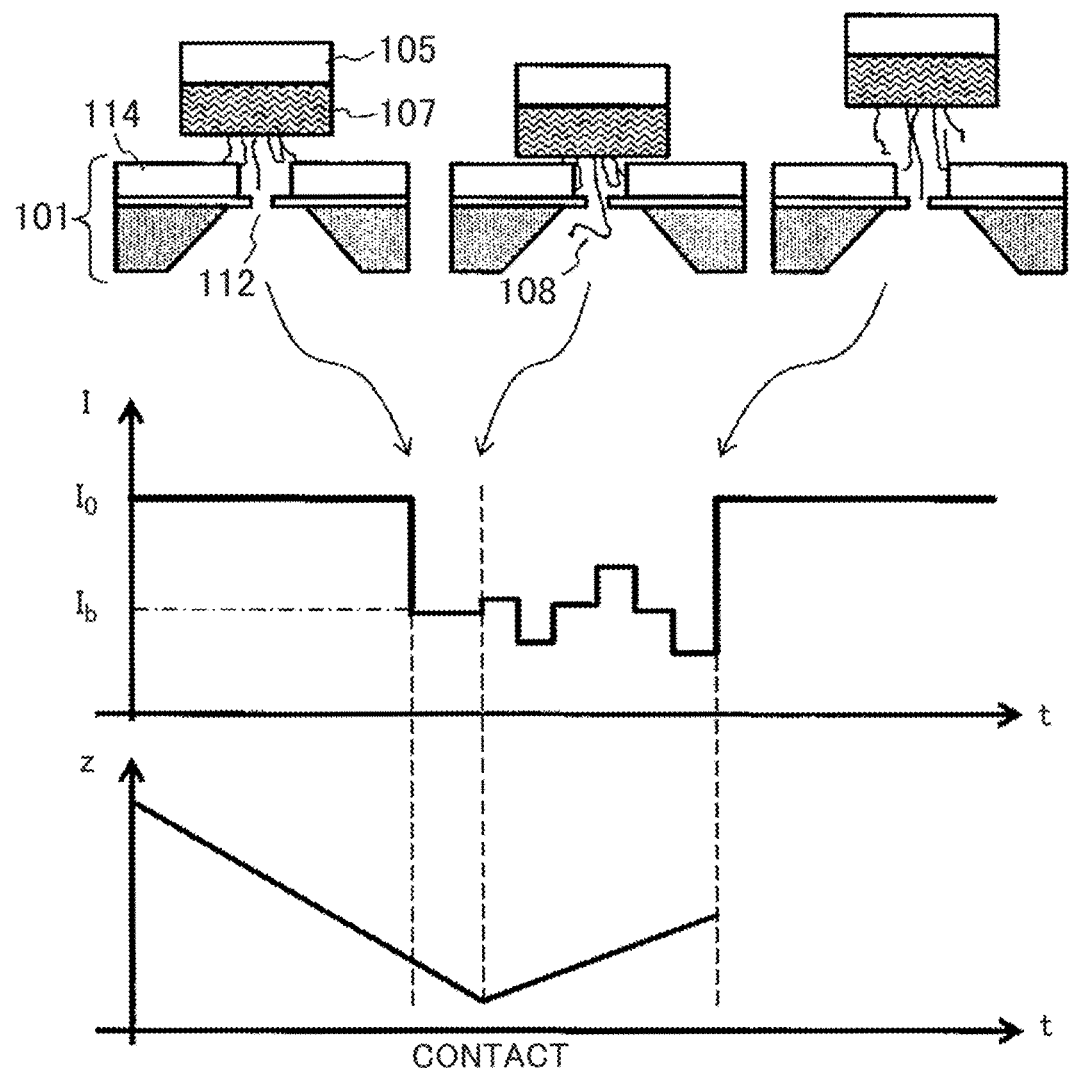
FIG. 59 is a schematic diagram, illustrating an example of detection of an ionic current signal.

FIG. 59 is a schematic diagram illustrating an example of detection of an ionic current signal. FIG. 59 shows a schematic diagram of a positional relationship of the immobilizing member to the nanopore device in an upper stage, shows a graph of a change in the ionic current signal in a middle stage, and shows a graph of the displacement of a driving mechanism in a lower stage. A drive mechanism displacement z in the lower stage corresponds to a distance between the nanopore device 101 and the immobilizing member 107. In addition, in FIG. 59, a positional relationship between the immobilizing member 107 corresponding to a feature point in the ionic current signal and the nanopore device 101 is indicated by arrows.

Referring to FIG. 59, before the immobilizing member 107 comes close to the nanopore device 101, an ionic current signal $I_0$ corresponding to a nanopore diameter is obtained. When the biomolecule 108 enters the nanopore 112, a decrease in the amount of ion current corresponding to an average diameter of the biomolecules occurs. At this time, a speed at which the biomolecules pass through the nanopore 112 is not a driving speed of the immobilizing member 107 but a speed of free electrophoresis of the biomolecules. This is because the biomolecules are folded and bent when the biomolecules enter an electric field from the outside of the electric field, and therefore the biomolecules are not affected by a fact that the ends of the biomolecules is immobilized on the immobilizing member 107. In this case, a measurement resolution cannot be obtained, and an acquired ion current value indicates an average current value $I_b$ depending on the biomolecule average diameter.

Since a transporting speed of the biomolecules when lifting the biomolecules by the driving mechanism 105 after the immobilizing member 107 comes into contact with the space defining member 114 of the nanopore device 101 is equal to a moving speed of the immobilizing member 107, the biomolecules can be transported at a speed required for a characteristic resolution. For example, in order to measure a difference between individual base types contained in the DNA chain by the blockade current amount, it is conceivable that a nanopore passage speed of the DNA needs to be set to 100 µs or more per base because of a time constant of the current noise at the time of measurement and the fluctuation of the DNA molecules. Therefore, the driving mechanism 105 is controlled to move the immobilizing member 107 upward at a speed lower than 100 µs per base, thereby being capable of obtaining a signal reflecting the base sequence of the biomolecules. On the other hand, since analysis throughput needs to be kept high, it is desirable that the speed is less than 10 ms per base. In other words, it is preferable that the driving mechanism drives the biomolecule immobilizing member at a speed between 34 nm/sec and 34 µm/sec.

Figure 60:
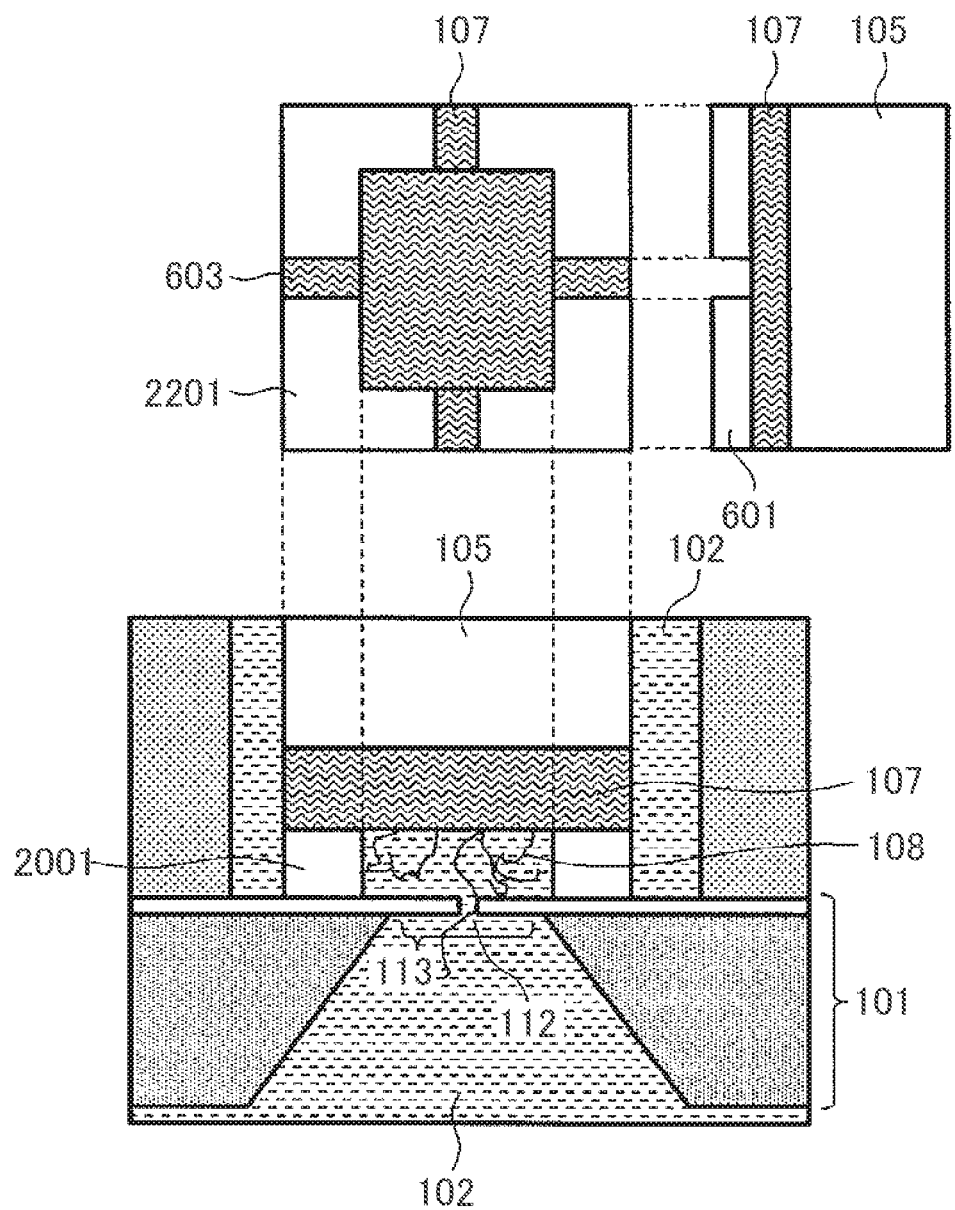
FIG. 60 is a schematic view illustrating a first example of a stop mechanism for preventing a contact between the immobilizing member and a thin film.

FIG. 60 is a schematic view illustrating a first example of a stop mechanism for preventing a contact between the immobilizing member and the thin film. The illustration of the grooves 115 is omitted for simplification of description. FIG. 60 also shows a schematic side view of the immobilizing member 107 including the driving mechanism 105 and a bottom view having a slit 603. In this example, the space defining member 2201 is placed not on the nanopore device 101 but so as to protrude downward from a lower surface of the immobilizing member 107. The space defining member 2201 is formed on an outer circumference of the lower surface of the immobilizing member 107, four corners of the lower surface, or two opposite sides so as to come into contact with the nanopore device 101 at a position outside the thin film 113. In other words, the space defining member 2201 is provided on at least a part of the lower surface of the immobilizing member 107 outside the region opposed to the thin film 113. When the immobilizing member 107 moves in the direction of the nanopore device 101, a space is defined between the immobilizing member 107 and the thin film 113 by the aid of the space defining member 601, and the thin film 113 is prevented from being broken by a contact with the immobilizing member 107.

Figure 61:
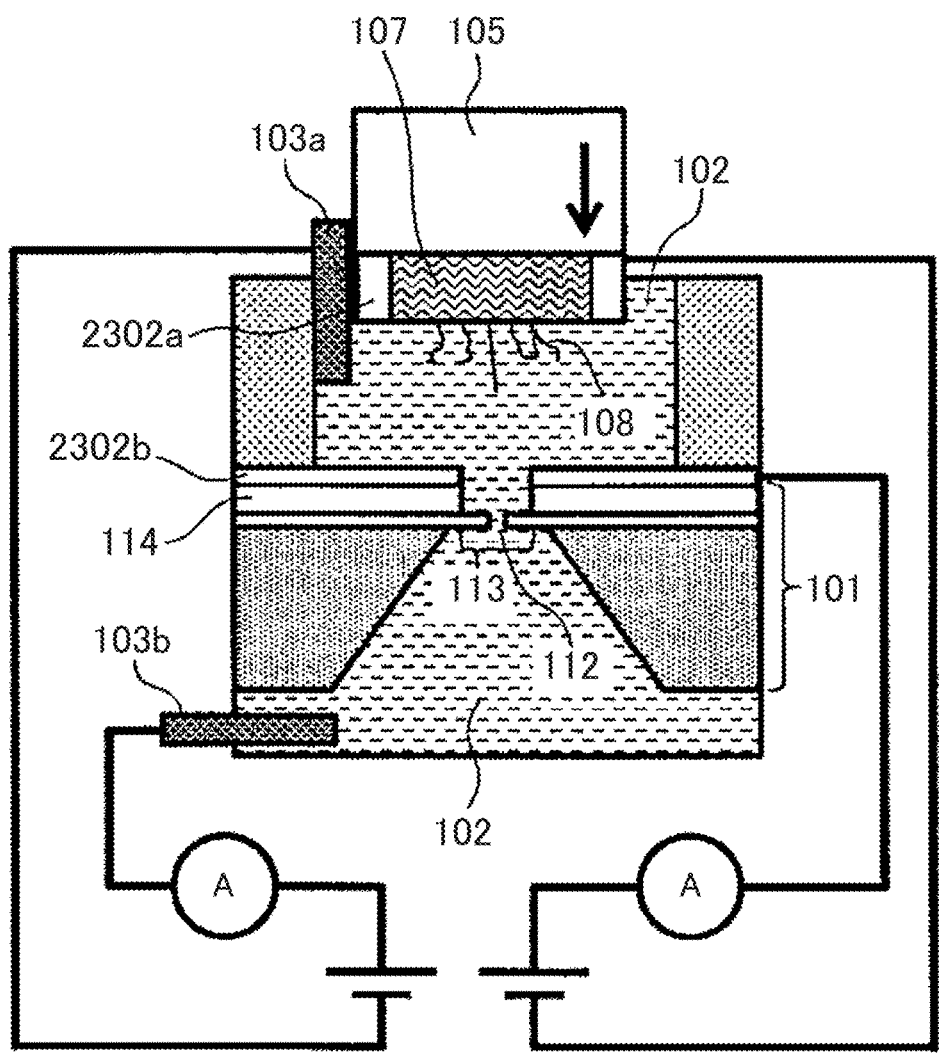
FIG. 61 is a schematic view illustrating a second example of the stop mechanism for preventing the contact between the immobilizing member and the thin film.
Figure 62:
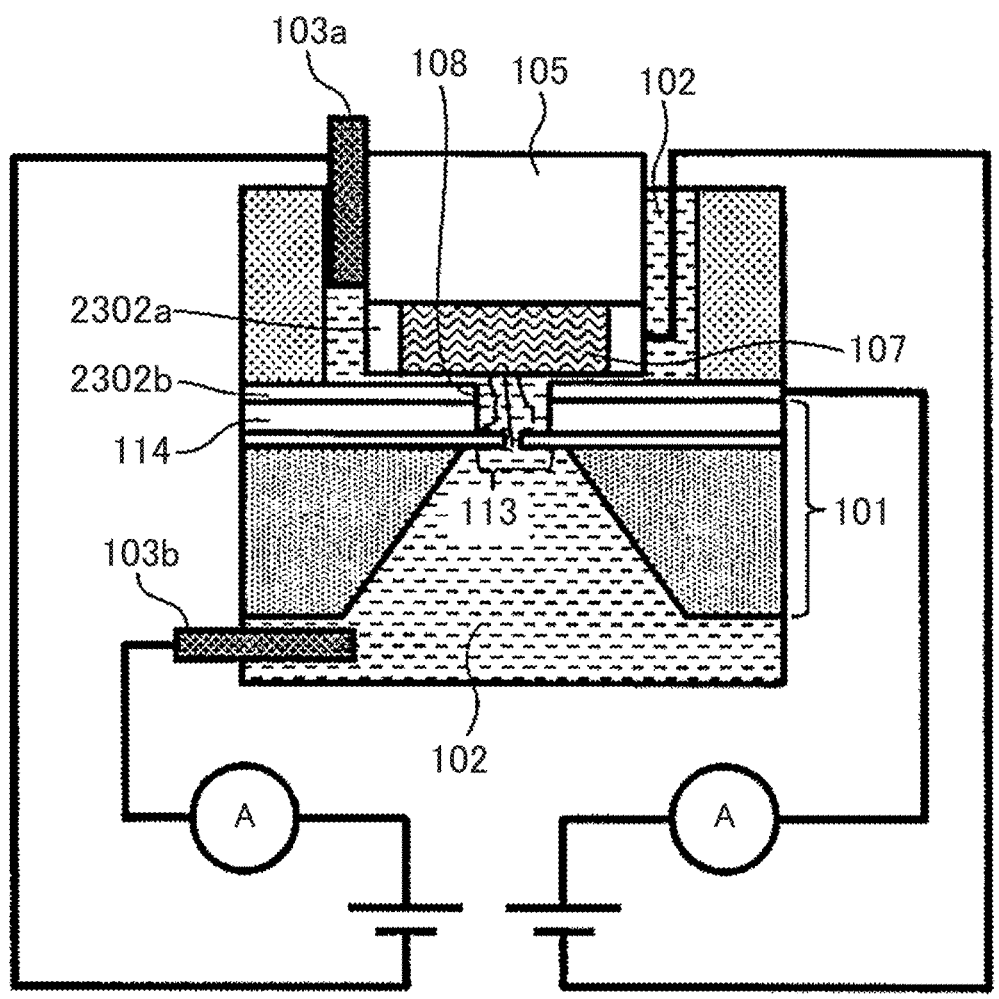
FIG. 62 is a schematic view illustrating the second example of the stop mechanism for preventing the contact between the immobilizing member and the thin film.

FIGS. 61 and 62 are schematic views showing a second example of the stop mechanism for preventing a contact between the immobilizing member and the thin film. For simplification of description, an illustration of the grooves 115 is omitted. FIG. 61 shows a state before the immobilizing member 107 comes into contact with the nanopore device 101 and FIG. 62 shows a state after the immobilizing member 107 comes into contact with the nanopore device 101. The stop mechanism is configured to provide a space for avoiding a contact between the immobilizing member 107 and the thin film 113, between the immobilizing member 107 and the thin film 113. The stop mechanism according to the present example is configured such that an electrode 2302a and an electrode 2302b are placed on an upper surface of the nanopore device 101 and at least a part of a lower surface of the immobilizing member 107 outside the region corresponding to the thin film, and a relative distance between the immobilizing member 107 and the nanopore device 101 is detected according to a change in electrostatic capacitance between the electrodes 2302a and 2302b to monitor that the contact between the immobilizing member 107 and the nanopore device 101. A voltage to be applied between the electrodes 2302a and 2302b is selected according to an assumed current amount and a measured current. In order to prevent corrosion and oxidation of the electrodes, measurement can be performed by applying a pulse voltage. The driving mechanism control unit 106 (not shown) causes the driving mechanism 105 to drive the immobilizing member 107 in the direction of the nanopore device 101, detects the distance between the nanopore device 101 and the immobilizing 107 based on the signal change obtained from the electrodes 2302a and 2302b when the nanopore device 101 and the immobilizing member 107 come closer to each other, and stops driving the driving mechanism 105. The driving mechanism control unit 106 can monitor the contact based on a short circuit instead of acquiring a signal of capacitance change. While the voltage is being applied between the electrodes 2302a and 2302b configuring the stop mechanism, no voltage is applied to the first and second electrodes 103a and 103b for measurement.

Figure 63:
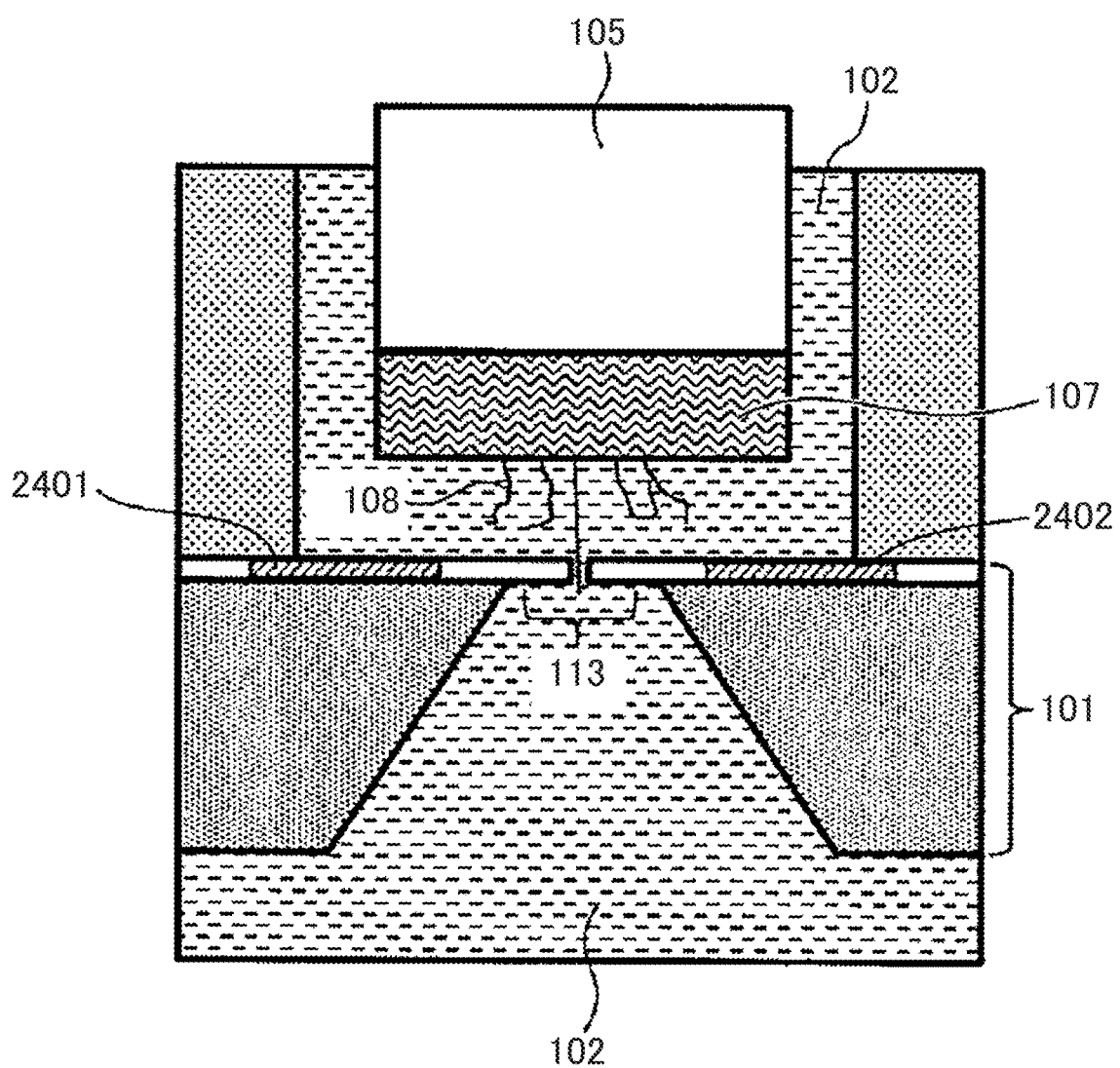
FIG. 63 is a schematic view illustrating a third example of the stop mechanism for preventing the contact between the immobilizing member and the thin film.
Figure 64:
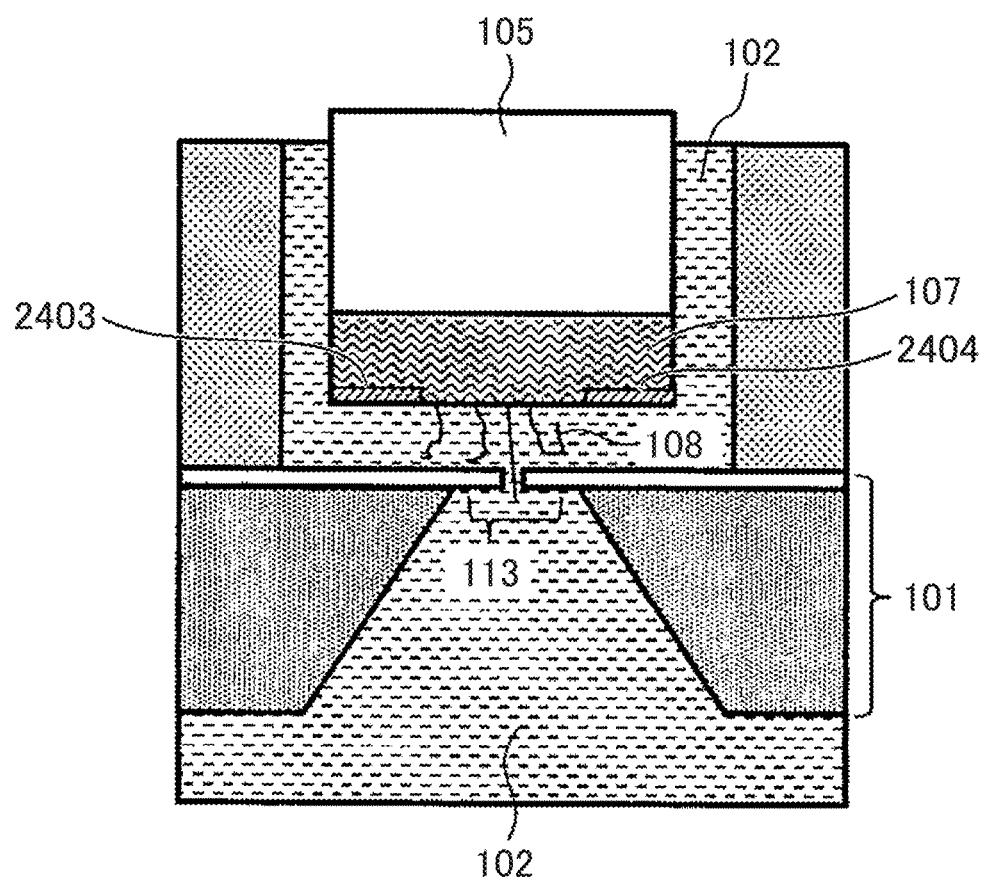
FIG. 64 is a schematic view illustrating the third example of the stop mechanism, for preventing the contact between the immobilizing member and the thin film.

FIGS. 63 and 64 are schematic diagrams illustrating a third example of the stop mechanism for preventing the contact between the immobilizing member and the thin film. For simplification of description, an illustration of the grooves 115 is omitted. In the example shown in FIG. 63, the electrodes 2401 and 2402 are disposed only on the nanopore device 101 and the electrodes are wired, and the relative distance between the immobilizing member 107 and the nanopore device 101 is detected according to a change in the current amount when the immobilizing member 107 comes closer to the nanopore device 101. The electrodes 2401 and 2402 are placed on an outer circumstance of a region outside the thin film 113, on four corners, or two opposite sides of the upper surface of the nanopore device 101. In the example shown in FIG. 64, electrodes 2403 and 2404 are placed on a lower surface of the immobilizing member 107, and those electrodes are wired to detect the relative distance between the immobilizing member 107 and the nanopore device 101 by the same mechanism. The electrodes 2403 and 2404 may be placed on four corners outside a region corresponding to the thin film 113 or two opposite sides on the lower surface of the immobilizing member 107. The grooves 115 may be provided on a side on which the electrodes 2401 and 2402 are disposed (the immobilizing member 107 or the nanopore device 101), or may be provided on a side where the electrodes 2401 and 2402 are not disposed (the immobilizing member 107 or the nanopore device 101).

In the case where four electrodes are disposed at the four corners, those four electrodes can also be used for equilibration of the immobilizing member 107. In that case, the driving mechanism 105 may have a tilt adjusting function, and the driving mechanism control unit 106 may adjust an inclination of the driving mechanism 105 so that current values acquired from the four portions substantially coincide with each other. For example, independent goniometers are provided at the four corners, and the inclination of the driving mechanism 105 may be manually or automatically adjusted based on the current values acquired from the four portions.

Figure 65:
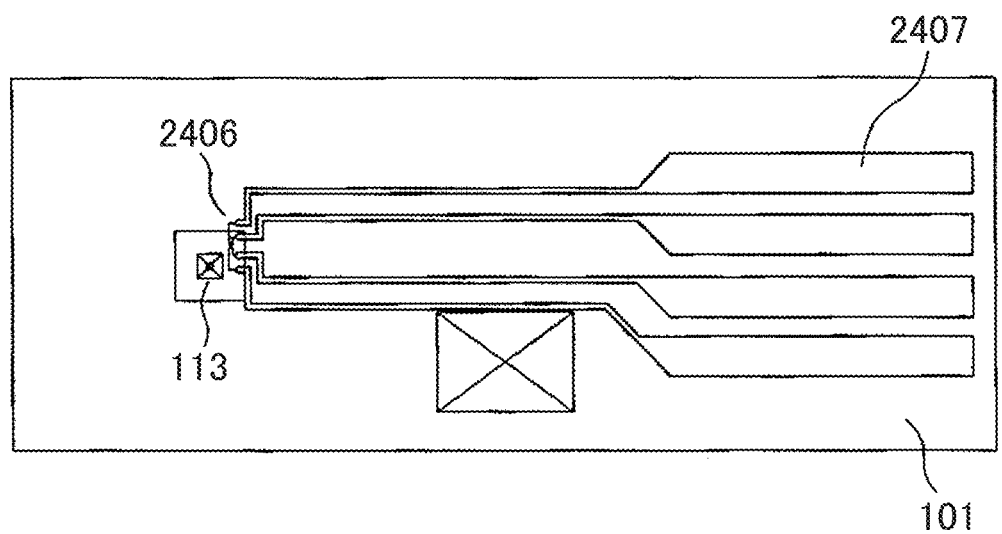
FIG. 65 is a schematic top view illustrating an electrode placement example on the nanopore device.
Figure 66:
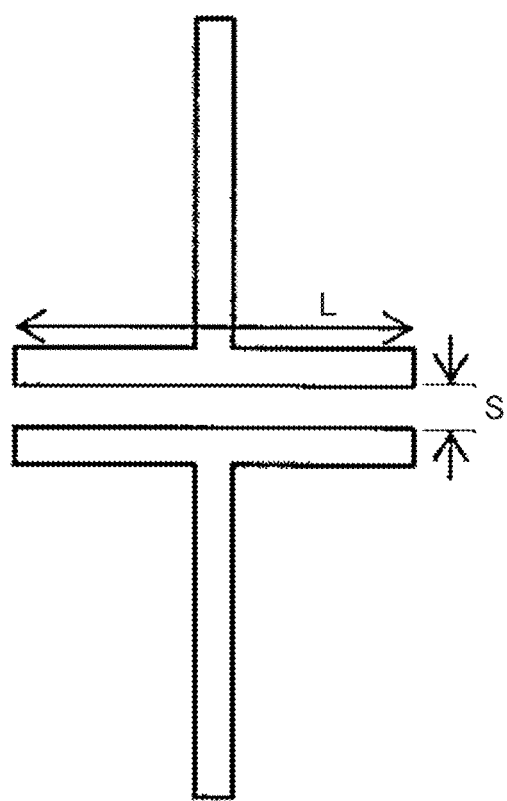
FIG. 66 is a diagram illustrating an example of a counter electrode in the electrode placement example on the nanopore device.
Figure 67:
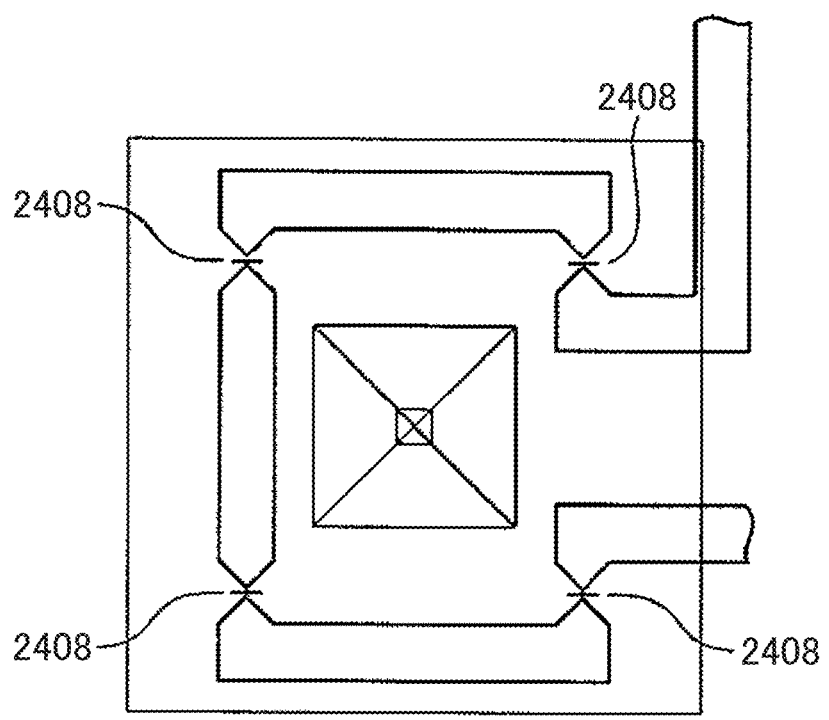
FIG. 67 is a schematic top view illustrating the electrode placement example on the nanopore device.

FIGS. 65 to 67 are schematic top views illustrating examples of electrode placement on the nanopore device 101 shown in FIG. 63. FIG. 65 is a layout view of the thin film 113, a sensor wiring 2406, and an electrode leading wire 2407 on the nanopore device 101. FIGS. 66 and 67 are enlarged views of the sensor wiring. FIG. 66 shows an example of a type of counter electrode, and FIG. 67 shows an example in which counter electrodes 2408 are placed in a ring shape at four positions in the peripheral portion of the thin film 113. In this example, a voltage of 1 V is applied between the electrodes designed to have an electrode length L of 10 µm and an electrode interval, s of 0.4 µm to 2 µm as shown in FIG. 66. Thereafter, a change in the current between the electrodes is monitored when the immobilizing member 107 is brought closer to the nanopore device 101.

Figure 68:
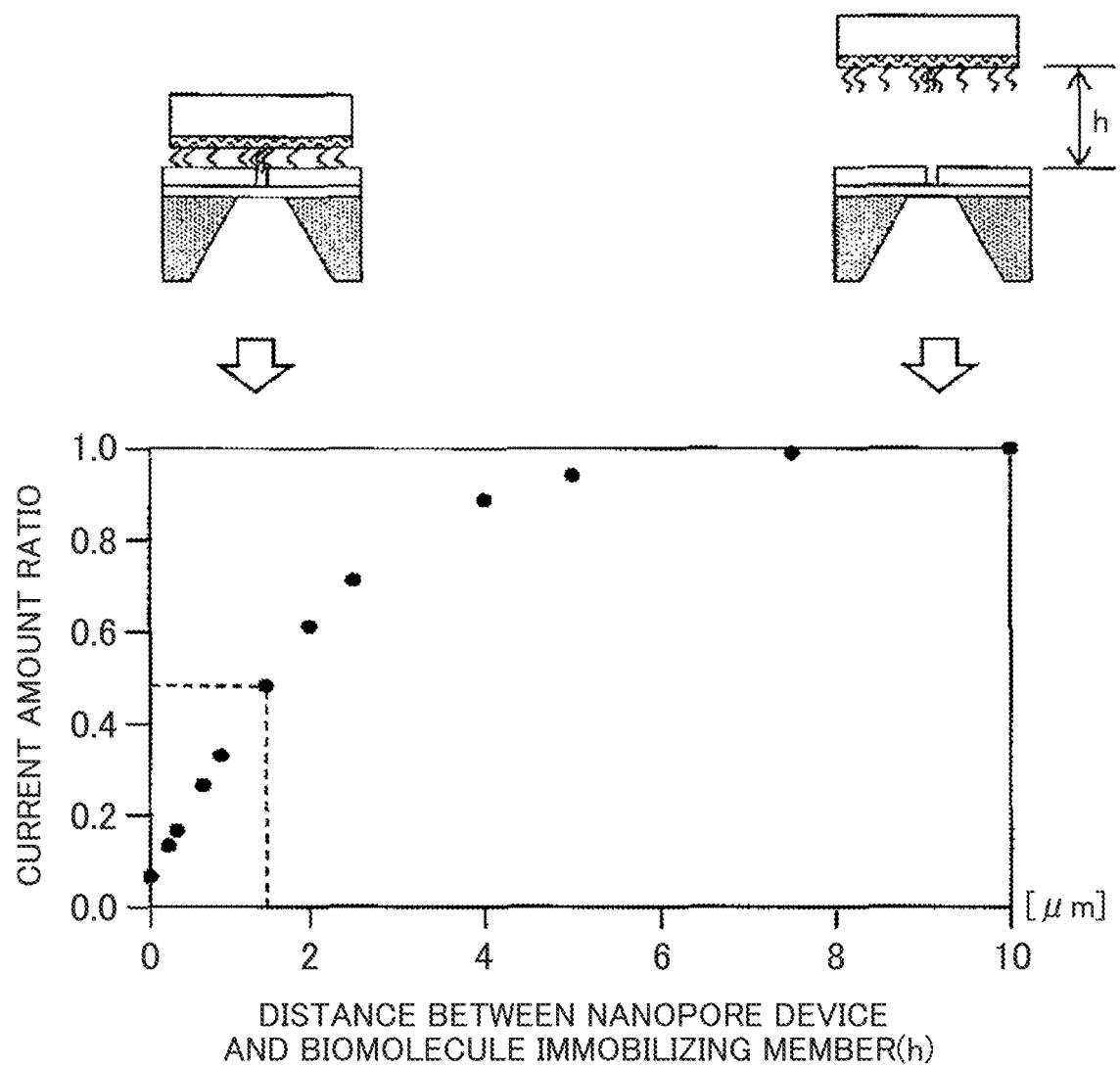
FIG. 68 is a graph showing a relationship; between a distance h between a biomolecule immobilizing member and the nanopore device and a current amount.

FIG. 68 is a graph showing a relationship between the distance h and the amount of current normalized by the amount of current flowing when the distance h between the immobilizing member and the nanopore device is 10 µm. As shown in FIG. 68, it has been found that there is almost no dependence of the amount of current on the distance h when the distance between the immobilizing member 107 and the nanopore device 101 is equal to or more than 7 µm, but there is a correlation between the distance and the amount of current reduction when the distance is equal to or less than 7 µm. Therefore, the correlation between the distance h and the amount of current is acquired, thereby being capable of adjusting the height of the immobilizing member 107 can be adjusted.

As another example of the method of driving the immobilizing member 107, there is also a method of approaching the vicinity of the nanopore while preliminarily stretching the biomolecules 108 on the immobilizing member 107. FIGS. 69 to 72 and 73 to 74 are schematic cross-sectional views showing an example of a method of driving the immobilizing member by the biomolecule measuring device having a preliminary stretching mechanism of the biomolecules. For facilitation of description, an illustration of the grooves 115 is omitted.

Figure 69:
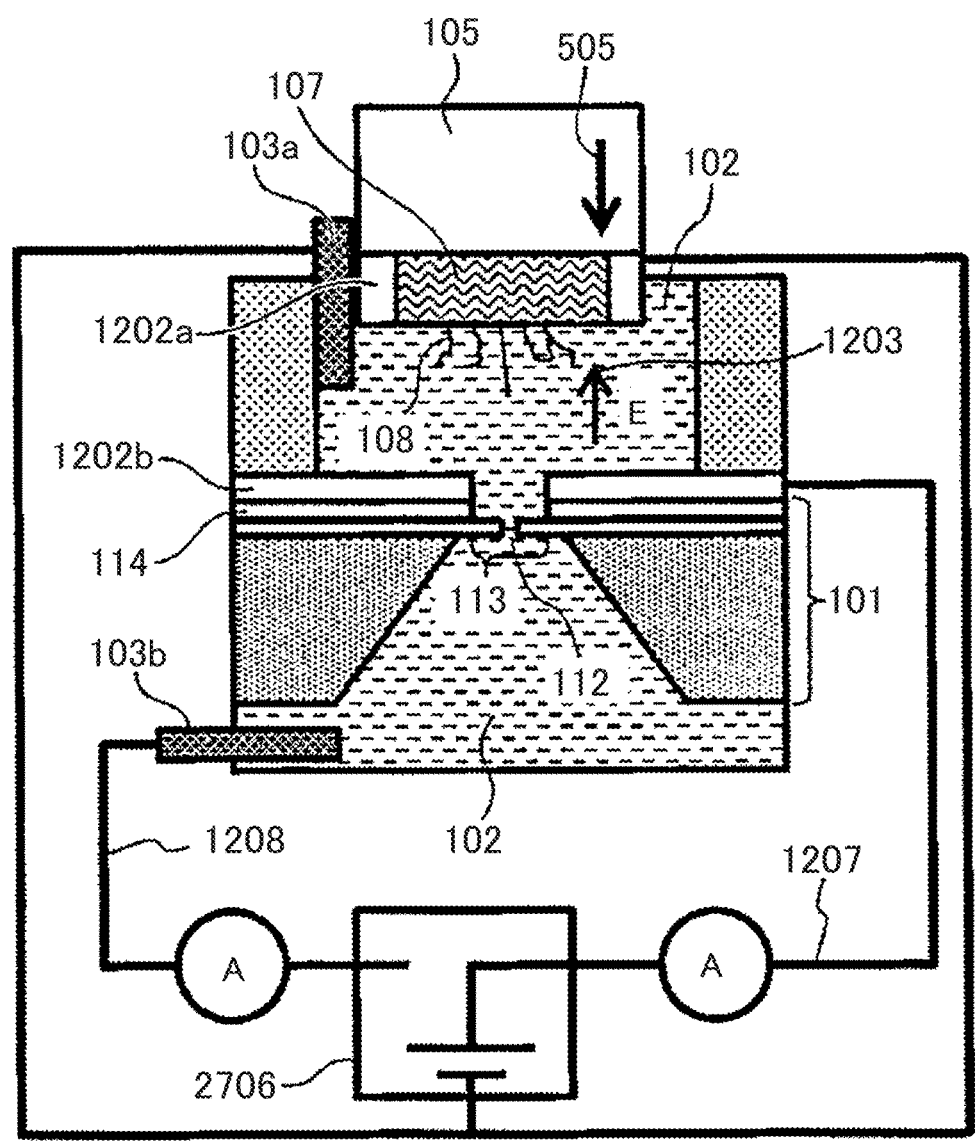
FIG. 69 is a schematic cross-sectional view illustrating an example of the biomolecule measuring device having a biomolecule preliminary drawing mechanism.

As shown in FIG. 69, the biomolecule measuring device according to the present example includes electrodes 1202a and 1202b placed on the immobilizing member 107 and the nanopore device 101, respectively. First, a circuit conversion controller 2706 connects a power supply to a circuit 1207 connected to the electrodes 1202a and 1202b, and creates a potential gradient 1203 between the immobilizing member 107 and the nanopore device 101. Then, the potential gradient 1203 causes the negatively charged biomolecules 108 to be stretched between the immobilizing member 107 and the nanopore device 101.

Figure 70:
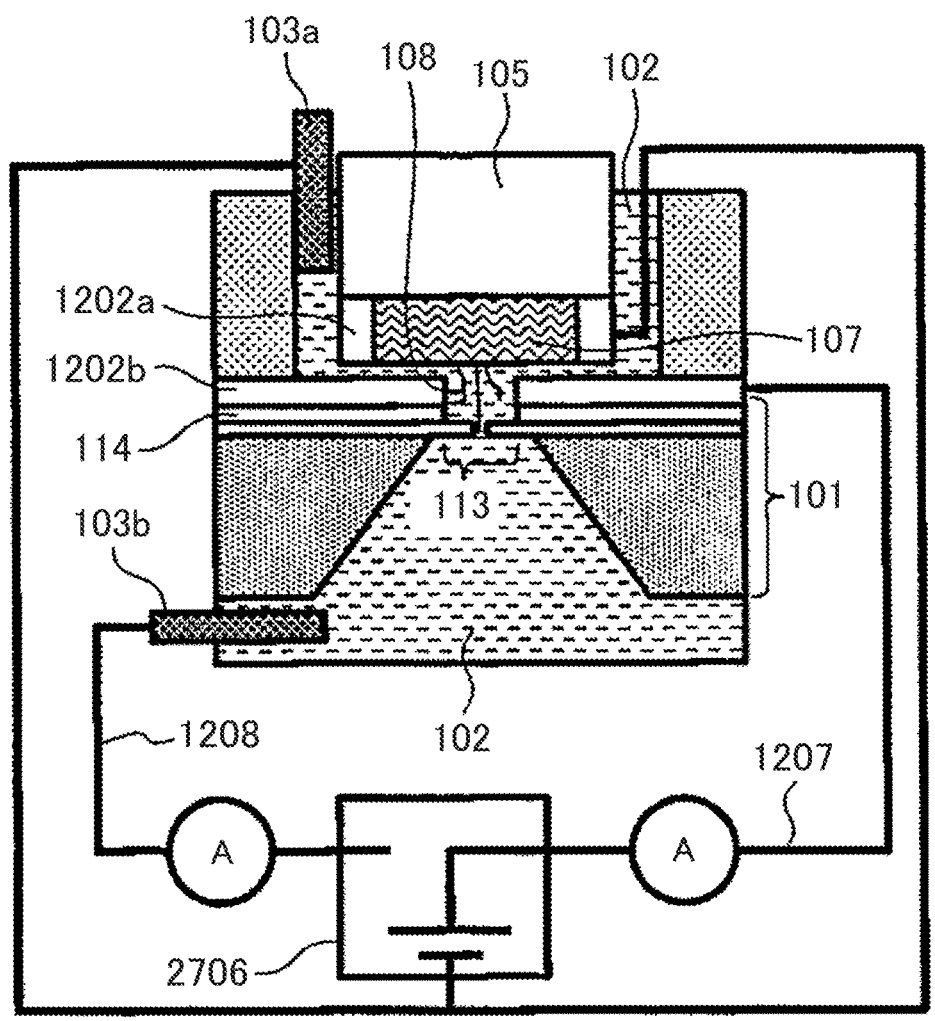
FIG. 70 is a schematic cross-sectional view illustrating the example of the biomolecule measuring device having the biomolecule preliminary drawing mechanism.
Figure 71:
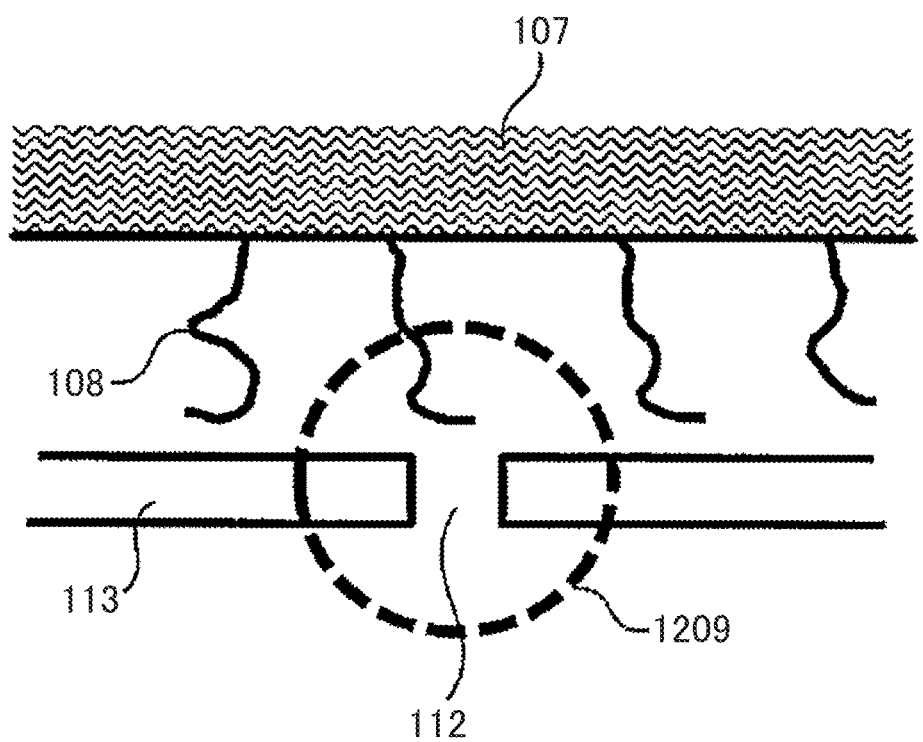
FIG. 71 is a diagram illustrating the biomolecule measuring device having the biomolecule preliminary drawing mechanism, which is an enlarged view of the vicinity of the nanopore.

Next, as shown in FIG. 70, the driving mechanism 105 is driven to drive the immobilizing member 107 downward until the immobilizing member 107 comes into contact with the space defining member 114 of the nanopore device 101. At this time, as shown in the enlarged view of FIG. 71, the biomolecules 108 are placed within a range of an assumed electric field 1209 which should be generated around the nanopore when the power source is connected to a circuit 1208 connected to the first and second electrodes 103a and 103b.

Figure 73:
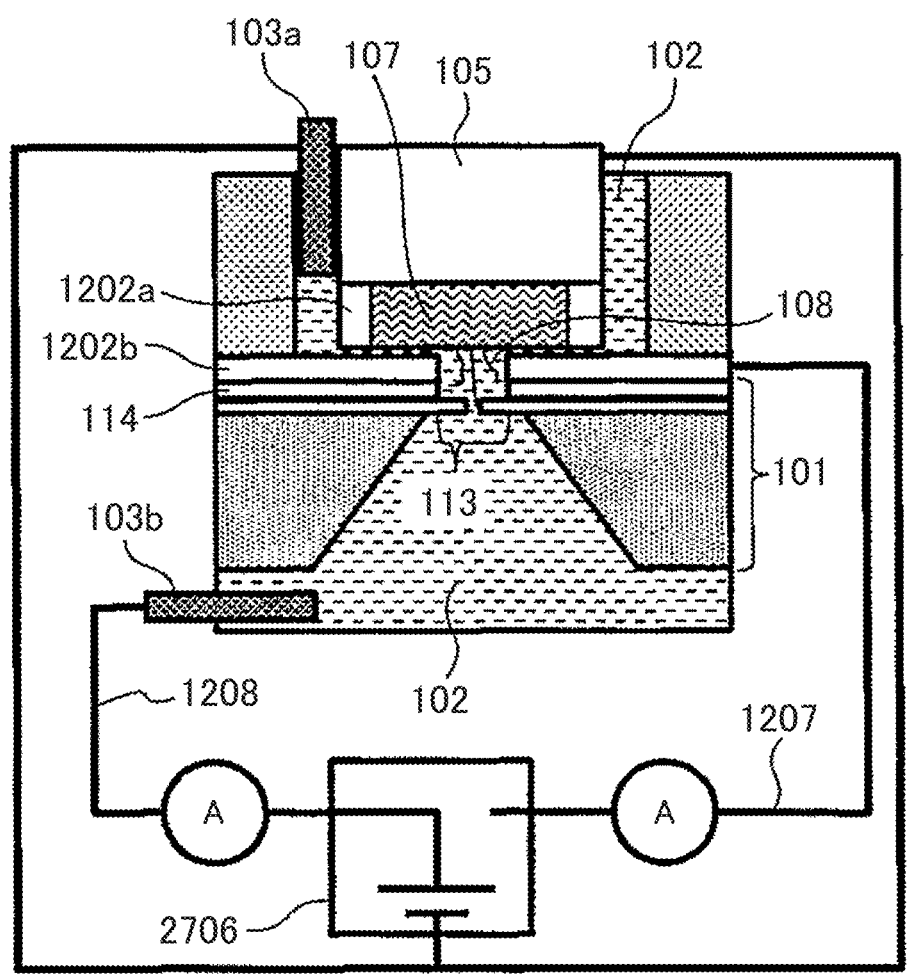
FIG. 73 is a schematic cross-sectional view illustrating an example of the biomolecule measuring device having the biomolecule preliminary drawing mechanism.
Figure 74:
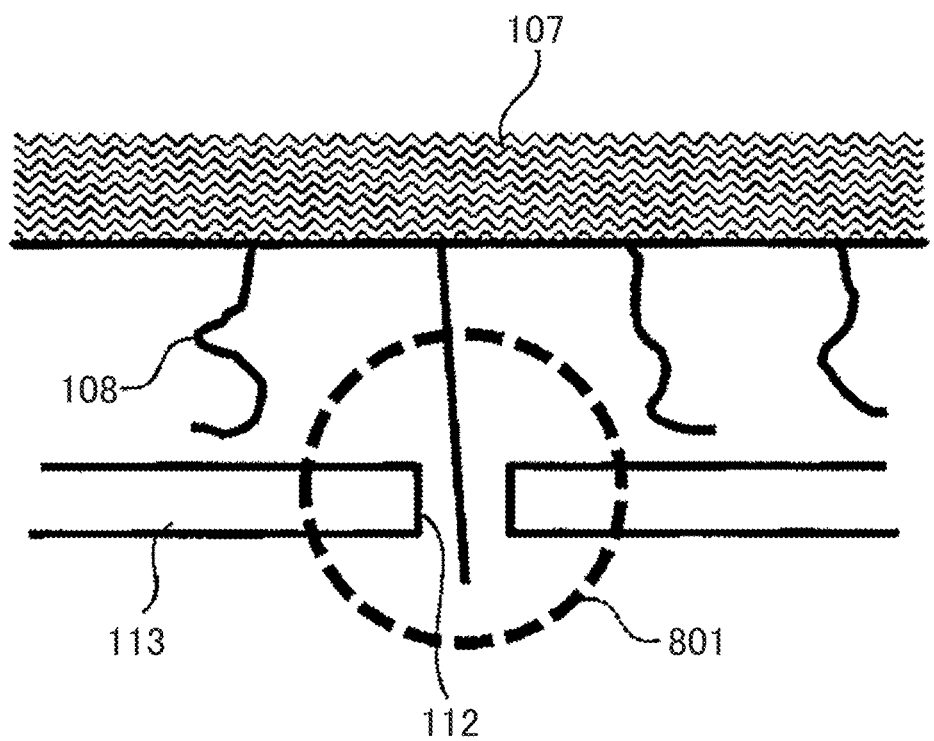
FIG. 74 is a diagram illustrating the biomolecule measuring device having the biomolecule preliminary drawing mechanism, which is an enlarged view of the vicinity of the nanopore.

Next, as shown in FIG. 73, when the immobilizing member 107 comes into contact with the space defining member 114 of the nanopore device 101, the connection of the power supply is switched from the circuit 1207 connected to the electrodes 1202a and 1202b to the circuit 1208 that generates the electric field around the nanopore. As shown in FIG. 74, the potential gradient 801 is formed around the nanopore with the result that a tip of the biomolecule 108 is inserted into the nanopore.

Figure 72:
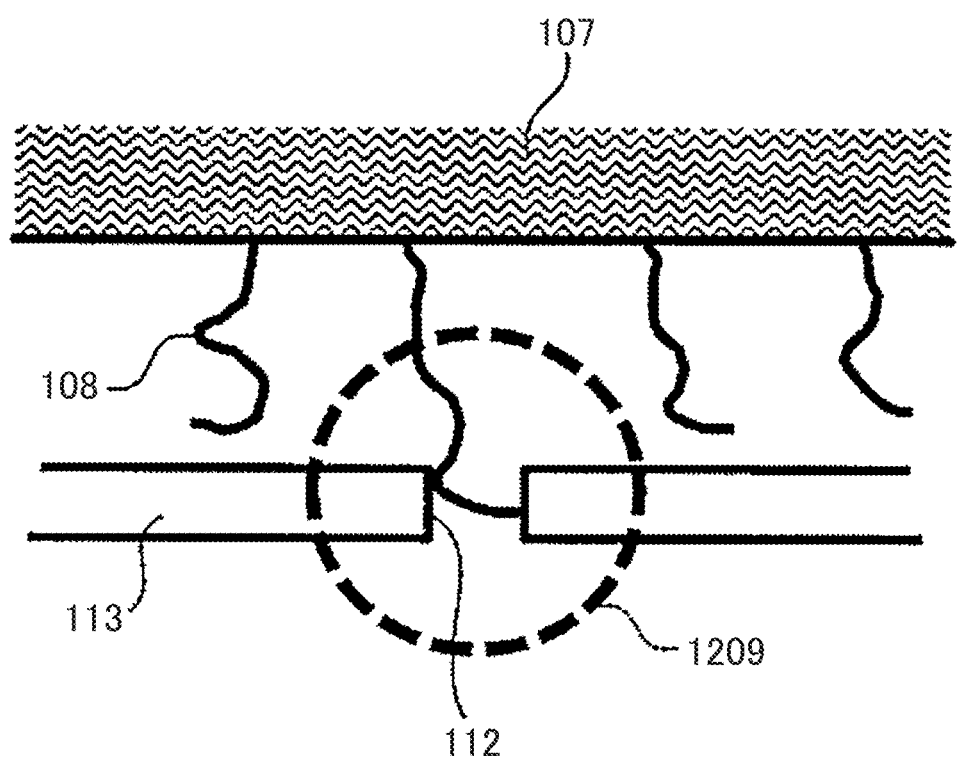
FIG. 72 is a diagram illustrating the biomolecule measuring device having the biomolecule preliminary drawing mechanism, which is an enlarged view of the vicinity of the nanopore.

After the step shown in FIG. 70, there are a case where the tip of the biomolecule 108 does not enter the nanopore 112 and a case where the tip of the biomolecule 108 enters the nanopore 112 as shown in the enlarged view of FIG. 72 although a probability of the entrance is low. The base can be read from the tip of the biomolecule 108 only when the tip of the biomolecule 108 falls within the electric field region without entering the nanopore 112.

Figure 75:
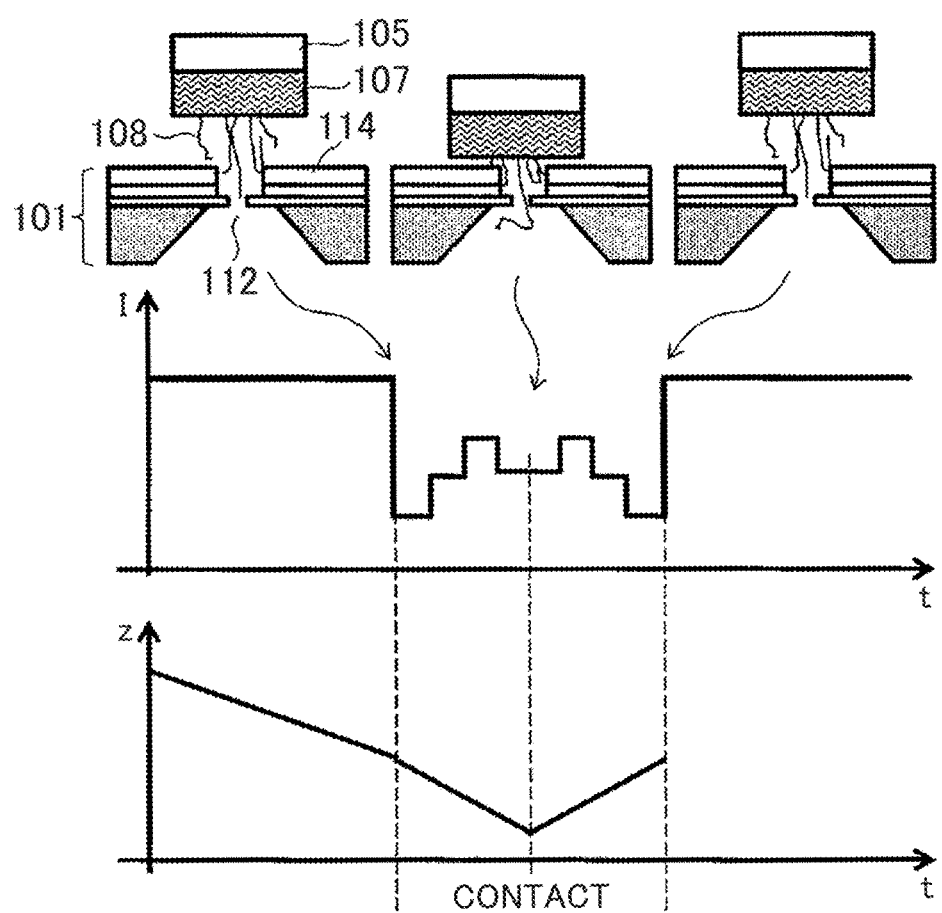
FIG. 75 is a schematic view illustrating an example of a signal read from a tip of the biomolecule.

FIG. 75 is a schematic diagram showing an example of a signal read from the tip of the biomolecule. FIG. 75 shows a graph of a change in the ionic current signal in a middle stage, and shows a graph of a displacement of the driving mechanism in a lower stage. A driving mechanism displacement z in the lower stage corresponds to the distance between the nanopore device 101 and the immobilizing member 107. The correspondence between the immobilizing member 107 and the nanopore device 101 shown in the upper stage is indicated by arrows with respect to the feature points in the ionic current signal.

Before the immobilizing member 107 comes closer to the nanopore device 101, an ionic current signal $I_0$ corresponding to the nanopore diameter is obtained. When the power supply is connected to the first and second electrodes 103a and 103b to form the potential gradient 801 around the nanopore, the tip of the biomolecule 108 falls within the potential gradient 801 (refer to FIG. 74). Therefore, when the driving mechanism 105 is driven downward in the z-axis, the biomolecules 108 are successively introduced from free ends of the biomolecules 108 into the nanopore 112. In this situation, since the biomolecules 108 do not have deflection, the biomolecules 108 are driven at a speed set by the driving mechanism control unit 106, and the characteristic analysis corresponding to each sequence of the biomolecules 108 is enabled. Therefore, a signal read during a time since the biomolecule 108 is introduced into the nanopore 112 until the immobilizing member 107 and the nanopore device 101 come into contact with each other and a signal read during a time since the driving mechanism 105 starts to be driven upward in the z-direction until the tip of the biomolecule exits the nanopore 112 are symmetrical with respect to the contact time, as shown in FIG. 75.

Figure 76:
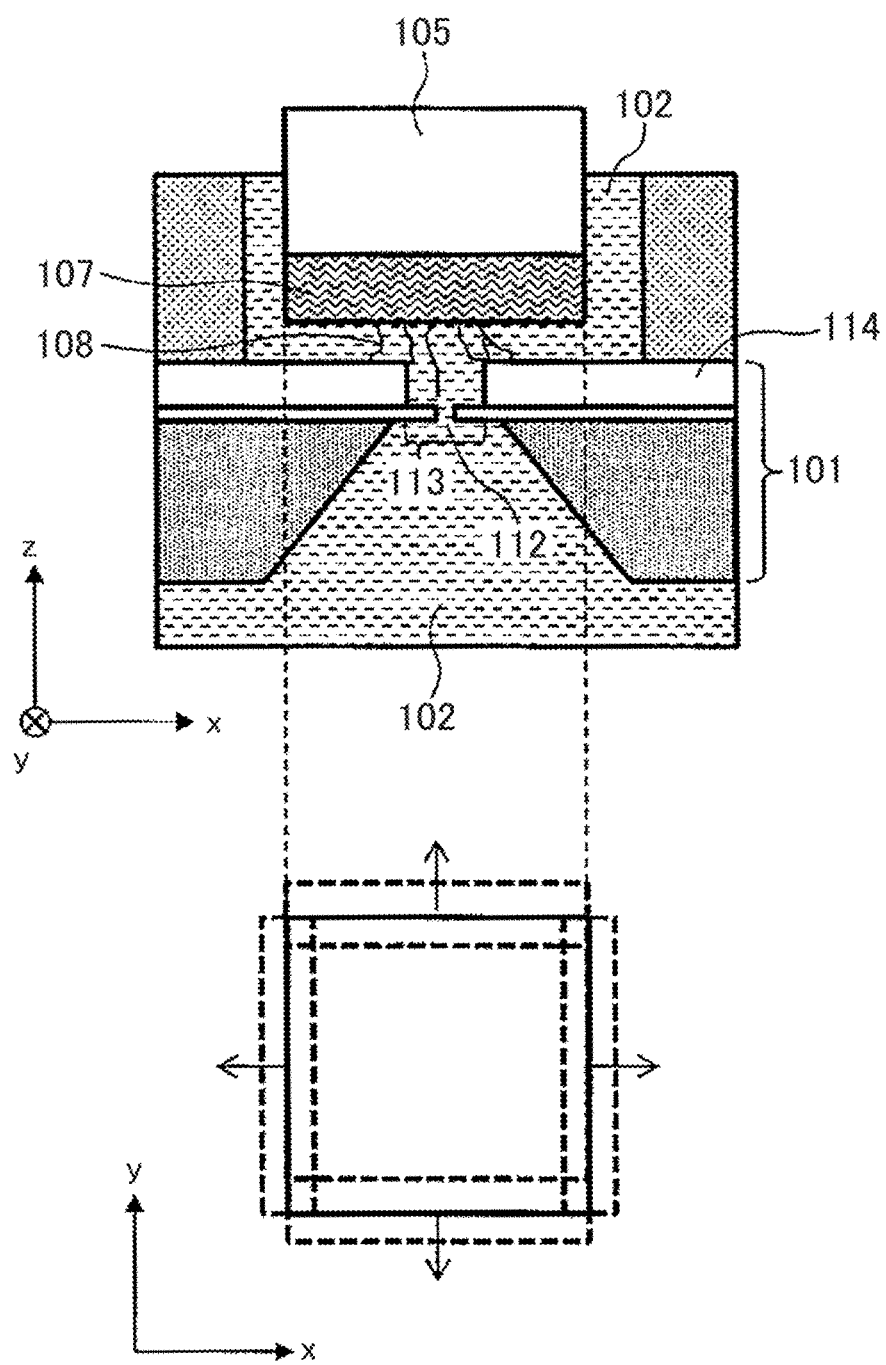
FIG. 76 is a schematic cross-sectional view of a part of the biomolecule measuring device and a schematic top view of the driving mechanism.

Reading of biomolecule 108 different from another biomolecule 108 initially measured among the multiple biomolecules 108 immobilized on the immobilizing member 107 can be realized by driving the driving mechanism 105 in the xy direction. FIG. 76 is a schematic cross-sectional view of a part of the biomolecule measuring device and a schematic top view of the driving mechanism 105. As shown in the schematic top view, the driving mechanism 105 is driven in the xy direction, that is, in a direction parallel to the surface of the thin film 113, thereby being capable of allowing another biomolecule 108 to pass through the nanopore 112 and analysis of the multiple biomolecules on the immobilizing member 107 is realized.

Figure 77:
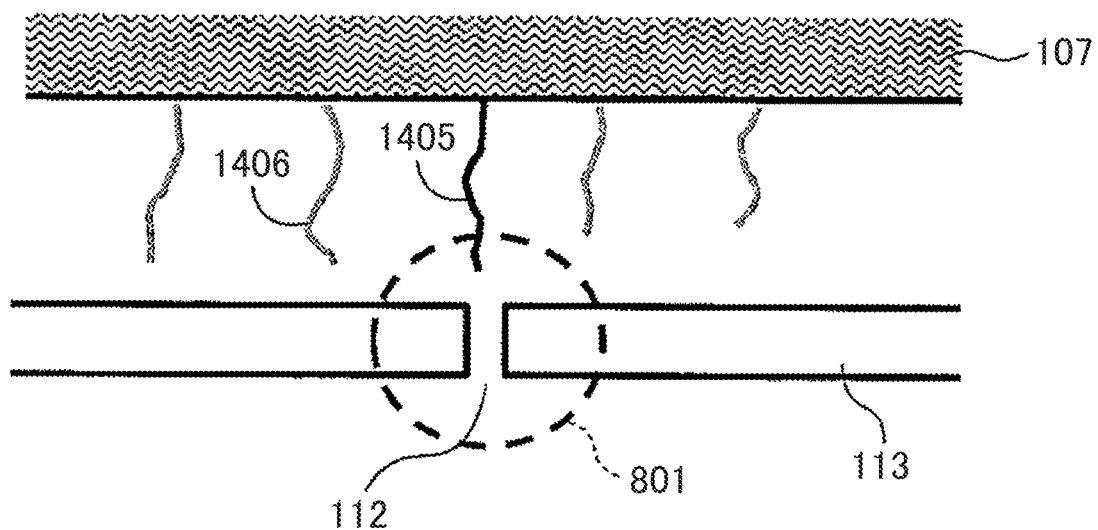
FIG. 77 is an enlarged, view of the vicinity of the nanopore illustrating an analysis of multiple biomolecules.
Figure 78:
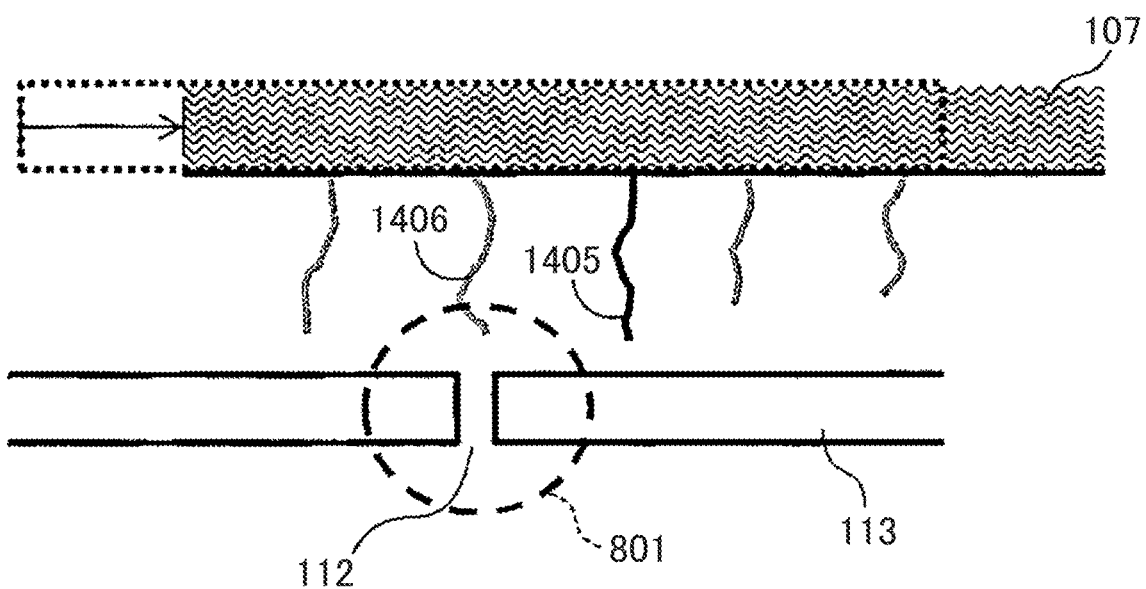
FIG. 78 is an enlarged view of the vicinity of the nanopore illustrating the analysis of multiple biomolecules.

Conditions for realizing analysis of the multiple biomolecules will be described with reference to enlarged views of the vicinity of the nanopores shown in FIGS. 77 and 78. FIG. 77 is a schematic cross-sectional view showing a positional relationship between the thin film 113 having the nanopore 112 and the immobilizing member 107 when a characteristic analysis of a first biomolecule 1405 is performed. In this example, when a second biomolecule 1406 is analyzed, the driving mechanism 105 causes the immobilizing member 107 to move in parallel to the surface of the thin film 113 by the same diameter as a diameter of the potential gradient 801. FIG. 78 is a schematic cross-sectional view showing the positional relationship between the thin film 113 having the nanopore 112 after the movement and the immobilizing member 107. The movement makes it possible to create a state in which the first biomolecule 1405 does not fall within the range of the potential gradient 801 at all. Thereafter, the driving mechanism 105 causes the immobilizing member 107 to be driven toward the thin film 113, thereby being capable of introducing the second biomolecule 1406 into the nanopore 112 and analyzing the second biomolecule 1406.

Example 5

An example of a procedure for measuring a biomolecule with the use of a biomolecule measuring device will be described below. In all of the following steps, an ionic current I flowing through a nanopore is measured through an amplifier. In addition, a constant voltage is applied between a pair of Ag and AgCl electrodes inserted respectively in two upper and lower liquid tanks, and an ion current amount $I_0$ corresponding to the size of the nanopore is acquired.

Figure 79:
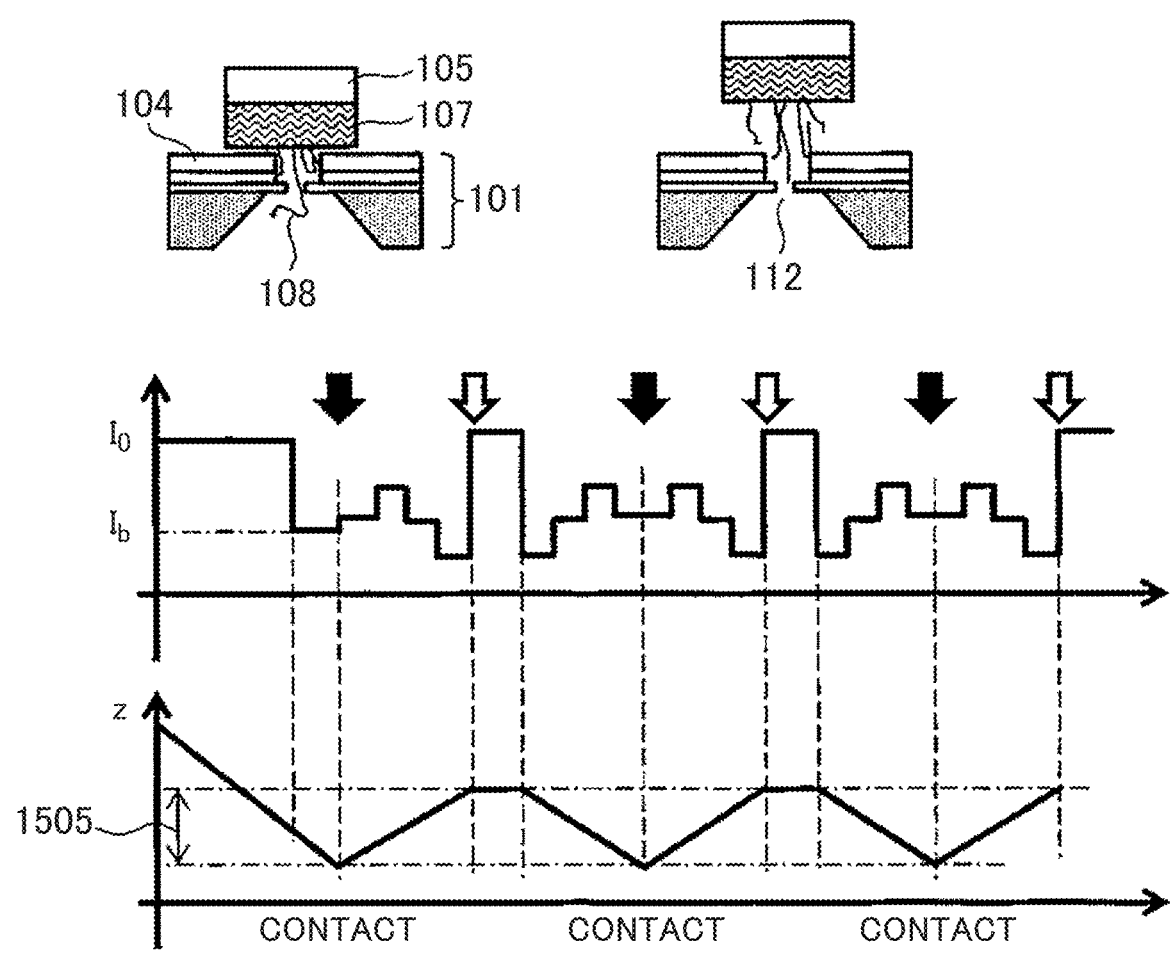
FIG. 79 is an illustrative view illustrating an example of a method of reading a DNA base sequence.

FIG. 79 is an illustrative view showing an example of a method of reading a base sequence of a DNA as a biomolecule. An upper stage of FIG. 79 shows representative two positional relationships between an immobilizing member 107 and a nanopore device 101 during DNA base sequence analysis. A middle stage of FIG. 79 shows a change in the ion current, and a lower stage shows a displacement of the immobilizing member 107. A displacement z in the lower stage corresponds to a distance between the immobilizing member 107 and the nanopore device 101. Also, FIG. 79 shows time points at which to change a direction of driving the immobilizing member 107 by the driving mechanism 105 and positional relationships between the immobilizing member 107 and the nanopore device 101 at the time of changing the direction. Solid arrows in the middle stage indicate a first positional relationship shown on the left side of the upper stage, and hollow arrows indicate a second positional relationship shown on the right side of the upper stage.

When the immobilizing member 107 is driven downward in the z axis by the driving mechanism 105, the free end of the biomolecule 108 enters the nanopore 112, and the biomolecule 108 is stretched between the end immobilized on the immobilizing member 107 and the nanopore 112. At that time, the ion current decreases according to an average diameter size of the biomolecules 108 and becomes $I_b$. When the biomolecules 108 fall within the potential gradient 801 from the outside, since the biomolecules 108 are folded, the biomolecules 108 pass through the inside of the nanopore 112 at a speed of the free electrophoresis of the biomolecules 108 instead of the moving speed of the immobilizing member 107. The ion current value at that time is not a current value derived from each base but indicates an average current value $I_b$ depending on the average diameter of the biomolecules 108.

Thereafter, the immobilizing member 107 is further driven downward in the z-axis by the driving mechanism 105, but the movement of the immobilizing member 107 downward in the z axis is blocked by the space defining member 114, and the movement stops. At this time, the positional relationship of the immobilizing member 107, the biomolecules 108, and the nanopore device 101 are shown as the first positional relationship on the left side of the upper stage in FIG. 79.

Thereafter, since a transporting speed of the biomolecules 108 when lifting the biomolecules 108 is equal to the driving speed of the immobilizing member 107, the biomolecules 108 can be transported at a rate (<3.4 nm/ms) necessary for single base decomposition. Therefore, a signal reflecting the base sequence of the biomolecules 108 is obtained. In the process of driving the immobilizing member 107 upward in the z-axis by the driving mechanism 105 in this way, the sequence information on the biomolecules 108 that are moving in the nanopore 112 can be read. As long as the free end not immobilized of the biomolecule 108 exits from the nanopore 112 and falls within the potential gradient 801 around the nanopore, the biomolecule 108 receives forces in opposite directions from both of the immobilizing member 107 and the potential gradient 801 around the nanopore, and are stretched. A relationship among the immobilizing member 107, the biomolecules 108, and the nanopore device 101 at that time is shown as the second positional relationship on the right side of the upper stage of FIG. 79. Since the biomolecule 108 exits from the nanopore 112, the ion current amount returns to $I_0$. A change in the current value is detected to stop the driving of the immobilizing member 107 by the driving mechanism 105.

The immobilizing member 107 is again driven downward in the z axis by the driving mechanism 105 to cause the biomolecule 108 to pass through the nanopore 112 from the free end while the base sequence of the biomolecule 108 is read. At this time, the biomolecule 108 is stretched as a whole because the other free end of the biomolecule 108 falls within the potential gradient 801 in a state where one end of the biomolecule 108 is immobilized on the immobilizing member 107. Therefore, since the biomolecules 108 pass through the nanopore 112 from the free end of the biomolecule 108 at a driving speed by the driving mechanism 105, the signal can be read with high precision. In addition, the sequence read during the driving upward in the z axis is read from the reverse direction, and the ion current that changes symmetrically reflecting the reverse reading is measured. When the immobilizing member 107 again comes into contact with the space defining member 114, the driving of the immobilizing member 107 stops.

In the subsequent process, with the repetition of driving upward and downward, the signal is repeatedly read until a required sequence reading accuracy is obtained. A displacement 1530 from a position where the immobilizing member 107 comes into contact with the nanopore device 101 to a position where the ion current value becomes $I_0$ reflects the length of the biomolecules 108.

Example 6

Next, an example in which biomolecule measuring devices are disposed in parallel to each other will be described. The biomolecule measuring device described above is excellent in compatibility with parallelized nanopore devices. Since the biomolecules of the same type can be measured by the parallelization at the same time, an improvement of throughput can be performed. This example shows three examples of parallelization.

Figure 81:
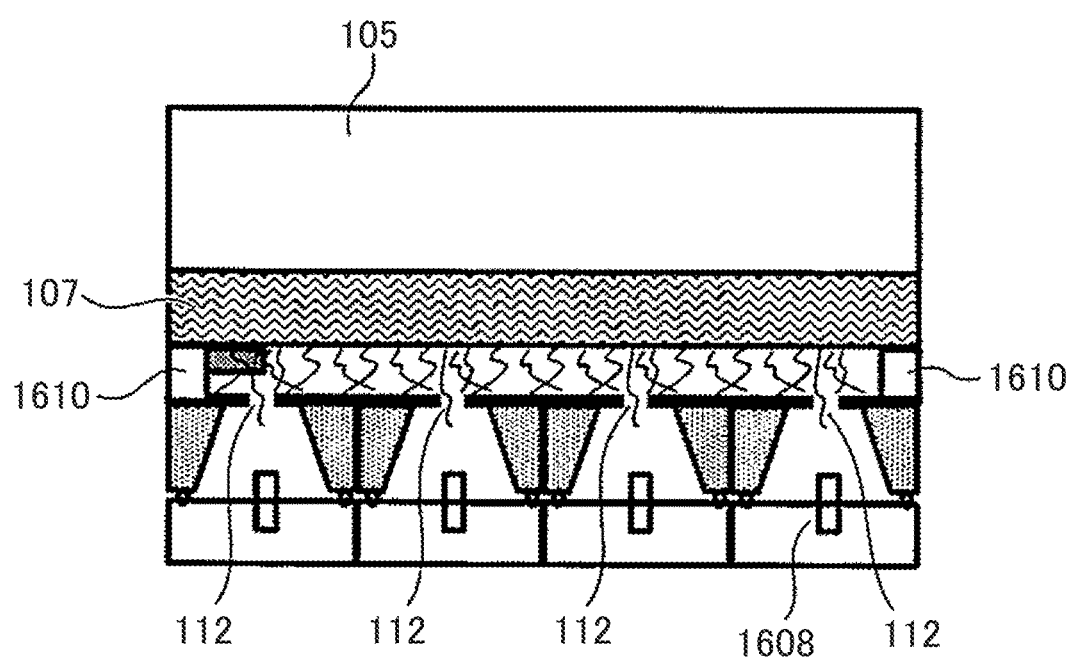
FIG. 81 is a schematic cross-sectional view illustrating the first example of the biomolecule measuring device having the parallelized, nanopore devices.

FIGS. 80 and 81 are schematic cross-sectional views showing a first example of a biomolecule measuring device having parallelized nanopore devices. An illustration of the grooves 115 is omitted for the sake of simplification of description. In this example, as shown in FIG. 80, the multiple nanopore devices 1604 are placed adjacent to each other in a lateral direction, and a single common driving mechanism 105 and an immobilizing member 107 are disposed above the multiple nanopore devices 1604. The immobilizing member 107 has an area to cover the whole of the multiple nanopore devices 1604. Each of the multiple parallelized nanopore devices 1604 has an independent liquid tank, and the liquid tank of each nanopore device 1604 is provided with one array electrode 1608, and the array electrode 1608 is connected to each amplifier. One liquid tank is commonly provided on the top of the multiple parallelized nanopore devices 1604 and a common electrode 1609 is disposed for an array electrode 1608 in the liquid tank. A space defining member 1610 common to the multiple nanopore devices 1604 is placed on a side of the parallelized nanopore devices 1604. The liquid tank provided in each individual nanopore device 1604 communicates with an upper liquid tank through each nanopore 112 provided in the nanopore device 1604.

The multiple biomolecules 108 are bound to a lower surface of the immobilizing member 107. As shown in FIG. 81, when the driving mechanism 105 is descended downward in the z axis, the biomolecules 108 on the immobilizing member 107 pass through the nanopores 112 provided in the respective nanopore devices 1604. According to the above configuration, since the multiple biomolecules can be measured concurrently with the use of the multiple nanopores 112, the measurement throughput is improved.

Figure 82:
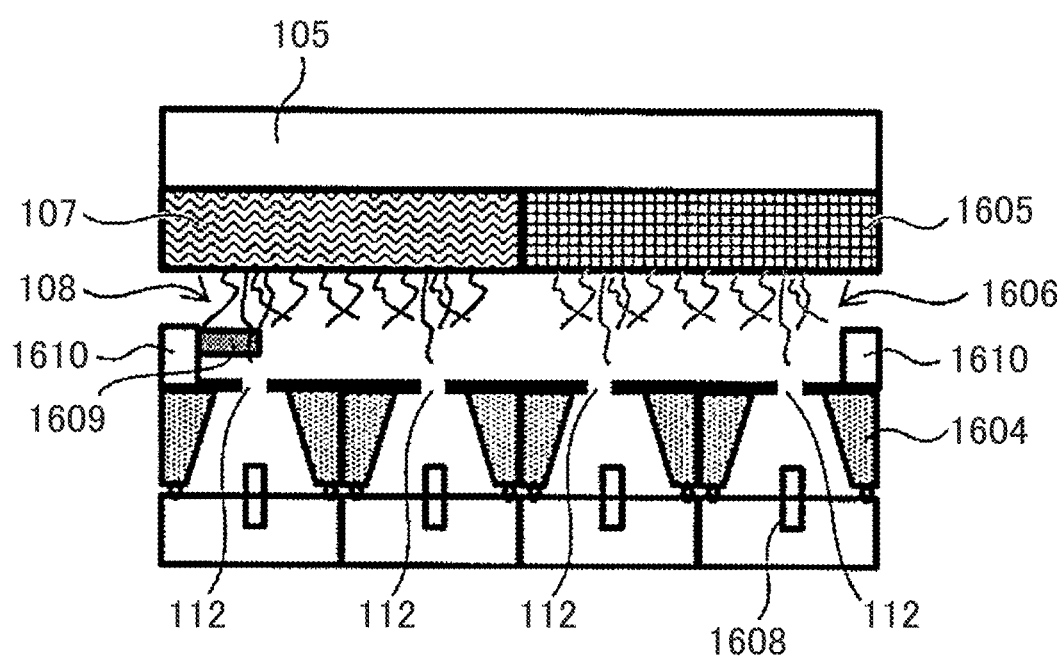
FIG. 82 is a schematic cross-sectional view illustrating a second example of the biomolecule measuring device having parallelized nanopore devices.
Figure 83:
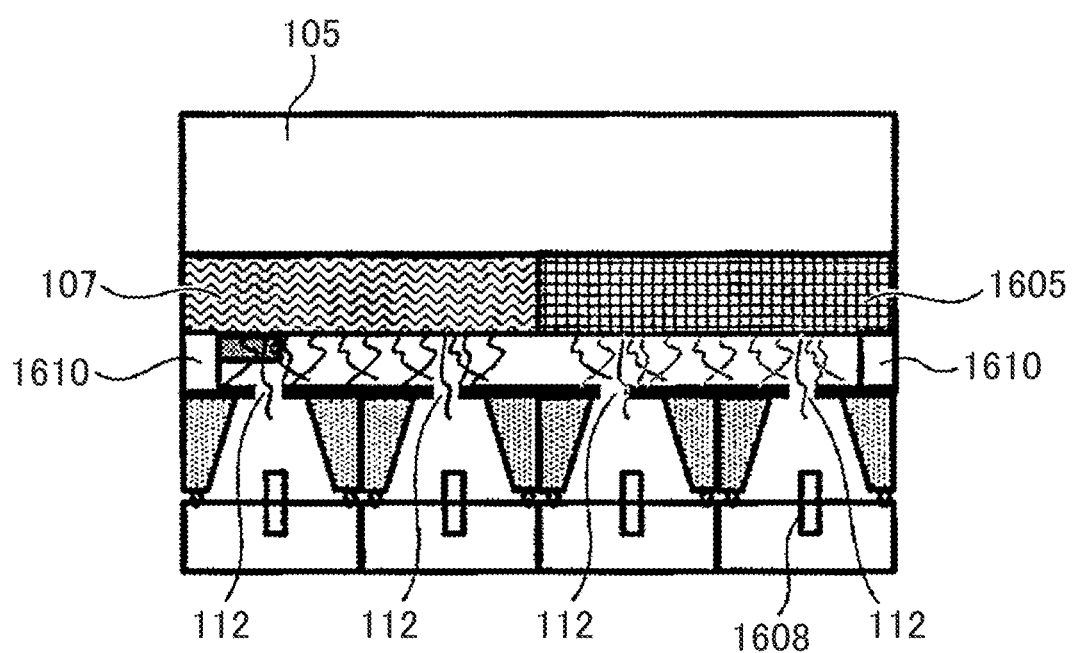
FIG. 83 is a schematic cross-sectional view illustrating the second example of the biomolecule measuring device having parallelized nanopore devices.

FIGS. 82 and 83 are schematic cross-sectional views showing a second example of a biomolecule measuring device having parallelized nanopore devices. An illustration of the grooves 115 is omitted for simplification of description. In this example, as shown in FIG. 82, one driving mechanism 105 is disposed above the multiple aligned nanopore devices 1604. An array electrode 1608 is connected to each of the nanopore devices 1604. One liquid tank, is commonly provided on the top of the multiple nanopore devices 1604, and a common electrode 1609 is disposed for the respective array electrodes 1608. A space defining member 1610 common to the multiple nanopore devices 1604 is provided on the side of the parallelized nanopore devices 1604. The driving mechanism 105 is connected with the multiple immobilizing members, and each different type of biomolecule is immobilized. As a result, the characteristic analysis of the different biomolecules can be realized at the same time.

In the illustrated example, two biomolecule immobilizing members including a first immobilizing member 107 and a second immobilizing member 1605, are connected to the driving mechanism 105. The first immobilizing member 107 is coupled with the first biomolecules 108 and the second immobilizing member 1605 is coupled with the second biomolecules 1606. According to the present configuration, not only the multiple nanopores 112 can be used, for one type of sample but also multiple types of samples (biomolecules) can be measured at the same time. As a result, the measurement throughput is improved.

Figure 84:
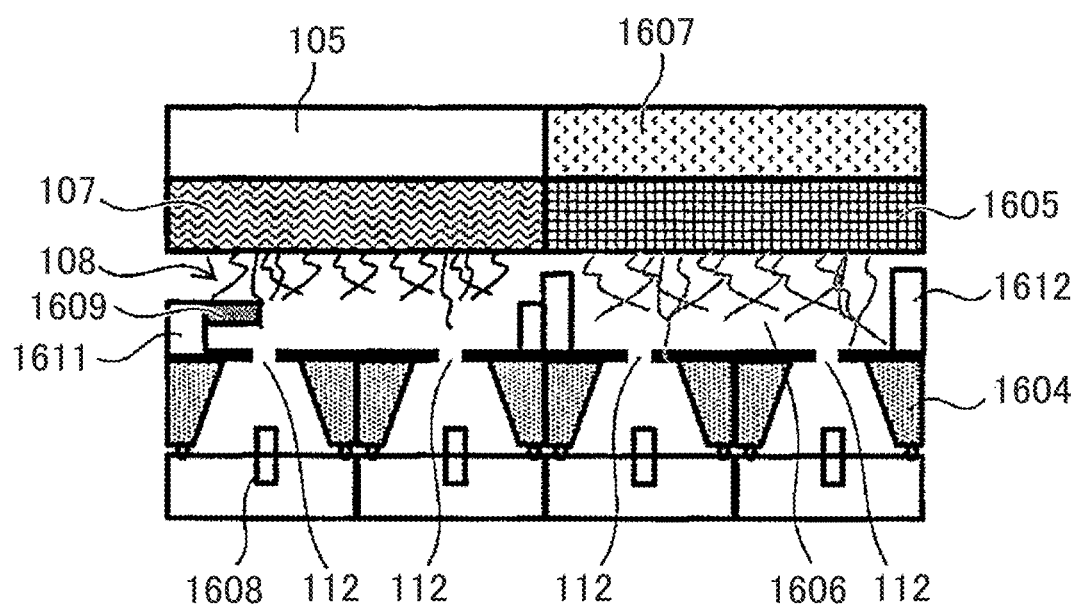
FIG. 84 is a schematic cross-sectional view illustrating a third, example of the biomolecule measuring device having parallelized nanopore devices.
Figure 85:
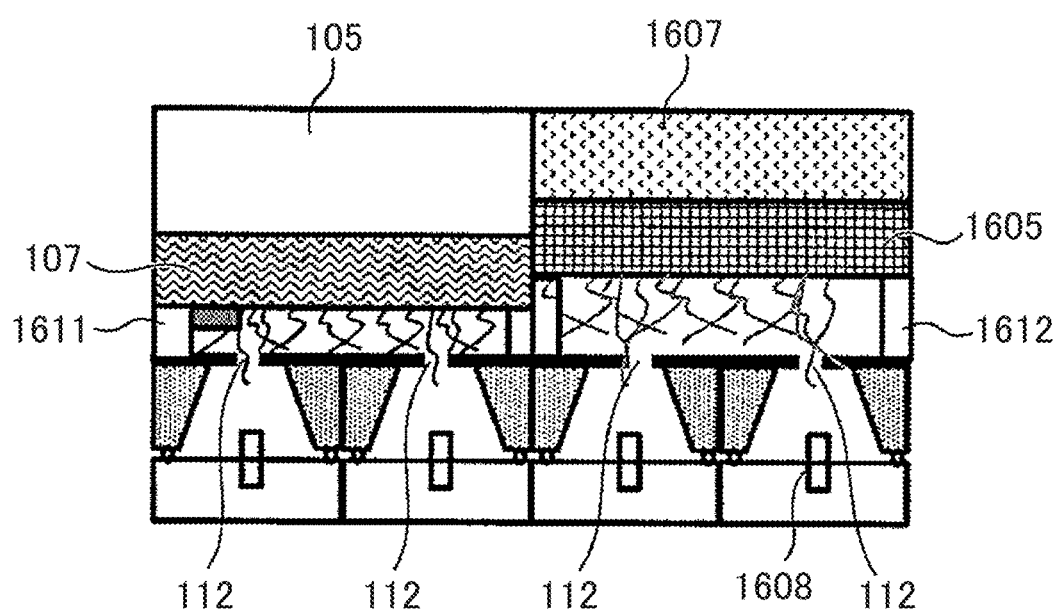
FIG. 85 is a schematic cross-sectional view illustrating the third example of the biomolecule measuring device having parallelized nanopore devices.

FIGS. 82 and 84 are schematic cross-sectional views showing a third example of the biomolecule measuring device having the parallelized nanopore devices. An illustration of the grooves 115 is omitted for simplification of illustration. In this example, the multiple driving mechanisms are placed above the multiple aligned nanopore devices 1604. The respective driving mechanisms are connected with the immobilizing members, and the different types of biomolecules are immobilized on the respective immobilizing members. The space defining members can also be provided for the respective immobilizing members.

In the illustrated example, the first driving mechanism 105 and a second driving mechanism 1607 are disposed above the multiple nanopore devices 1604. The first immobilizing member 107 is connected to the first driving mechanism 105 and the second immobilizing member 1605 is connected to the second driving mechanism 1607. The first biomolecules 108 are coupled to the first immobilizing member 107 and the second biomolecules 1606 are coupled to the second immobilizing member 1605. The first space defining member 1611 is provided for the first immobilizing member 107 and the second space defining member 1612 is provided for the second immobilizing member 1605. The first space defining member 1611 and the second space defining member 1612 have different film thicknesses. As a result, even the height of the biomolecules different in the length can be adjusted independently. A slit or the like is provided in the first and second space defining members 1611 and 1612. The first and second immobilizing members 107 and 1605 descend, and when the first and second space defining members 1611 and 1612 come into contact with each other, the solution filling the upper portion of the nanopore 112 does not become independent for each sample. As a result, the electrode disposed on the top of the multiple nanopores 112 may be only the common electrode 1609.

In any of the examples, a magnitude relationship between the number a of nanopores and the number b of biomolecules on the immobilizing member is a<b. The biomolecules are closely bound to the immobilizing member, as a result of which when the immobilizing members are vertically descended toward the nanopore devices, the biomolecules are necessarily introduced into the nanopores.

Example 7

Figure 86:
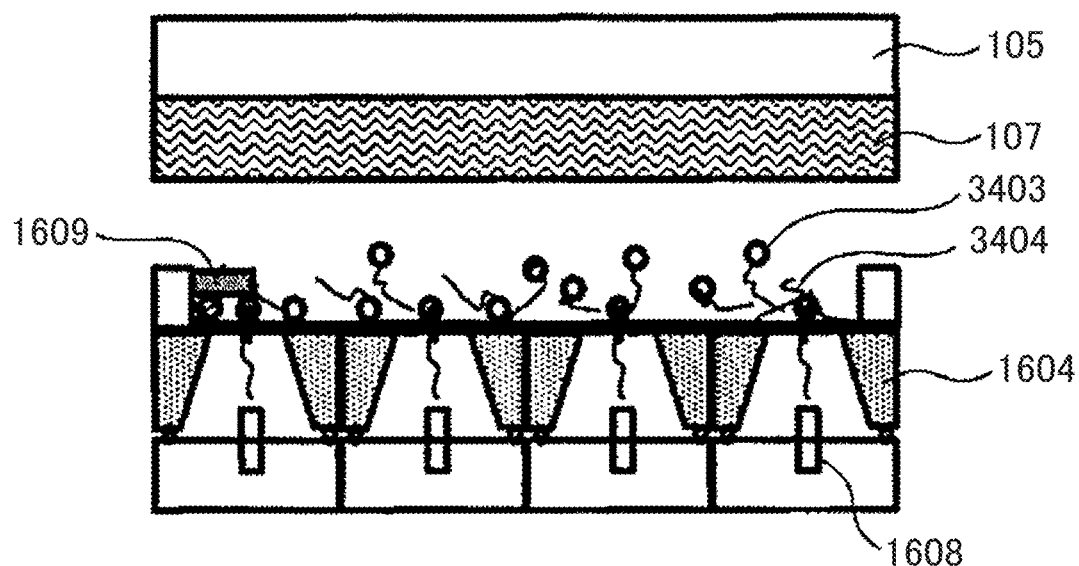
FIG. 86 is a schematic cross-sectional view illustrating a measurement procedure using magnetic beads.
Figure 87:
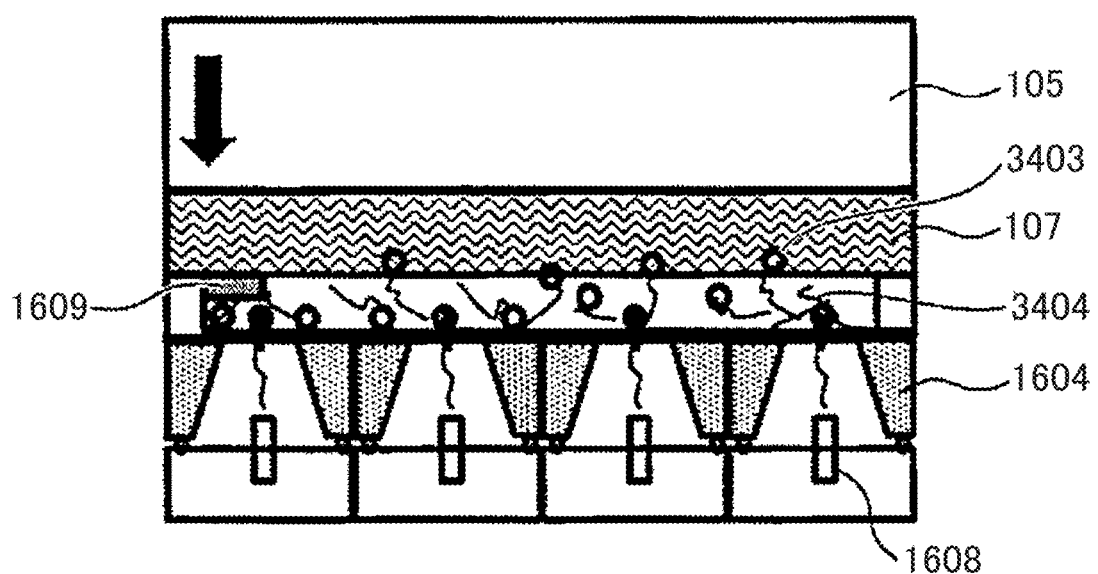
FIG. 87 is a schematic cross-sectional view illustrating the measurement procedure using the magnetic beads.
Figure 88:
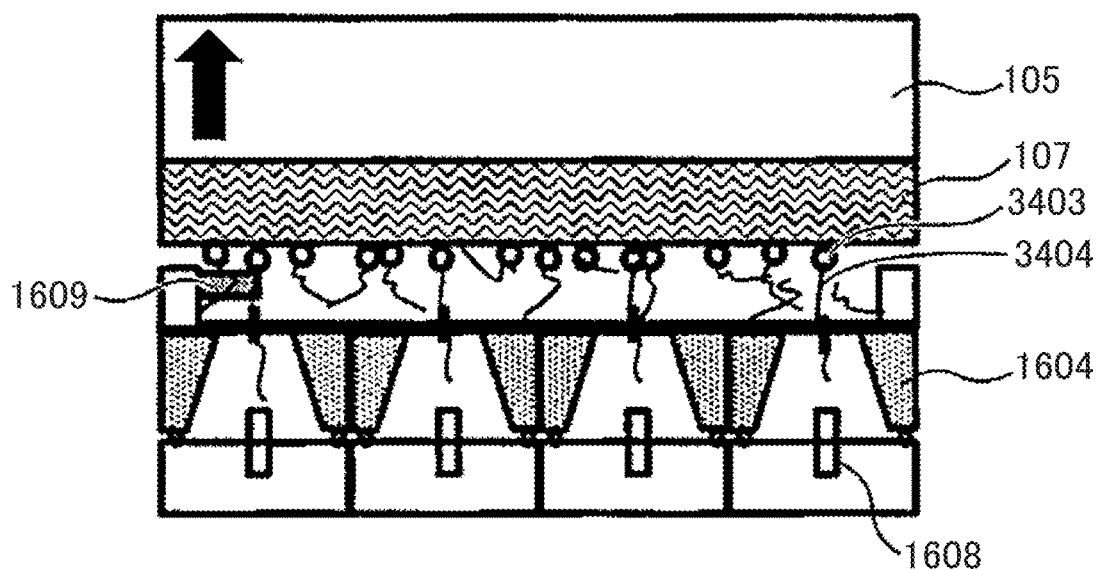
FIG. 88 is a schematic cross-sectional view illustrating the measurement procedure using the magnetic beads.

An example in which magnetic beads are used as another means for immobilizing the biomolecules to the immobilizing member will be described. In the present embodiment, an example in which the device shown in FIGS. 86 to 88 is used as the biomolecule measuring device will be described. The immobilizing member is made of a magnetic material.

FIGS. 86 to 88 are schematic cross-sectional views illustrating procedures for immobilizing the biomolecules to the immobilizing member with the use of the magnetic beads for measurement. For simplification of description, an illustration of the grooves 115 is omitted. The biomolecules that are previously immobilized on the magnetic beads are prepared.

In a first step, as shown in FIG. 86, a voltage is applied between Ag and AgCl electrodes 1608 placed in the parallelized nanopore devices 1604 and the common electrode 1609 to generate an electric field in an electrolyte solution around each nanopore. Then, biomolecules 3404 immobilized on the magnetic beads 3403 are migrated by electrophoresis to introduce the biomolecules into the nanopores of the parallelized nanopore devices 1604. In this example, the ion currents derived from the respective nanopores are monitored, and an effective nanopore device in which the biomolecule enters the nanopore can be confirmed according to a change rate of the ion currents.

In a second step, as shown in FIG. 87, while a voltage application through the nanopores in the first step is continued, the driving mechanism 105 drives the immobilizing member 107 toward the nanopore devices 1604 as indicated by an arrow, and the magnetic beads 3403 are attracted and immobilized on the immobilizing member 107 by a magnetic force.

In a third step, as indicated by the arrow in FIG. 88, the driving mechanism 105 drives the immobilizing member 107 in a direction away from the nanopore devices 1604 at a controlled speed, and the ion current changed due to the biomolecules moving in the nanopores is detected by the ammeter 109 and recorded in the PC 110. The driving mechanism 105 configured by a piezoelectric element can drive the immobilizing member 107 at an arbitrary speed, and more specifically when reading the sequence of the DNA, the DNA immobilized on the magnetic beads are moved in the nanopores at a rate of 3.4 nm/ms or lower, thereby being capable of performing high-precision reading.

According to the present example, there is no need to initially position the nanopores and the biomolecules. In addition, since the biomolecules can be diffused into the magnetic field generated in the vicinity of the nanopores and introduced into the nanopores, a probability that the nanopores through which the biomolecules do not pass exist among the parallelized nanopores can be reduced.

Example 8

Figure 89:
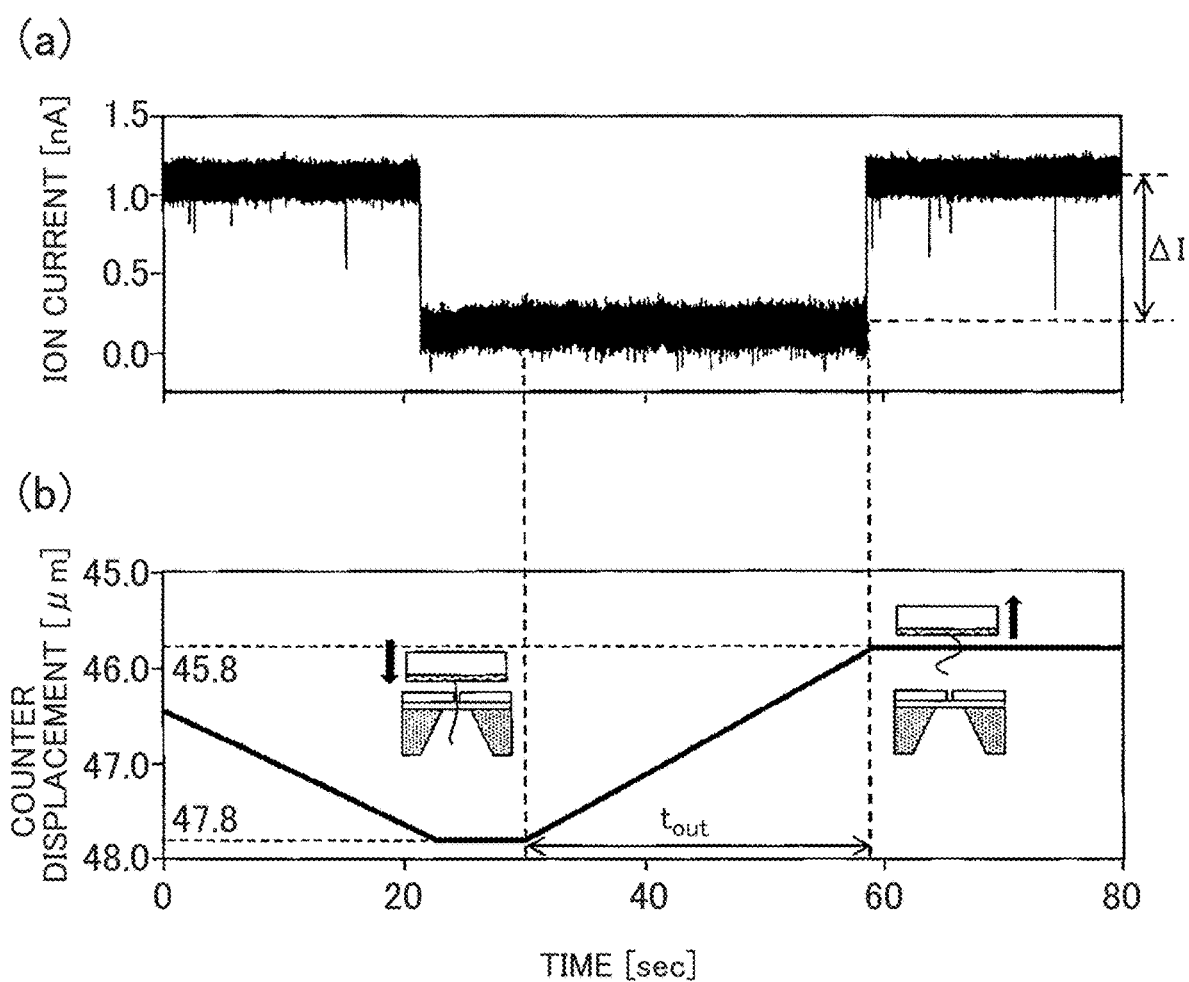
FIG. 89 are diagrams illustrating a state of elimination of a blockage current associated with driving of the biomolecule immobilizing member.

FIG. 89 is a diagram illustrating a state of eliminating a blockage current caused by driving of an immobilizing member by a driving mechanism. With the use of the biomolecule measuring device shown in FIG. 1, an immobilizing member 107 in which ss-poly (dA) of a chain length 5 k is immobilized on a surface modulated with APTES/glutaraldehyde was brought closer to the vicinity of the nanopore 112 of the nanopore device 101. As a result, as shown in FIG. 89(*a*), a blocking signal was confirmed and when the immobilizing member 107 was separated from the nanopore device 101, the blockage signal was eliminated. FIG. 89(*b*) shows a trajectory of the immobilizing member 107 at the same time as that of FIG. 89(*a*). As a counter displacement increases, the nanopore device 101 and the immobilizing member 107 come closer to each other. About 1 second after confirming the decrease in the ionic current, the driving of the immobilizing member 107 by the driving mechanism 105 was stopped. After about 10 seconds, a distance between the nanopore device 101 and the immobilizing member 107 started to increase. At the time when the ion current again increased (after 30 seconds passed), the driving by the driving mechanism 105 was stopped again. When the immobilizing member 107 with the immobilized DNA was brought closer to the nanopore 112, the ion current decreased, and the ion current was moved away from the nanopore 112, thereby returning to an original current value. This indicates that introduction and withdrawal of the DNA into and from the nanopore 112 occur due to the driving of the immobilizing member 107 by the driving mechanism 105.

Figure 90:
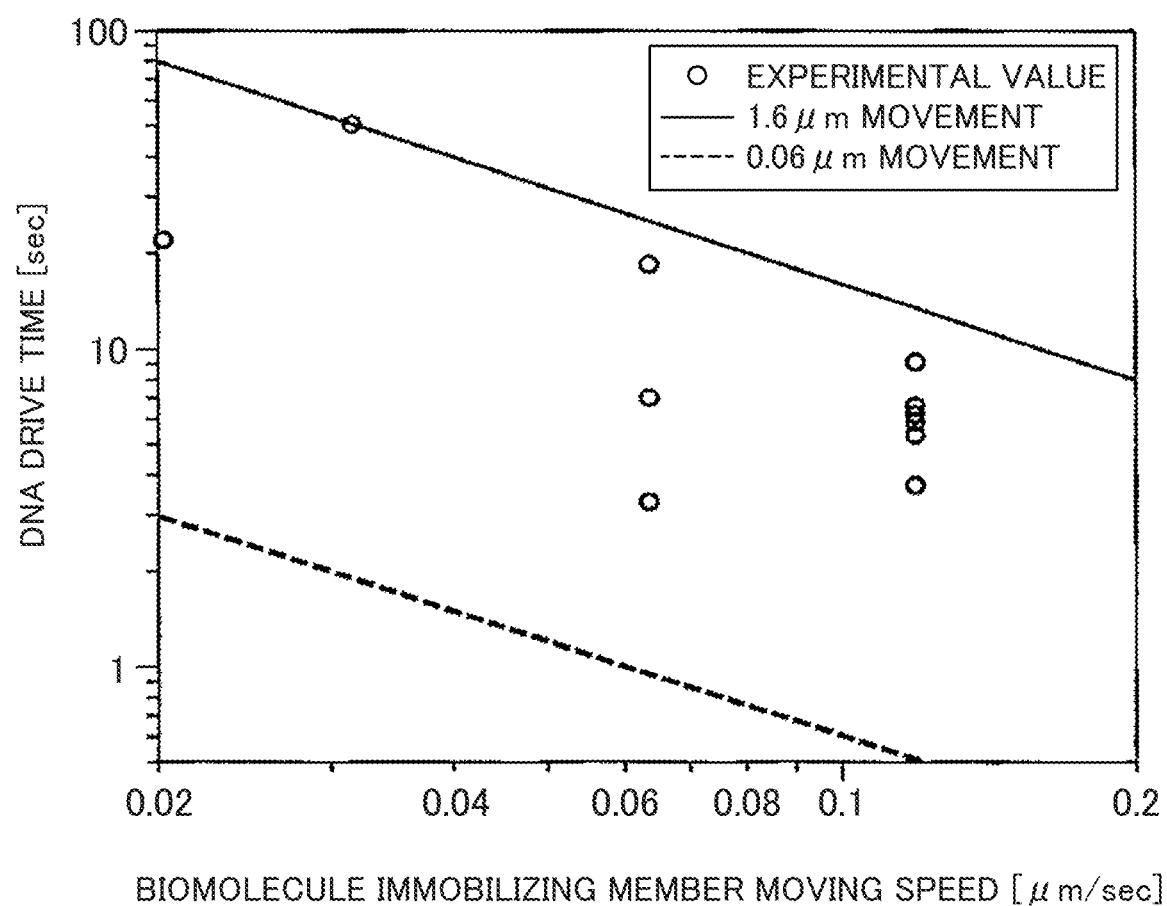
FIG. 90 is a diagram showing a relationship between a moving speed of the biomolecule immobilizing member and a DNA driving time.

As shown in FIG. 89(b), a time interval (DNA driving time) from a time when the driving mechanism 105 start to be driven for the purpose of separating the immobilizing member 107 from the nanopore device 101 to a time when the blockage signal is eliminated is defined as $t_{out}$. On the other hand, the moving speed of the immobilizing member 107 was obtained according to a relationship with a counter speed corresponding to a set speed of the driving mechanism 105. A relationship between the moving speed of each immobilizing member 107 and the acquired DNA driving time ($t_{out}$) is shown in FIG. 90. Plots in FIG. 90 are experimental values. In this example, the DNA driving distance, that is, a maximum length introduced into the nanopore 112 of the DNA in each measurement is determined according to a position at which the driving of the immobilizing member 107 stops after the nanopore 112 is blocked with the DNA. Since the driving of the immobilizing member 107 by the driving mechanism 105 is manually stopped after a blockage signal indicating that the DNA has been inserted into the nanopore 112 is visually confirmed, it is conceivable that it takes about one second at the shortest since the DNA is actually inserted into the nanopore 112 until the driving of the immobilizing member 107 stops. Therefore, the DNA of about 60 to 100 nm at the shortest always enters the nanopore 112.

In FIG. 90, a solid line is a calculated value of the maximum DNA driving time obtained from a length of the immobilized DNA. Also, a broken line is a calculated value of the minimum DNA driving time when the DNA of 60 nm enters the nanopore. Since the DNA driving time experimentally measured falls within a range from the solid line to the broken line, the acquired blockage signal is derived from the DNA on the immobilizing member, and the actually measured value is conceived to be reasonable. In addition, the actually measured DNA driving time is distributed in a direction in which the DNA driving time becomes longer as the moving speed of the immobilizing member 107 is lower. It is conceivable that this indicates that the DNA on the immobilizing member 107 is transported in the nanopore 112 depending on the driving speed of the driving mechanism 105.

Figure 91:
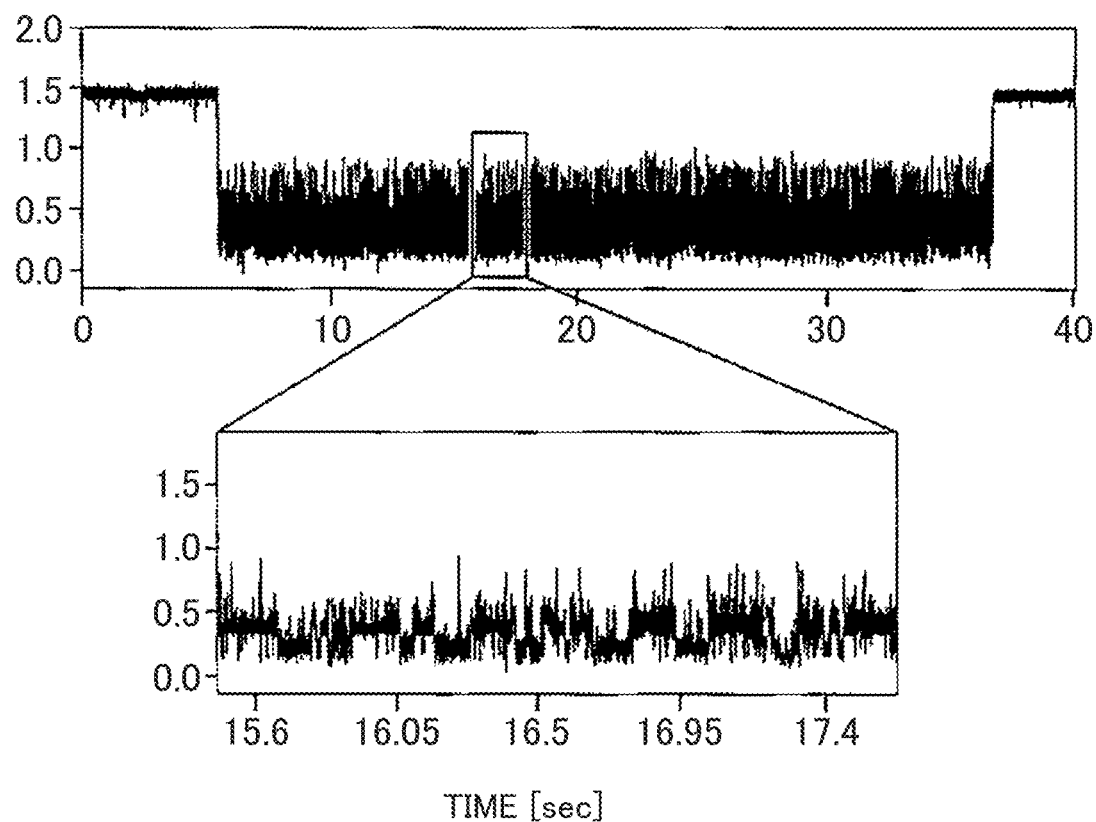
FIG. 91 is a diagram illustrating an ion current trace example of a dual polymer mixed, molecule ((dA50dC50)m).

FIG. 91 is a diagram showing the results of binding the molecules (dA50dC50)m) in which polymer of dA50dC50 is repeatedly extended to the immobilizing member in the same manner and measuring the molecules. When the immobilizing member was brought closer to the nanopore device, the blockage signal as acquired in FIG. 89 was confirmed. As a result of analyzing the current after blockade, a signal of two levels was obtained. In this way, the biomolecules were bound to the immobilizing member and the molecule passage speed was decreased, thereby being capable of measuring a state in which a blockage signal intensity is different depending on the molecular species.

Example 9

As another technique for realizing a reduction in the solution resistance, in addition to forming the groove structure, porous silica may be used as a material of the immobilizing member. The immobilizing member of the biomolecules may be made of porous silica, or at least a part of the immobilizing member may be made of porous silica. For example, a surface of the immobilizing member which comes close to the nanopore device (biomolecule measuring device) may be made of porous silica. In this configuration, the biomolecules to be measured are immobilized on at least the outermost surface of porous silica (a surface opposed to the nanopore device).

Pores are provided in a surface and interior of porous silica. For example, with the provision of the porous silica on a surface of the immobilizing member, when the immobilizing member comes closer to the nanopore device, solution can pass through the pores. This makes it possible to reduce an increase in passage resistance generated when the immobilizing member comes closer to the nanopore device.

Figure 92:
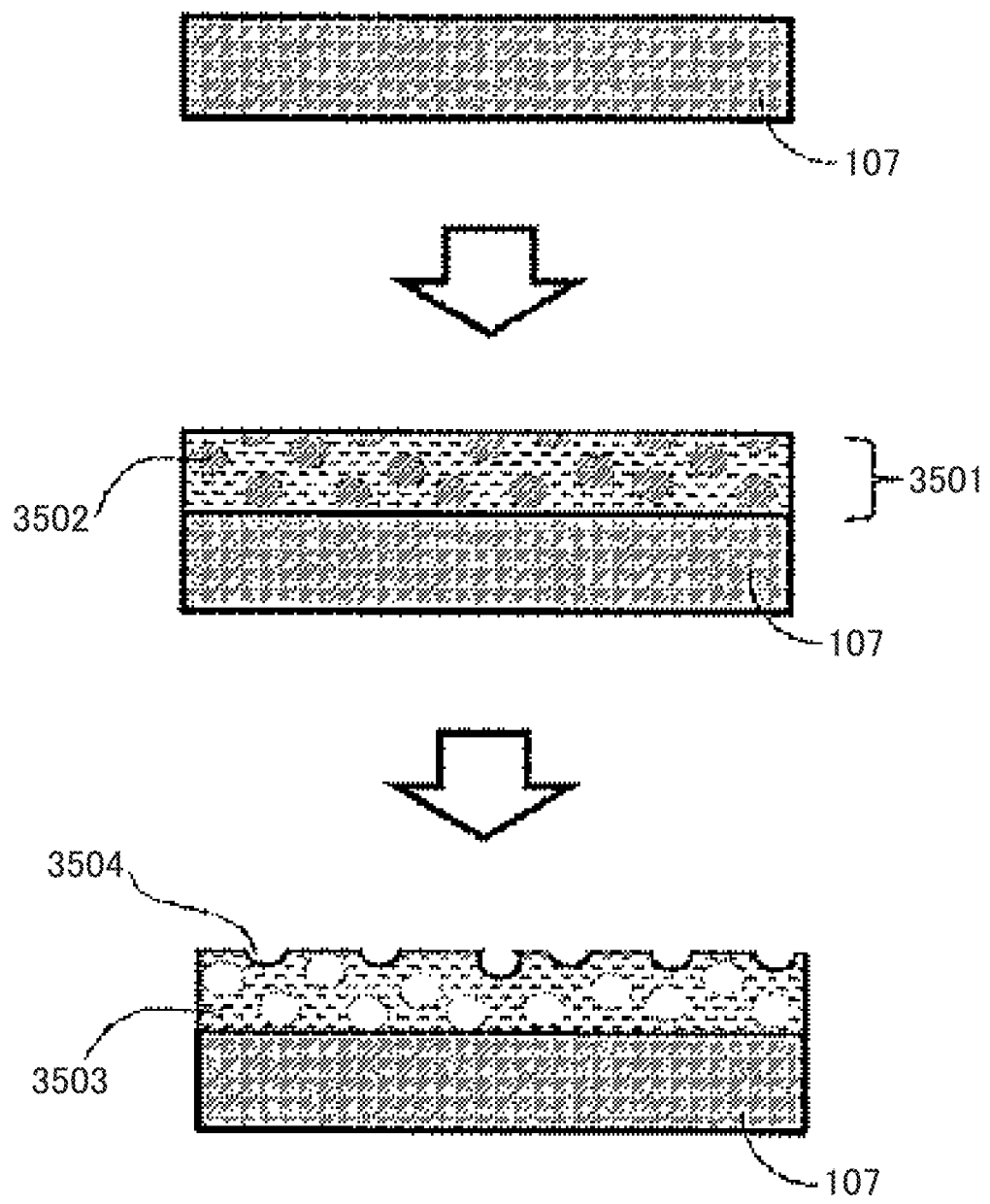
FIG. 92 is a diagram illustrating a biomolecule immobilizing member having a porous material portion.

FIG. 92 shows a unit for forming a biomolecule immobilizing member which is partially made of porous silica. A coating solution 3501 in which a silica precursor and a surfactant are mixed together is applied to a surface of a silicon substrate 107 as an immobilizing member. At this time, a micelle aggregate is formed in the coating solution. Thereafter, firing is carried out to remove the micelle aggregate 3502 from the coating solution to form a porous silica film 3503. Reference numeral 3504 indicates the pores produced after the micelle aggregate 3502 has been removed.

In this example, the degree of reduction of the passage resistance is determined according to a micelle size and a density. The surfactant is a cationic surfactant and more preferably has a hydrophobic group having 16 or more carbon atoms or a hydrophobic group such as benzyl group and phenyl group. The micelle size is determined according to a chain length of the hydrophobic group, and an average pore diameter produced after sintering varies in a range from 3 nm to less than 5 nm. For example, when a surfactant with a carbon chain C18 is used, the average pore diameter of 3.5 nm can be provided. Since the density of the pores correlates with the density of the micelles, the density of the pores can be adjusted by the amount ratio of the surfactant. A pore volume varies in a range of 0.1 to 2.0 $cm^3$/g and can be controlled with 20% or more of the silica volume at minimum. In order to prevent the resistance value from increasing due to approach, a reduction in the density of a structure by about 100 times is required. For that reason, there is a need to realize the density reduction of 99% or more in volume ratio, which falls within a controllable range of this structure.

In order to prevent an increase in the resistance value, it is necessary for an aqueous solution to permeate also into the pore. This matter can be solved by making the porous silica surface hydrophilic. In addition to hydrophilization through a plasma treatment, a hydrophilic state can be maintained by organosilicon compound having amino group-modified siloxane bond. The organosilicon compound having a siloxane bond is also useful for reinforcing a skeleton of porous structure.

Since the porous silica is a solid silicon material, a hydroxyl group can be formed at a silicon end by plasma irradiation, and an amino group can be modified at the end with the use of APTES, and a crosslinking agent having a carboxyl terminal such as glutaraldehyde and amino group-terminated biomolecules can be immobilized.

The present invention is not limited, to the examples described above but includes various modifications. The abovementioned examples are described in detail for the purpose of describing the present invention in an easy-to-understand manner, and the present invention does not always provide all of the configurations described above. Also, a part of one configuration example can be replaced with another configuration example, and the configuration of one example can be added with the configuration of another example. Also, in a part of the respective configuration examples, another configuration can be added, deleted, or replaced independently or in combination.

The above-described respective configurations, functions, and so on of the measurement unit and the control unit may be realized by allowing a processor to interpret and execute programs for realizing the respective functions. The information on the program, table, file, and the like for realizing the respective functions can be stored in a recording device such as a memory, a hard disc, or an SSD (Solid State Drive), or a recording medium such as an IC card, an SD card, or a DVD. In addition, some or all of the respective configurations, functions and so on of the measurement unit and the control unit may be realized by hardware designed by, for example, an integrated circuit.

LIST OF REFERENCE SIGNS 100, biomolecule characterization analyzing device
101, nanopore device
102, electrolyte solution
103a, 103b, Ag and AgCl electrodes
104, power supply
105, driving mechanism
106, driving mechanism control unit
107, biomolecule immobilizing member
108, biomolecule
109, ammeter
110, PC
111, connection member
112, nanopore
113, thin film
114, space defining member
115, groove
115a, convex portion of groove
115b, concave portion of groove
1501, laser irradiation unit
1503, mirror
1504, relative position monitor
1505, control unit
1506, 1511, rotation mechanism
1507, adjustment mechanism
3501, coating solution mixed with silica precursor and surfactant
3502, micelle aggregate
3503, porous silica membrane
3504, pore

The invention claimed is:

1. A biomolecule measuring device comprising:
a first liquid tank filled with an electrolyte solution;
a second liquid tank filled with the electrolytic solution;
a nanopore device that supports a thin film having a nanopore and is provided between the first liquid tank and the second liquid tank to communicate the first liquid tank with the second liquid tank through the nanopore;
an immobilizing member that is disposed in the first liquid tank, has a size larger than that of the thin film and to which biomolecules are immobilized;
a driving mechanism that drives the immobilizing member in a direction closer to or away from the thin film;
a first electrode that is provided in the first liquid tank;
a second electrode that is provided in the second liquid tank;
a stop mechanism that prevents a contact between the immobilizing member and the thin film;
a power supply that applies a voltage between the first electrode and the second electrode; and
a measurement unit that measures an ionic current flowing between the first electrode and the second electrode,
wherein at least one of the nanopore device and the immobilizing member has a groove structure in a region where the nanopore device and the immobilizing member are opposed to each other, and
wherein the measurement unit acquires sequence information on the biomolecules by an ionic current measured when the biomolecules immobilized on the immobilizing member pass through the nanopore, and
wherein the groove structure is continuously formed in a range where the nanopore device and the immobilizing member are opposed to each other.

2. The biomolecule measuring device according to claim 1,
wherein a cross section of the groove structure is one of a rectangle, a triangle, a semicircle, and a trapezoid.

3. The biomolecule measuring device according to claim 1,
wherein the biomolecules are immobilized on a convex portion of the groove structure.

4. The biomolecule measuring device according to claim 1,
wherein a convex portion and a concave portion of the groove structure are made of the same material.

5. The biomolecule measuring device according to claim 1,
wherein a convex portion and a concave portion of the groove structure are made of different materials.

6. The biomolecule measuring device according to claim 1,
wherein a plurality of types of biomolecules are immobilized on the immobilizing member through a plurality of different markers.

7. The biomolecule measuring device according to claim 1,
wherein a groove depth of the groove structure is equal to or more than 5 μm.

8. The biomolecule measuring device according to claim 1,
wherein a width of a convex portion of the groove structure is equal to or more than a pitch of the biomolecules immobilized on the immobilizing member.

9. The biomolecule measuring device according to claim 1,
wherein the driving mechanism has a function of bringing the immobilizing member into contact with the nanopore device.

10. The biomolecule measuring device according to claim 1, further comprising:
a laser irradiation mechanism that irradiates the groove structure with a laser; and a control unit that controls movement or rotation of the immobilizing member with the use of an image obtained by irradiation of the laser.

11. The biomolecule measuring device according to claim 1, further comprising:
a control unit that controls movement or rotation of the immobilizing member,
wherein the control unit controls the movement or rotation of the immobilizing member by monitoring a solution resistance around the nanopore device.

12. The biomolecule measuring device according to claim 1,
wherein the groove structure is formed on a surface of the immobilizing member.

13. The biomolecule measuring device according to claim 1,
wherein the immobilizing member is made of porous silica or the porous silica is provided on a surface of the immobilizing member close to the nanopore device, and
the biomolecules to be measured are immobilized on a surface of the porous silica opposed to the nanopore device.

14. A biomolecule measuring device comprising:
a first liquid tank filled with an electrolyte solution;
a second liquid tank filled with the electrolytic solution;
a nanopore device that supports a thin film having a nanopore and is provided between the first liquid tank and the second liquid tank to communicate the first liquid tank with the second liquid tank through the nanopore;
an immobilizing member that is disposed in the first liquid tank, has a size larger than that of the thin film and to which biomolecules are immobilized;
a driving mechanism that drives the immobilizing member in a direction closer to or away from the thin film;
a first electrode that is provided in the first liquid tank;
a second electrode that is provided in the second liquid tank;
a stop mechanism that prevents a contact between the immobilizing member and the thin film;
a power supply that applies a voltage between the first electrode and the second electrode; and
a measurement unit that measures an ionic current flowing between the first electrode and the second electrode,
wherein at least one of the nanopore device and the immobilizing member has a groove structure in a region where the nanopore device and the immobilizing member are opposed to each other,
wherein the measurement unit acquires sequence information on the biomolecules by an ionic current measured when the biomolecules immobilized on the immobilizing member pass through the nanopore,
wherein the stop mechanism includes a space defining member that is disposed on the nanopore device and defines a space between the immobilizing member and the thin film, and
wherein the groove structure is formed in the space defining member.

15. A bio molecule measuring device comprising:
a first liquid tank filled with an electrolyte solution;
a second liquid tank filled with the electrolytic solution;
a nanopore device that supports a thin film having a nanopore and is provided between the first liquid tank and the second liquid tank to communicate the first liquid tank with the second liquid tank through the nanopore;
a first electrode that is provided in the first liquid tank;
a second electrode that is provided in the second liquid tank;
a power supply that applies a voltage between the first electrode and the second electrode; and
a measurement unit that measures an ionic current flowing between the first electrode and the second electrode,
wherein the first liquid tank has a micro flow path in a region in the vicinity of the nanopore,
the nanopore device has a groove structure, and
the measurement unit acquires sequence information on the biomolecules by an ionic current measured when the biomolecules pass through the nanopore.

16. A biomolecule measuring device comprising:
a first liquid tank filled with an electrolyte solution;
a plurality of second tanks filled with the electrolyte solution and electrically insulated from each other;
a nanopore device that supports a thin film having nanopores and is provided between the first liquid tank and the plurality of second tanks to communicate the first liquid tank with one of the second liquid tanks through a nanopore;
an immobilizing member that is disposed in the first liquid tank, has a size larger than that of the thin film and to which biomolecules are immobilized;
a driving mechanism that drives the immobilizing member in a direction closer to or away from the thin film;
a first electrode that is provided in the first liquid tank;
a plurality of second electrodes that are provided in the plurality of second liquid tanks, respectively, in a one-to-one basis;
a stop mechanism that prevents a contact between the immobilizing member and the thin film;
a power supply that applies a voltage between the first electrode and the second electrodes; and
a measurement unit that measures an ionic current flowing between the first electrode and the second electrodes,
wherein at least one of the nanopore device and the immobilizing member has a groove structure in a region where the nanopore device and the immobilizing member are opposed to each other, and
wherein the measurement unit acquires sequence information on the biomolecules by an ionic current measured when the biomolecules immobilized on the immobilizing member pass through the nanopore, and
wherein the groove structure is continuously formed in a range where the nanopore device and the immobilizing member are opposed to each other.

* * * * *